(12) United States Patent
Chambournier et al.

(10) Patent No.: US 8,901,319 B2
(45) Date of Patent: Dec. 2, 2014

(54) PROCESS FOR THE PREPARATION OF F-SERIES PROSTAGLANDINS

(75) Inventors: Gilles Chambournier, Ann Arbor, MI (US); Andriy Kornilov, Ypsilanti, MI (US); Hussein M. Mahmoud, Ann Arbor, MI (US); Ivan Vesely, Neratovice (CZ); Stephen D. Barrett, Hartland, MI (US)

(73) Assignee: Cayman Chemical Company, Incorporated, Ann Arbor, MI (US)

( * ) Notice: Subject to any disclaimer, the term of this patent is extended or adjusted under 35 U.S.C. 154(b) by 0 days.

(21) Appl. No.: 13/500,254

(22) PCT Filed: Oct. 16, 2009

(86) PCT No.: PCT/US2009/061076
§ 371 (c)(1),
(2), (4) Date: Jul. 23, 2012

(87) PCT Pub. No.: WO2011/046569
PCT Pub. Date: Apr. 21, 2011

(65) Prior Publication Data
US 2012/0283451 A1 Nov. 8, 2012

(51) Int. Cl.
*C07D 405/00* (2006.01)
*C07D 307/935* (2006.01)

(52) U.S. Cl.
CPC .................................. *C07D 307/935* (2013.01)
USPC ............................. 549/214; 549/305; 562/503

(58) Field of Classification Search
USPC ......................................................... 549/214
See application file for complete search history.

(56) References Cited

U.S. PATENT DOCUMENTS

| | | | |
|---|---|---|---|
| 4,195,183 A | 3/1980 | Gandolfi et al. | |
| 4,322,557 A | 3/1982 | Andrews | |
| 6,015,922 A | 1/2000 | Conrow | |
| 7,268,239 B2 * | 9/2007 | Greenwood et al. | 549/305 |
| 7,947,740 B2 * | 5/2011 | Gutman et al. | 514/622 |
| 2007/0155973 A1 | 7/2007 | Yao et al. | |
| 2007/0167641 A1 | 7/2007 | Wei et al. | |

FOREIGN PATENT DOCUMENTS

| | | |
|---|---|---|
| EP | 1810967 A1 | 7/2007 |
| WO | 9202496 | 2/1992 |
| WO | WO 99/02165 A1 | 1/1999 |
| WO | 0155101 A2 | 8/2001 |
| WO | WO 01/55101 A2 | 8/2001 |
| WO | WO 02/96868 A2 | 12/2002 |
| WO | 2010109476 A2 | 9/2010 |
| WO | WO 2010/097672 A1 | 9/2010 |

OTHER PUBLICATIONS

Armarego, W.L.F., Purification of Laboratory Chemicals, 2003, Butterworth & Heinemann, 5th Edition, Chapter 1.*
Armaregp, W.L.F., Purification of Laboratory Chemicals, 2003, Butterworth & Heinemann, 5th Edition, Table 7.*
Greene, T. W., Greene's Protective Groups in Organic Synthesis, Joh Wiley and Sons, Fourth Edition, Publisehd online Apr. 10, 2006.*
Liljebris, Charlotta et al., "Derivatives of 17-Phenyl-18,19,20-trinorprostaglandin F2a Isopropyl Ester: Potential Antiglaucoma Agents", Journal of Medicinal Chemistry, 1995, pp. 289-304, vol. 3.8.
Liljebris, Charlotta et al., "Palladium Catalyzed Syntheses of Phenyl-Substituted PFG2a Analogues: Potential Anticlaucoma Agents", Bioorganic & Medicinal Chemistry Letters, 1993, pp. 241-244, vol. 3, No. 2.
Japanese Office Action and English Translation for corresponding Japanese Patent Application No. 2012-534150 mailed Oct. 16, 2012, 7 pages.
Ohta, Chisa et al., "An Improved Synthesis of the Selective EP4 Receptor Agonist ONO-4819", J.Org. Chem., 2009, pp. 8298-9308, vol. 74, American Chemical Society.
Theil, F. et al., "Synthesis of a Stable Prostacyclin Analogue", Journal f. prakt. Chemie. Band., 1988, pp. 766-774, vol. 330.
Vostrikov, N. S., et al., Prostanoids: XC.* Extension to the Synthesis of Enprostil of the o-Nitrophenylsulfonylhydrazine Method for Transformation of 2-Propynyl Alcohols into Allenes; Russian Journal of Organic Chemistry, 2005, pp. 967-973, vol. 41, No. 7. (Translated from Zhurnal Organicheskoi Khimii, vol. 41, No. 7, 2005, pp. 988-994.).
Supplementary European Search Report for EP 09 85 0480 dated Mar. 14, 2013, 8 pages.
International Search Report mailed on May 31, 2010 for PCT/US2009/061076, filed on Oct. 16, 2009.
Thomas K. Schaaf et al., Synthesis of [3H]- and -[14C]-Labeled Sulprostone (CP-34,089/ZK-57,671); Prostaglandins, 1982, vol. 24, No. 3; pp. 331-339.

* cited by examiner

*Primary Examiner* — Noble Jarrell
*Assistant Examiner* — John Mauro
(74) *Attorney, Agent, or Firm* — Howard & Howard Attorneys PLLC

(57) ABSTRACT

A process for the synthesis and purification of F-series prostaglandin compounds and synthetic intermediates used to prepare them. The synthetic intermediates are solid and may be purified by precipitation and therefore may form the representative F-series prostaglandin compounds such as latanoprost, bimatoprost, fluprostenol, cloprostenol, and substituted analogs therefrom in highly pure forms.

39 Claims, No Drawings

PROCESS FOR THE PREPARATION OF F-SERIES PROSTAGLANDINS

CROSS REFERENCE TO RELATED APPLICATIONS

The present invention is a national phase application of and claims priority to PCT Application No. PCT/US2009/061076, filed Oct. 16, 2009, entitled "Process For The Preparation Of F-Series Prostaglandins."

FIELD OF THE INVENTION

The present invention relates to a process for the synthesis and purification of F-series prostaglandin compounds and synthetic intermediates used to prepare them.

BACKGROUND OF THE INVENTION

Prostaglandins are found in virtually all tissues and glands and are extremely potent mediators of a diverse group of physiological processes (Funk, C. D. *Science,* 2001, 294, 1871-1875). Prostaglandins can participate in a wide range of body functions, such as the contraction and relaxation of smooth muscle (Andersson, K. E., Forman, A. *Acta Pharmacol. Toxicol.,* 1978, 43 (Suppl. 2), 90-95), the dilation and constriction of blood vessels (Abramovich, D. R., Page, K. R., Parkin, A. M. L. *Br. J. Pharmac.,* 1984, 81, 19-21), control of blood pressure (Anderson, R. J., Berl, T., McDonald, K. M., Schrier, R. W. *Kidney International,* 1976, 10, 205-215), and modulation of inflammation and immunity (Hata, A. N., Breyer, R. M. *Pharmacol. Ther.,* 2004, 103(2), 147-166). In general, prostaglandins and related compounds are transported out of the cells that synthesize them and affect other target cells close to their site of formation, mainly by interacting with the target cell's prostaglandin receptors to stimulate or inhibit some target cell function. They also alter the activities of the cells in which they are synthesized. The nature of these effects may vary from one cell type to another, and from the target cell type.

Prostaglandin $F_{2\alpha}$ ((Z)-7-((1R,2R,3R,5S)-3,5-dihydroxy-2-((S,E)-3-hydroxyoct-1-enyl)cyclopentyl)hept-5-enoic acid) has the following structure:

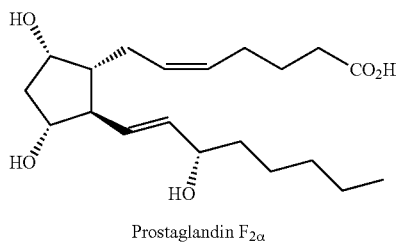 [SMILES: CCCCC[C@H](O)/C=C/[C@@H]1[C@@H](C/C=C\CCCC(=O)O)[C@@H](O)C[C@H]1O]

Prostaglandin $F_{2\alpha}$

Many prostaglandins are characterized by the substituents on the cyclopentyl ring. Prostaglandin $F_{2\alpha}$ and its prostaglandin analogs in general possess two hydroxyl groups on the cyclopentyl ring in a cis configuration relative to each other, and two hydrocarbon side chains (α and ω side chains) on the cyclopentyl ring in a trans configuration relative to each other. Prostaglandin $F_{2\alpha}$ analogs can have a varying number of carbon-carbon double bonds in the hydrocarbon side chains, and side chain substituents may vary. In addition, for $PGF_{2\alpha}$ analogs, the α side chain may terminate with a carboxylic acid moiety (free acid form), a carboxylic ester moiety, or a carboxamide moiety. The ester and amide forms of $PGF_{2\alpha}$ analogs may be used as prodrugs in the treatment of prostaglandin F receptor (FP receptor)-mediated conditions or processes.

Prostaglandin $F_{2\alpha}$ ($PGF_{2\alpha}$) is an endogenous ligand of the Prostaglandin F receptor (FP receptor) that exerts its receptor-mediated physiological activities with $EC_{50}$s in the nanomolar concentration range. The FP receptor is widely distributed in many species (Speroff, L., Ramwell, P. W., *Am. J. Obstet. Gynecol.,* 1970, 107, 1111-1130; Samuelsson, B., Goldyne, M., Granstrom, E., et al., *Ann. Rev. Biochem.,* 1978, 47, 997-1029).

Intravenous, intracameral, and topical administrations of $PGF_{2\alpha}$, have been shown to cause prolonged reduction of intraocular pressure (IOP), a common symptom of glaucoma (Camras, C. B., Bito, L. Z., Eakins, K. E., *Invest. Ophthamol. Vis. Sci.,* 1977, 16(12), 1125-1134; Giuffrè, G., *Graefe's Arch. Clin. Exp. Ophthalmol.,* 1985, 222, 139-141).

Synthetic and relatively metabolically stable analogs of $PGF_{2\alpha}$ having therapeutic use include latanoprost, bimatoprost, fluprostenol, and cloprostenol. The $PGF_{2\alpha}$ analog latanoprost free acid is potent FP receptor agonist with an $EC_{50}$ value of 3.6 nM (Stjernschantz, J., Resul, B., *Drugs of the Future,* 1992, 17 691-704). Latanoprost isopropyl ester, generally known as latanoprost (IUPAC name isopropyl (Z)-7-[(1R,2R,3R,5S)-3,5-dihydroxy-2-[(3R)-3-hydroxy-5-phenylpentyl]-cyclopentyl]hept-5-enoate, common name 17-phenyl-13,14-dihydro trinor Prostaglandin $F_{2\alpha}$ isopropyl ester, trade name Xalatan®), is a prodrug of latanoprost free acid and is used in ophthalmic formulations for the reduction of IOP associated with open angle glaucoma and ocular hypertension (Camras, C. B., Schumer, R. A., Marsk, A., at al., *Arch. Ophthalmol.,* 1992, 110, 1733-1738; Camras, C. B., Alm, A., Watson, P., Stjernschantz, J., *Ophthalmology,* 1996, 103, 1916-1924). Additionally, a single instillation of topical latanoprost has shown to at least temporarily increase blood flow in the optical nerve head (ONH) of subjects with glaucoma (Tamaki, Y., Nagahara, N., Araie, M., et al., *J. Ocular Pharm. Ther.,* 2001, 17(5), 403-411). Topical latanoprost administration also modulates processes such as hair growth (Johnstone, M., *Am. J. Ophthalmol.,* 1997, 124, 544-547). Long-term topical use of latanoprost has been associated with iridial pigmentation and eyelash elongation (Chiba, T., Kashiwagi, K., Ishijima, K., at al., *Jpn. J. Ophthalmol.,* 2004, 48, 141-147)

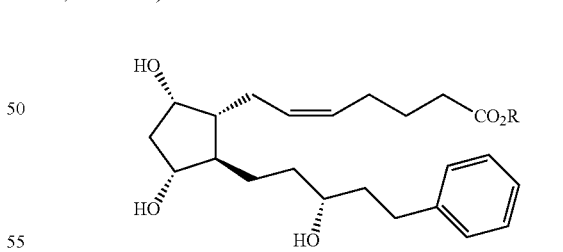

Latanoprost Free Acid (R = H)
Latanoprost (R = $^i$Pr)

Other metabolically stable synthetic analogs of $PGF_{2\alpha}$ have been discovered and developed as treatments for a variety of conditions. Bimatoprost (IUPAC name (Z)-7-[(1R,2R,3R,5S)-3,5-dihydroxy-2-[(E,3S)-3-hydroxy-5-phenylpent-1-enyl]cyclopentyl]-N-ethylhept-5-enamide, common name 17-phenyl trinor Prostaglandin $F_{2\alpha}$ ethyl amide, trade name Lumigan®) is an N-ethyl amide prodrug of its free acid, which is a potent FP receptor agonist (Balapure, A. K., Rexroad, C. E., Kawada, K., at al., *Biochem. Pharmacol.,* 1989, 38, 2375-2381; Lake, S., Gullberg, H., Wahlqvist, J., et al., *FEBS Lett.,* 1994, 355, 317-325). Bimatoprost is approved for treatment of glaucoma-associated IOP (Woodward, D. F., Krauss, A. H., Chen, J., at al., *Survey of Ophthalmology,* 2001, 45, S337-S345) and has also been reported to enhance eyelash growth (Tosti, A., Pazzaglia, M., Voudouris, S., Tosti, G., *Journal of the American Academy of Dermatology,* 2004, 51, S149-S150).

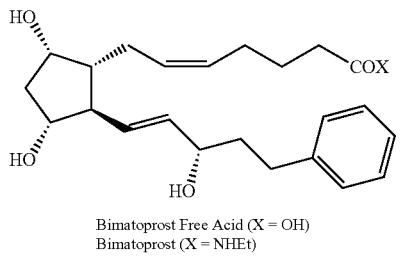

Bimatoprost Free Acid (X = OH)
Bimatoprost (X = NHEt)

The free acid fluprostenol is another synthetic $PGF_{2\alpha}$ analog that is a potent FP receptor agonist (Abramovitz, M., Adam, M., Boie, Y., et al., *Biochim. Biophys. Acta,* 2000, 1483, 285-293). Fluprostenol isopropyl ester (trade name Travoprost®) is a prodrug form of (+)-fluprostenol and is approved for treatment of glaucoma-associated IOP (Sorbera, L. A., Castañer, J., *Drugs of the Future,* 2000, 25, 41-45). Like prodrugs of other FP receptor agonists such as latanoprost and bimatoprost, Travoprost® has been shown to enhance eyelash growth (Eisenberg, D., Toris, C., Camras, C., *Survey of Ophthalmology,* 2002, 47, S105-S115).

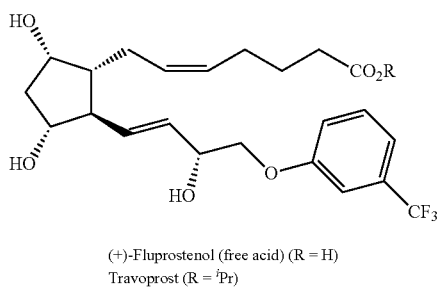

(+)-Fluprostenol (free acid) (R = H)
Travoprost (R = $^{i}$Pr)

Cloprostenol (free acid) also possesses FP receptor agonist activity. Cloprostenol and cloprostenol analogs are useful for treating glaucoma and ocular hypertension (U.S. Pat. No. 6,723,748) and may also be useful in promoting pigmentation and eyelash growth.

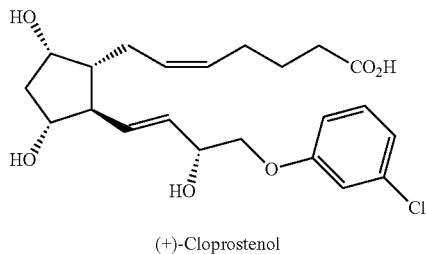 [SMILES: O=C(O)CCC/C=C\C[C@@H]1[C@@H](/C=C/[C@@H](O)COc2cccc(Cl)c2)[C@H](O)C[C@@H]1O]

(+)-Cloprostenol

Procedures describing the synthesis of $PGF_{2\alpha}$ analogs have been disclosed (WO 93/00329; EP 0 364 417 B1; European Patent No. EP 0 544 899 B1; U.S. Pat. No. 7,498,458). WO 93/00329 (and subsequently granted European Patent No. EP 0 544 899 B1) describes a preparation of latanoprost esters from (−)-Corey lactone para-phenylbenzoate (PPB) alcohol, or (3aR,4S,5R,6aS)-4-(hydroxymethyl)-2-oxohexahydro-2H-cyclopenta[b]furan-5-yl biphenyl-4-carboxylate, in eight steps, namely:

1. Moffatt oxidation of the (−)-Corey lactone PPB alcohol to form the corresponding aldehyde:

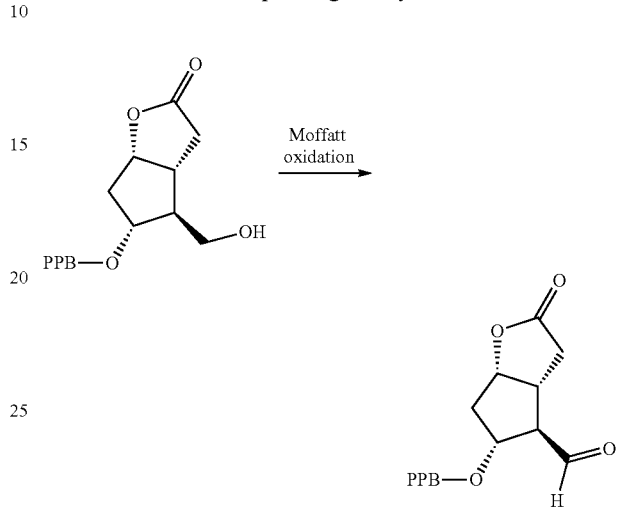

2. Wittig reaction of the aldehyde with triphenyl-2-oxo-4-phenylbutylphosphonium iodide to form the enone intermediate shown below:

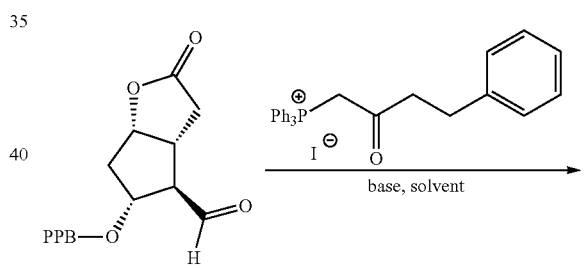

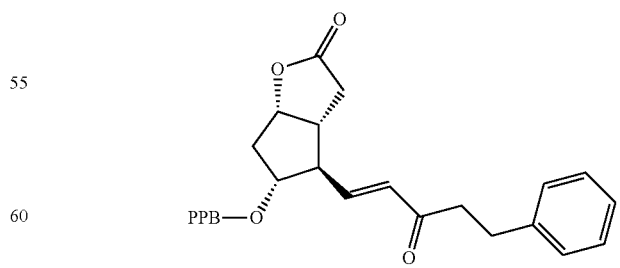

3. Stereoselective reduction of the enone provides an alcohol mixture comprising 15S-alcohol (3a) and 15R-alcohol (Epi-3a) with some enrichment in (3a) as shown below:

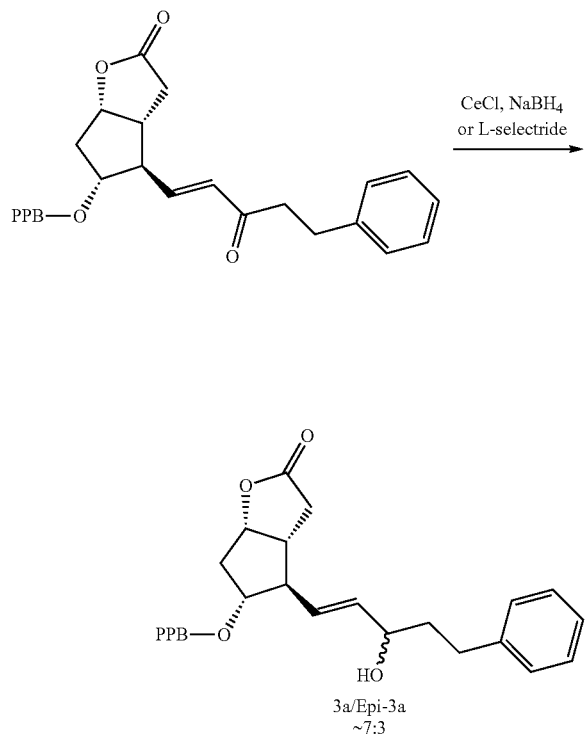

It may be noted here that U.S. Pat. No. 6,689,901 describes a general procedure, and similar specific embodiments, that utilize (−)-B-chlorodiisopinocampheylborane ((−)-DPC) as the reducing agent in the enone reduction step.

4. Hydrogenation to reduce the carbon-carbon double bond completes the framework of the latanoprost ω-chain as shown below:

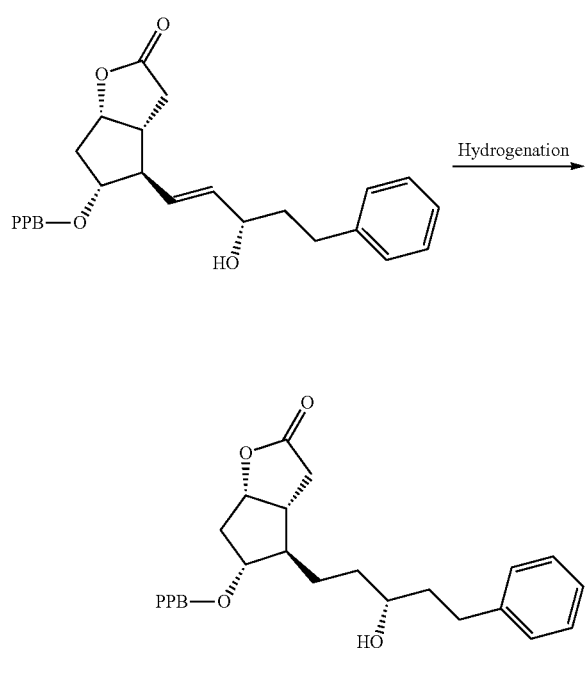

5-6. Lactone reduction and subsequent deprotection provide the lactol as shown below:

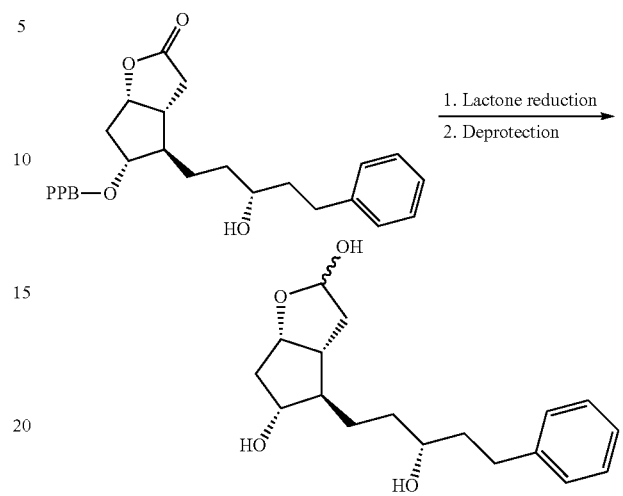

7. A subsequent Wittig reaction with 4-carboxybutyl-triphenylphosphonium bromide provides latanoprost free acid:

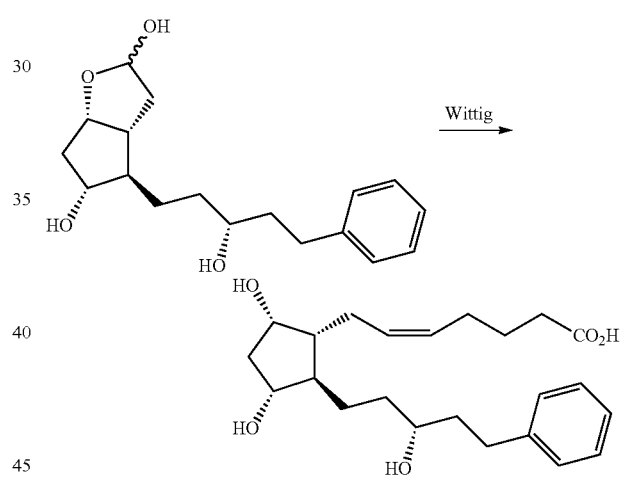

8. Esterification of latanoprost free acid with the desired alcohol ROH affords the corresponding latanoprost ester as described below:

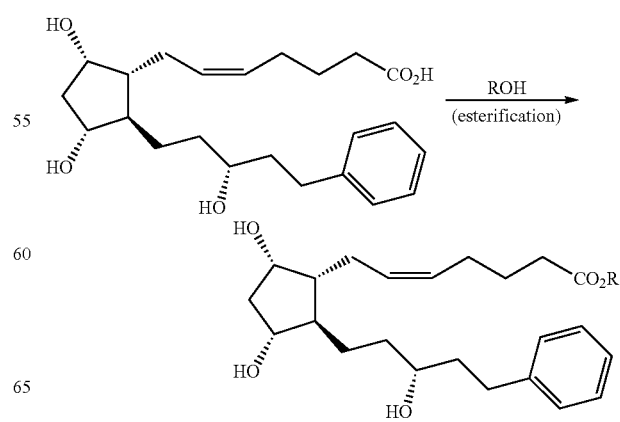

The latanoprost ester synthetic process described in WO 93/00329 suffers from a low overall yield at both the gram and kilogram scale. Loss of valuable material arises from difficulties in purifying intermediates. Purification of the 15S/R-alcohol mixture produced in the enone reduction step to isolate the sufficiently stereopure 15S-alcohol (3a), for example, employs both column chromatography and recrystallization and affords yields of 35% (200 g of starting ketone) and 38% (19.3 kg of starting ketone).

An alternative process is described (Resul, B., Stjernschantz, J., No, K., et al., *J. Med. Chem.*, 1993, 36, 243-248) in which the first Wittig procedure is replaced with the Wadsworth-Emmons method to provide the ketone intermediate with only a small increase in yield. The most significant difference from the above-described process, however, is the removal of the PPB protecting group before lactone reduction, which gives yields essentially equivalent with those of WO 93/00329 over the two steps. Overall, this method provides no significant advantage over that of WO 93/00329. U.S. Pat. No. 7,268,239 discloses a process whereby, in one embodiment, latanoprost is synthesized in eleven linear steps from a protected Corey lactone compound of the following formula:

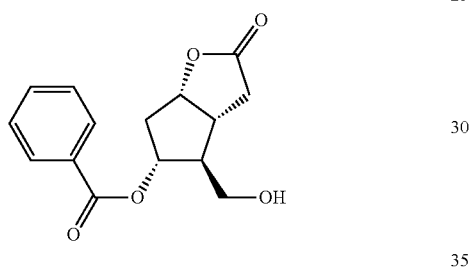

The process comprises the following steps:
1. The benzoyl-protected Corey lactone alcohol is oxidized to the corresponding aldehyde by subjection to a catalytic amount of a stable organic nitroxyl radical as illustrated below:

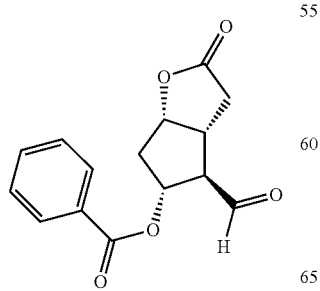

2. The aldehyde is reacted with a phosphonate ester to provide the ketone intermediate as a white solid with 77% yield from the starting material of step 1 as shown below:

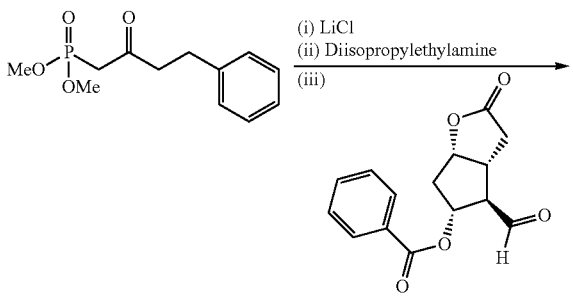

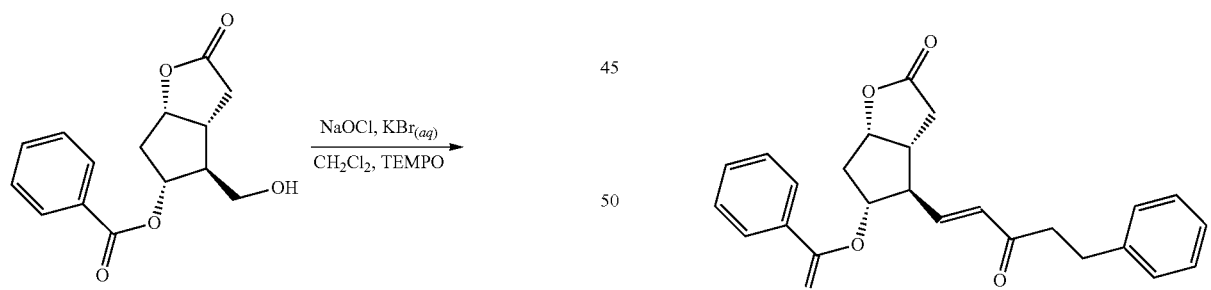

77% yield from protected Corey lactone alcohol

3. The ketone is stereoselectively reduced with borane-dimethylsulfide complex in the presence of a catalytic amount of (R)-tetrahydro-1-methyl-3,3-diphenyl-1H,3H-pyrrolo[1,2-c][1,3,2]oxazaborole ('Corey catalyst') to give a mixture of alcohol epimers enriched with the (S)-hydroxy epimer as a crude oil. A purification that comprises a crystallization step and a tedious chromatography step afford the desired isomer as a white solid with 65% yield as shown below:

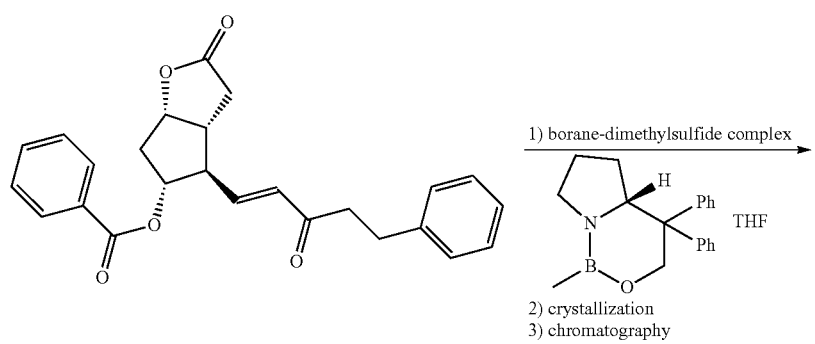

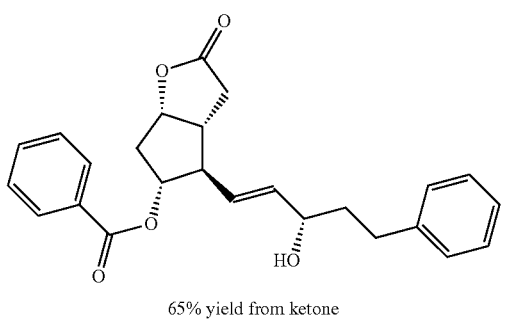

65% yield from ketone

4. The benzoyl protecting group is removed to provide the diol intermediate as an oil with 99.1% yield as shown below:

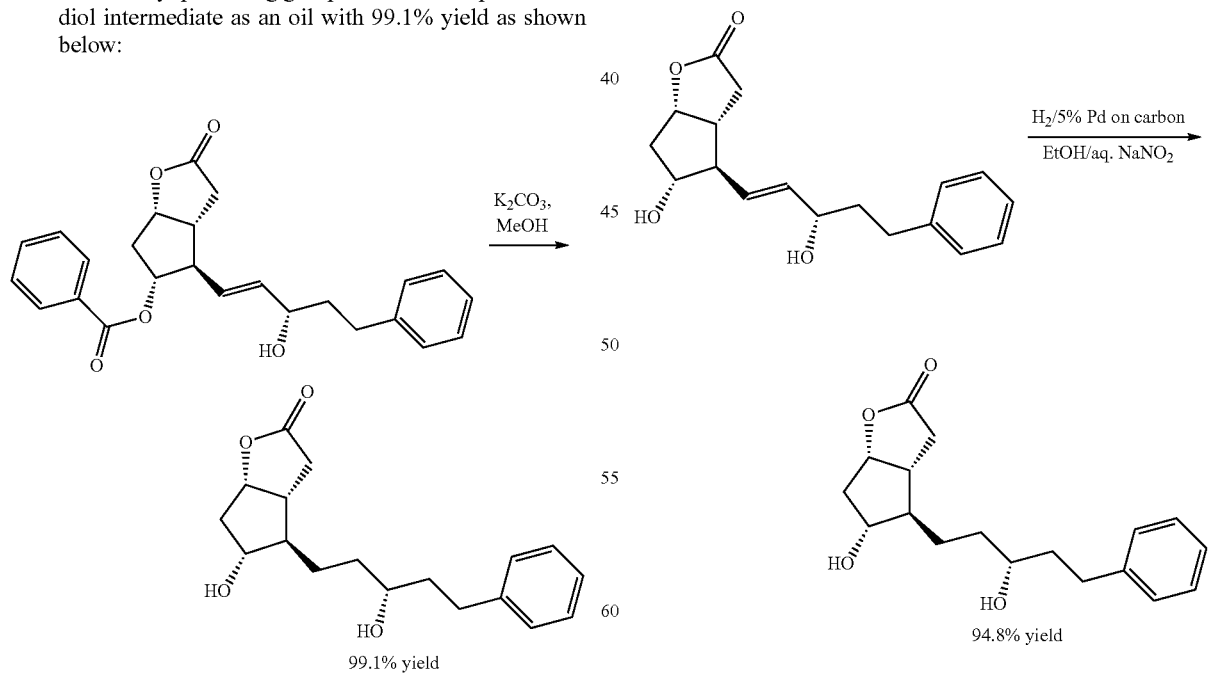

99.1% yield 94.8% yield

5. The α,β-unsaturated alcohol is subsequently hydrogenated to provide the saturated diol intermediate analog as an oil with 94.8% yield as illustrated below:

6. The diol is reacted with about two molar equivalents of triethylchlorosilane to provide the bis-triethylsilyl-protected intermediate as an oil with 97.6% yield as shown below:

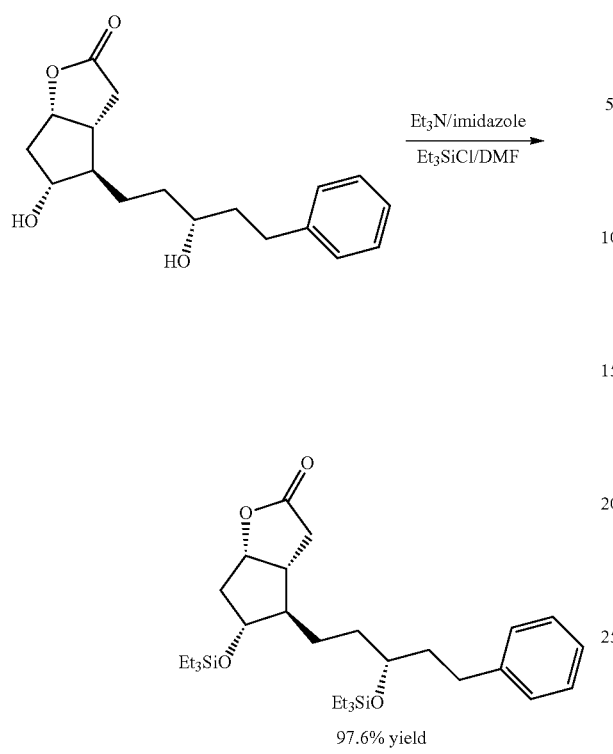

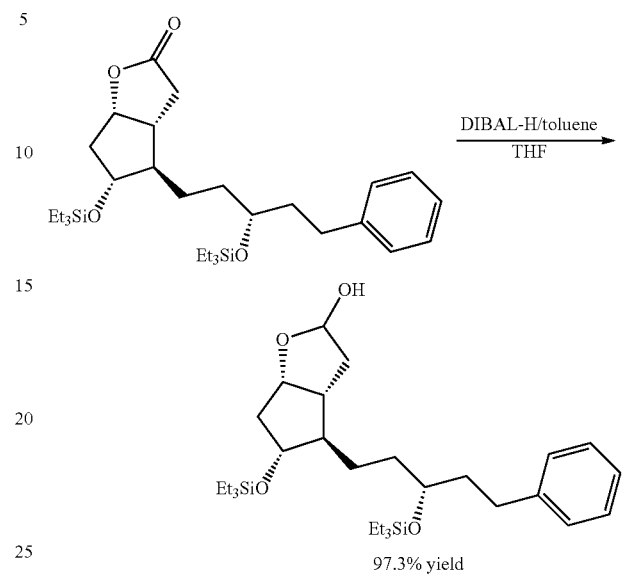

7. The lactone is subsequently reduced to provide the lactol as an oil with 97.3% yield:

97.3% yield

8. A Wittig reaction involving the lactol intermediate and (4-carboxybutyl)-triphenylphosphonium bromide provides the regioisomeric mixture of bis-triethylsilyl protected triol acids as a crude oil as depicted below:

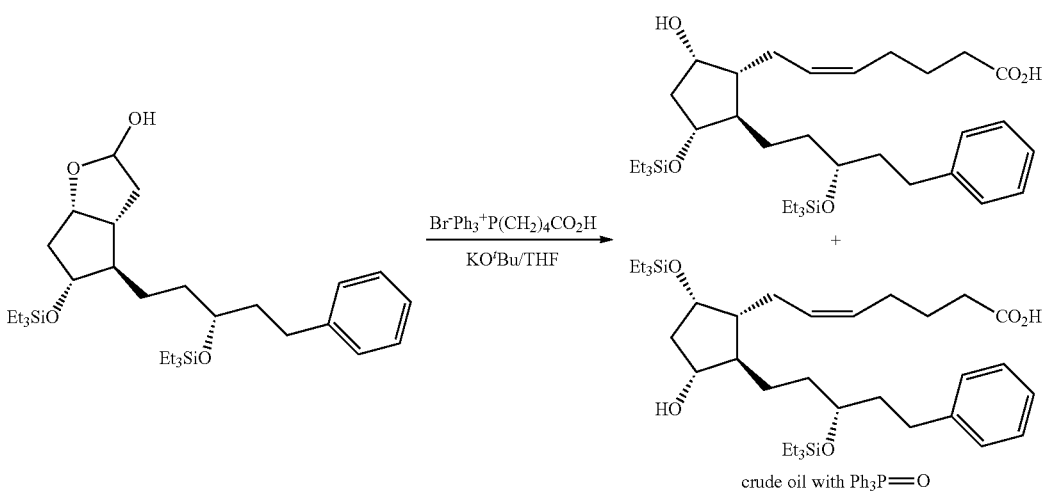

The crude oil product generally includes a mixture of both the cis and trans forms of the bis-silylated free acid intermediates. The trans forms are typically removed from the mixture by chromatography.

9. The regioisomeric mixture of carboxylic acids is esterified with 2-iodopropane to provide the corresponding mixture of isopropyl esters as an oil as shown below:

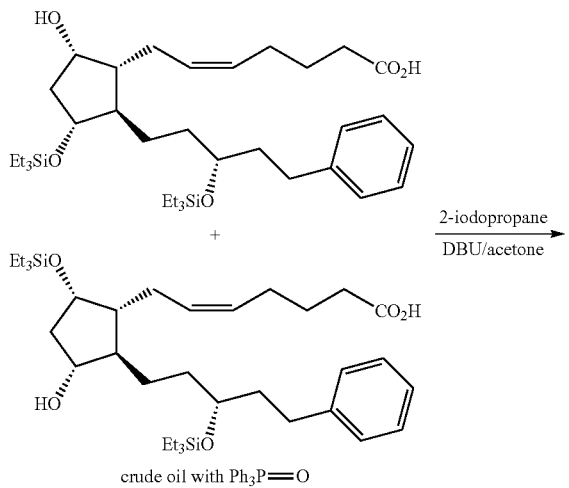

crude oil with Ph₃P=O

10. The ester mixture is reacted with triethylchlorosilane to provide a single tris-triethylsilyl-protected triol isopropyl ester as an oil with approximately 79% yield over three steps from the bis-triethylsilyl protected diol lactone intermediate as illustrated below:

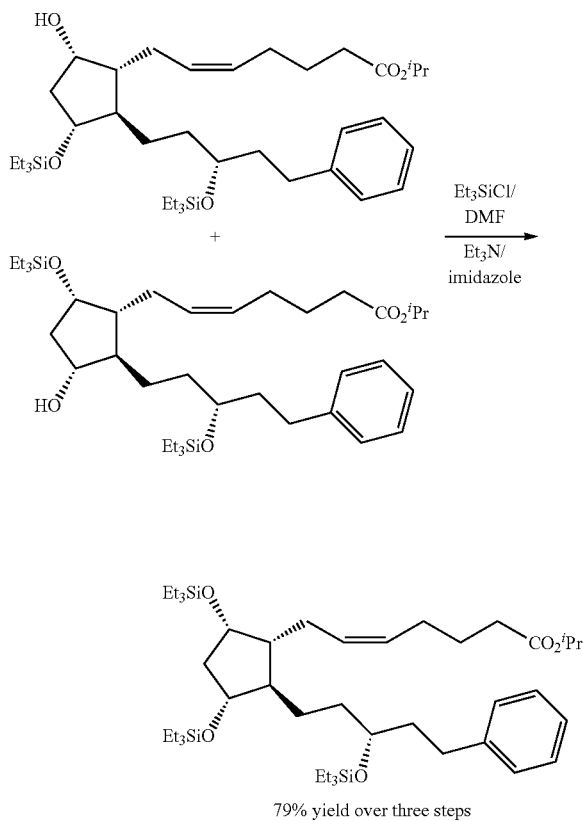

79% yield over three steps

11. The tris-triethylsilylated intermediate is deprotected with a catalytic amount of pyridinium-p-toluenesulfonate and the product is subsequently purified by preparative HPLC to provide latanoprost as an oil with an 18.7% yield over the eleven steps:

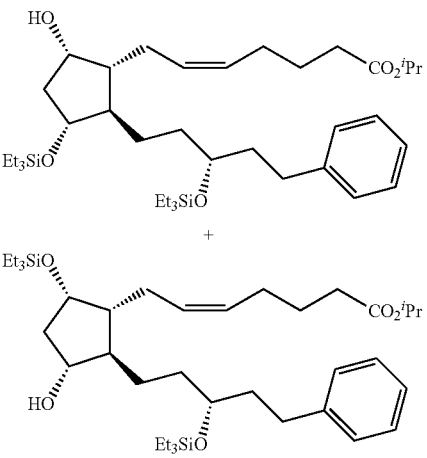

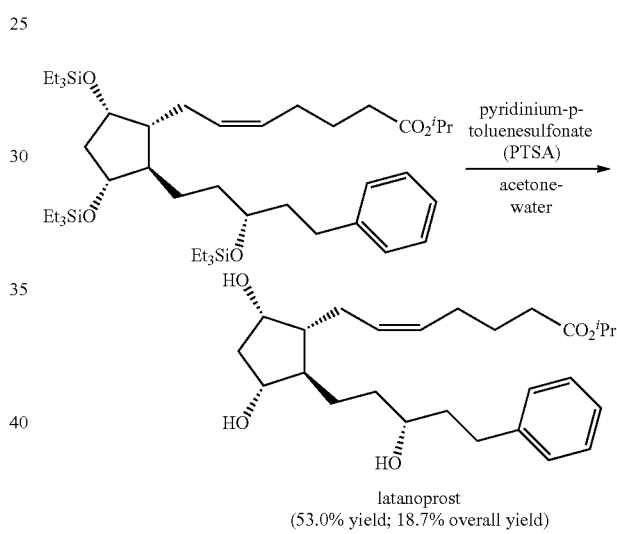

latanoprost
(53.0% yield; 18.7% overall yield)

The process from U.S. Pat. No. 7,268,239 described above involves both a crystallization and silica chromatography in step 3 to separate the epimers formed in the reduction reaction. The disclosure presents a medium pressure liquid chromatography (MPLC) method that can purify multiple injections of impure product without having to repack the column, a method that minimizes quantities of both stationary phase and eluent deployed to carry out product purification versus the traditional method of running a single injection through a packed silica column.

In view of the problems associated with prior art processes, it is highly desirable to provide an alternative process for the synthesis of latanoprost and related $PGF_{2\alpha}$ analogs and salts thereof. It is also highly desirable to provide synthetic intermediates that can be purified with greater ease and efficiency.

SUMMARY OF THE INVENTION

The exemplary embodiments may be directed to highly pure solid compounds of structural formulas (1) or (2), where $R^1$ is defined herein:

(1)

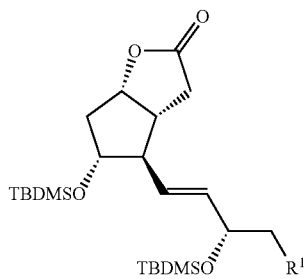

(2)

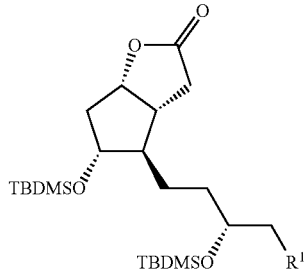

The exemplary embodiments may also be directed to methods of making, purifying, and isolating solid compounds of formulas (1) and (2).

The exemplary embodiments may also be directed to the use of highly pure solid compounds of formulas (1) and (2) as synthetic intermediates to the preparation of highly pure prostaglandin analogs.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

DETAILED DESCRIPTION OF THE INVENTION

The exemplary embodiments described herein may be based on the discovery that synthetic intermediate lactone compounds of formulas (1) and (2) may exist as solids. Compounds of formulas (1) and (2), except where tert-butyldimethylsilyl (TBDMS) groups as shown are replaced with other silyl groups, such as triisopropylsilyl (TIPS) and tert-butyldiphenylsilyl (TBDPS), are oils and do not solidify under experimental conditions described herein.

The exemplary embodiments may be directed to highly pure solid compounds of structural formulas (1) or (2), respectively, their formation, and their subsequent use as synthetic intermediates for preparing highly pure prostaglandin analogs.

The compounds of formulas (1) and (2), according to the exemplary embodiments, are shown below:

(1)

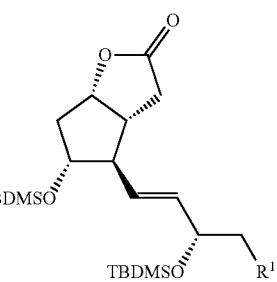

(2)

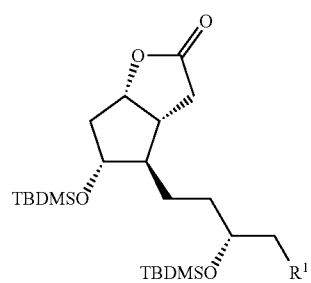

wherein:

$R^1$ is

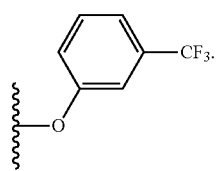 [SMILES: *Oc1cccc(C(F)(F)F)c1]

$Y$ is $CH_2$, O, S, or NH, and $X^1$, $X^2$, $X^3$, $X^4$, and $X^5$ are independently hydrogen, halo, trifluoromethyl, hydroxy, trifluoromethoxy, $(C_1$-$C_3)$-alkyl, $(C_1$-$C_3)$-alkoxy, or $(C_1$-$C_3)$-alkylthio.

Another exemplary embodiment may be directed to a compound of formula (1) or (2), wherein $R^1$ is —$CH_2Ph$ (benzyl), wherein Ph represents phenyl.

Another exemplary embodiment may be directed to a compound of formula (1), wherein $R^1$ is Another exemplary embodiment may be directed to a compound of formula (1), wherein $R^1$ is
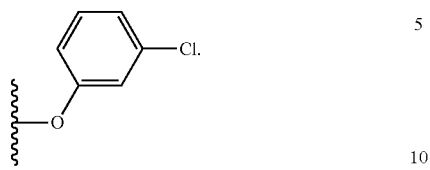
(5)
Another exemplary embodiment may be directed to a method of making highly pure forms of a compound of formula (1) or (2) from a compound according to either formula (C1) or (C2) as illustrated in Scheme 1 and described below.
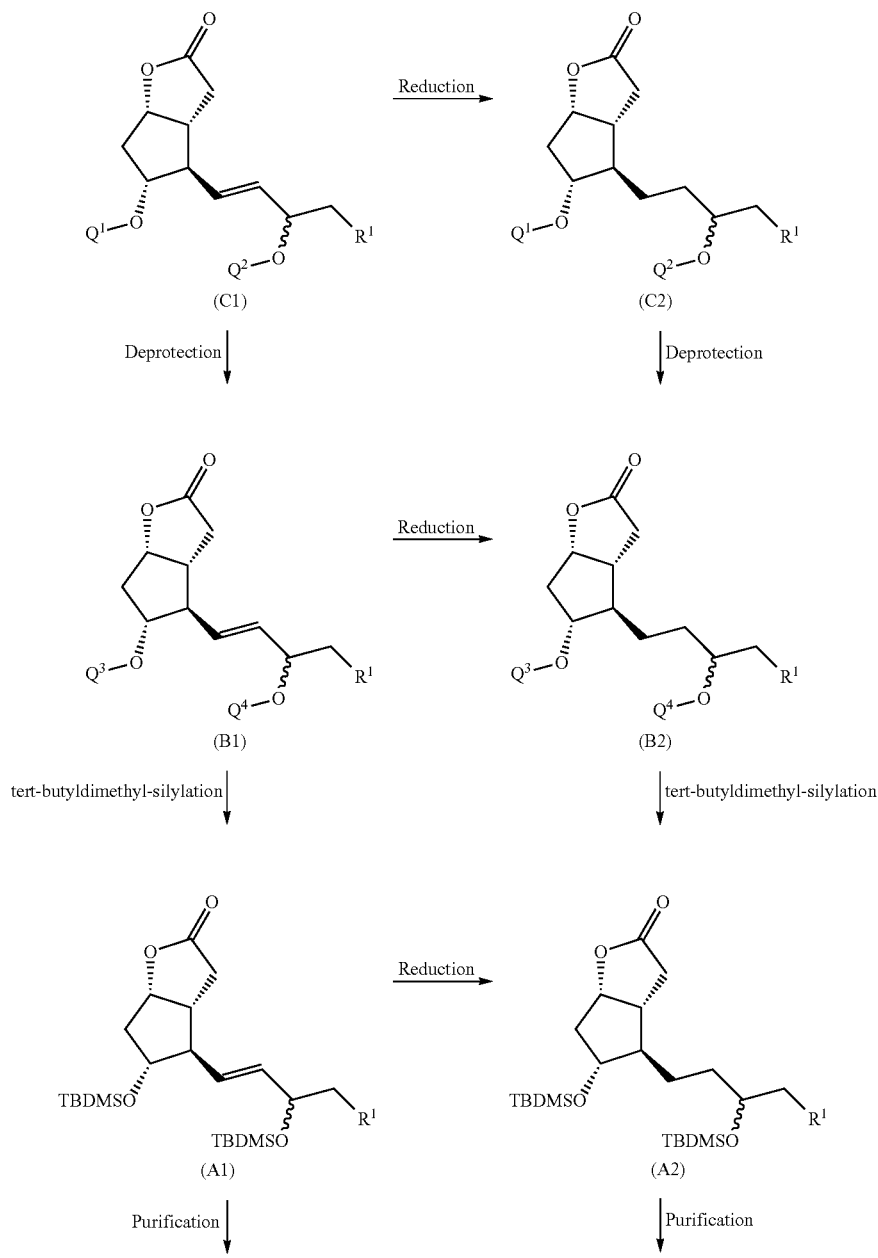

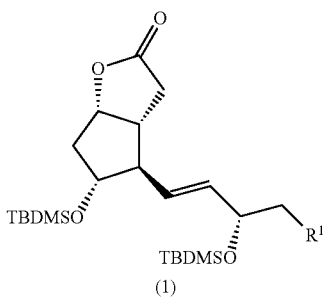

-continued

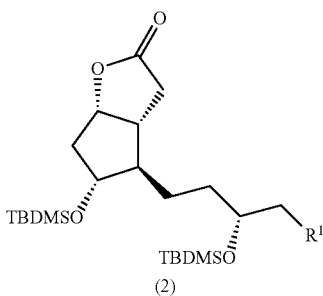

wherein:

R[1] is

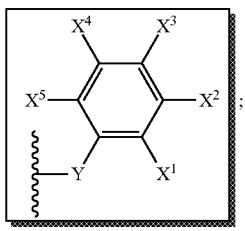

Y is $CH_2$, O, S, or NH;

$X^1$, $X^2$, $X^3$, $X^4$, and $X^5$ are independently hydrogen, halo, trifluoromethyl, hydroxy, trifluoromethoxy, ($C_1$-$C_3$)-alkyl, ($C_1$-$C_3$)-alkoxy, or ($C_1$-$C_3$)-alkylthio;

each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS; and each $Q^3$ and $Q^4$ is hydrogen; or wherein one of $Q^3$ and $Q^4$ is TBDMS and the other is hydrogen.

As shown in Scheme 1, the process begins by providing a stereoisomeric mixture of structural formula (C1), or the stereoisomeric mixture of structural formula (C2) (which is the reduced form of the compound of structural formula (C1)), wherein $R^1$, $Q^1$ and $Q^2$ are defined herein, by previously described methods, such as those described in WO 93/00329, European Patent No. EP 0 544 899 B1, U.S. Pat. No. 6,689, 901, U.S. Pat. No. 6,927,300, and Resul, B., Stjernschantz, J., No, K., et al., *J. Med. Chem.*, 1993, 36, 243-248.

Next, the protecting groups for $Q^1$ and $Q^2$ that are not TBDMS are removed to transform the compound of structural formula (C1) to that of structural formula (B1) or to transform the compound of structural formula (C2) to that of structural formula (B2). The deprotection steps of Scheme 1 involve conditions appropriate for removing the protecting group or groups that are not TBDMS, and if one of $Q^1$ and $Q^2$ is TBDMS, the conditions that are used are not suitable for removing the TBDMS group over the same reaction time period. A number of methods employed for removal of functional groups that protect non-aromatic hydroxyl groups are discussed in *Protective Groups in Organic Synthesis*, Second Edition, by Theodora W. Greene and Peter G. M. Wuts, John Wiley and Sons, Inc., pp. 10-118.

Next, a tert-butyldimethylsilylation transforms the compounds of formulas (B1) and (B2), respectively, to the compounds of formulas (A1) and (A2), respectively. The tert-butyldimethylsilylation steps of Scheme 1 involve conditions that assure that the bis-hydroxylated or mono-TBDMS-mono-hydroxylated starting material (B1) or (B2) is transformed into the respective bis-TBDMS product (A1) or (A2). Exemplary embodiments of these steps are provided herein. Other tert-butyldimethylsilylation conditions that may be used are described in *Protective Groups in Organic Synthesis*, Second Edition, by Theodora W. Greene and Peter G. M. Wuts, John Wiley and Sons, Inc., pp. 77-80.

Finally, the products of formulas (A1) or (A2) are purified to form the respective compounds of formulas (1) or (2). Each purification step of Scheme 1 includes one or more solid precipitation procedures beginning with dissolving a ≥1:1 α-/β-OTBDMS (hereafter referring to the OTBDMS on the aliphatic chain) stereoisomeric mixture of compound (A1) or (A2), respectively, for enriching the product mixture of stereoisomers in the α-OTBDMS stereoisomer, illustrated as compounds (1) or (2).

An additional step in the process, resulting in a reduction of the double bond on the aliphatic chain extending off the cyclopentyl ring by the addition of elemental hydrogen ($H_2$), may occur at different points along the process of Scheme 1. Thus, this double bond reduction may be utilized to transform the compound of formula (C1) to (C2), or to transform the compound of formula (B1) to (B2), or to transform the compound of formula (A1) to (A2), or to transform the compound of formula (1) to (2), at the appropriate points in the process of Scheme 1.

The purification methods for transforming the products of formulas (A1) or (A2) to the respective compounds of formulas (1) or (2), in accordance with Scheme 1, are described in further detail below. These same purification methods may also be utilized to transform the products of formulas (A1) or (A2) to the respective compounds of formulas (1) or (2) without the use of Scheme 1, in other alternative embodiments. Moreover, the purification methods may also be utilized to further purify solid forms of the compounds of formulas (1) or (2) irrespective of Scheme 1 entirely, without the need for the transformation of the products of formula (A1) or (A2) to the respective compounds of formulas (1) or (2).

One exemplary method of making and isolating a purified form of a compound of formula (1) that utilizes solid precipitation includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii); and (v). Isolation of the solid precipitate of step (iv) by filtration.

Another exemplary embodiment may be directed to a method of making and isolating a purified form of a compound of formula (1) which utilizes multiple solid precipitations, and includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii);

(v). Isolation of the solid precipitate of step (iv) by filtration;

(vi). Dissolving the isolated solid of step (v) in an organic solvent to form an organic solution;

(vii). Addition of water to the organic solution of step (vi);

(viii). Precipitation of a solid form of material that is more enriched in the α-OTBDMS epimer (as illustrated by formula (1)) versus the β-OTBDMS epimer than the material isolated in step (v); and (ix). Isolation of the solid precipitate of step (viii) by filtration.

Still another exemplary embodiment may be directed to a method of making and isolating a purified form of a compound of formula (2) that utilizes multiple solid precipitations includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii);

(v). Isolation of the solid precipitate of step (iv) by filtration;

(vi). Reducing the carbon-carbon double bond of the compound of formula (1) isolated in step (v) by the addition of elemental hydrogen ($H_2$) or an equivalent to a solution of the compound formula (1) provide the corresponding compound of formula (2);

(vii). Dissolving the reduced compound prepared in step (vi) in an organic solvent to form an organic solution;

(viii). Addition of water to the organic solution of step (vii);

(ix). Precipitation of a solid form of material that is more enriched in the α-OTBDMS epimer (as illustrated by formula (2)) versus the β-OTBDMS epimer than the material prepared in step (vi); and (x). Isolation of the solid precipitate of step (ix) by filtration.

Yet another exemplary embodiment may be directed to a method of making and isolating a purified form of a compound of formula (2) that utilizes multiple solid precipitations and includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii);

(v). Isolation of the solid precipitate of step (iv) by filtration;

(vi). Dissolving the isolated solid of step (v) in an organic solvent to form an organic solution;

(vii). Addition of water to the organic solution of step (vi);

(viii). Precipitation of a solid form of material that is more enriched in the α-OTBDMS epimer (as illustrated by formula (1)) versus the β-OTBDMS epimer than the material prepared in step (v);

(ix). Isolation of the solid precipitate of step (viii) by filtration (x). Reducing the carbon-carbon double bond of the compound of formula (1) isolated in step (ix) by the addition of elemental hydrogen ($H_2$) or an equivalent to a solution of the compound of formula (1) provide the corresponding compound of formula (2);

(xi). Dissolving the isolated solid of step (x) in an organic solvent to form an organic solution;

(xii). Addition of water to the organic solution of step (xi);

(xiii). Precipitation of a solid form of material that is more enriched in the α-OTBDMS epimer (as illustrated by formula (2)) versus the β-OTBDMS epimer than the material prepared in step (x); and (xiv). Isolation of the solid precipitate of step (xiii) by filtration.

Another exemplary embodiment may be directed to a method of making and isolating a purified form of a compound of formula (2) that utilizes multiple solid precipitations and includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii);

(v). Isolation of the solid precipitate of step (iv) by filtration;

(vi). Reducing the carbon-carbon double bond of the compound of formula (1) isolated in step (v) by the addition of elemental hydrogen ($H_2$) or an equivalent to a solution of the compound of formula (1) provide the corresponding compound of formula (2);

(vii). Dissolving the isolated solid of step (vi) in an organic solvent to form an organic solution;

(viii). Addition of water to the organic solution of step (vii);

(ix). Precipitation of a solid form of material that is more enriched in the α-OTBDMS epimer (as illustrated by formula (2)) versus the β-OTBDMS epimer than the material prepared in step (vi);

(x). Isolation of the solid precipitate of step (ix) by filtration (xi). Dissolving the isolated solid of step (x) in an organic solvent to form an organic solution;

(xii). Addition of water to the organic solution of step (xi);

(xiii). Precipitation of a solid form of material that is more enriched in the α-OTBDMS epimer (as illustrated by formula (1)) versus the β-OTBDMS epimer than the material prepared in step (x); and (xiv). Isolation of the solid precipitate of step (xiii) by filtration.

Another exemplary embodiment may be directed to a method of making and isolating a purified form of a compound of formula (2) that utilizes multiple solid precipitations and includes the following steps:

(i). Preparing the material of formula (A1), wherein the product mixture contains either equal amounts of both α-OTBDMS and β-OTBDMS epimers or predominantly the α-OTBDMS epimer;

(ii). Dissolving the product mixture of step (i) in an organic solvent to form an organic solution;

(iii). Addition of water to the organic solution of step (ii);

(iv). Precipitation of a solid form of material that is more enriched in the α-OTBDMS epimer (as illustrated by formula (1)) versus the β-OTBDMS epimer than the starting material (A1) prepared in step (i) from the aquified organic solution of step (iii);

(v). Isolation of the solid precipitate of step (iv) by filtration;

(vi). Dissolving the isolated solid of step (v) in an organic solvent to form an organic solution;

(vii). Addition of water to the organic solution of step (vi);

(viii). Precipitation of a solid form of material that is more enriched in the α-OTBDMS epimer (as illustrated by formula (1)) versus the β-OTBDMS epimer than the material prepared in step (v);

(ix). Isolation of the solid precipitate of step (viii) by filtration (x). Reducing the carbon-carbon double bond of the compound of formula (1) isolated in step (ix) by the addition of elemental hydrogen ($H_2$) or an equivalent to a solution of the compound of formula (1) to provide the corresponding compound of formula (2);

(xi). Dissolving the isolated solid of step (x) in an organic solvent to form an organic solution;

(xii). Addition of water to the organic solution of step (xi);

(xiii). Precipitation of a solid form of material that is more enriched in the α-OTBDMS epimer (as illustrated by formula (2)) versus the β-OTBDMS epimer than the material prepared in step (x);

(xiv). Isolation of the solid precipitate of step (xiii) by filtration;

(xv). Dissolving the isolated solid of step (xiv) in an organic solvent to form an organic solution;

(xvi). Addition of water to the organic solution of step (xv);

(xvii). Precipitation of a solid form of material that is more enriched in the α-OTBDMS epimer (as illustrated by formula (2)) versus the β-OTBDMS epimer than the material prepared in step (xiv); and (xviii). Isolation of the solid precipitate of step (xvii) by filtration.

Exemplary uses of highly pure solid compounds of structural formula (1) or (2), respectively as synthetic intermediates to the preparation of prostaglandin analogs of structural formulas (5) or (6), respectively, may be described according to Scheme 2:

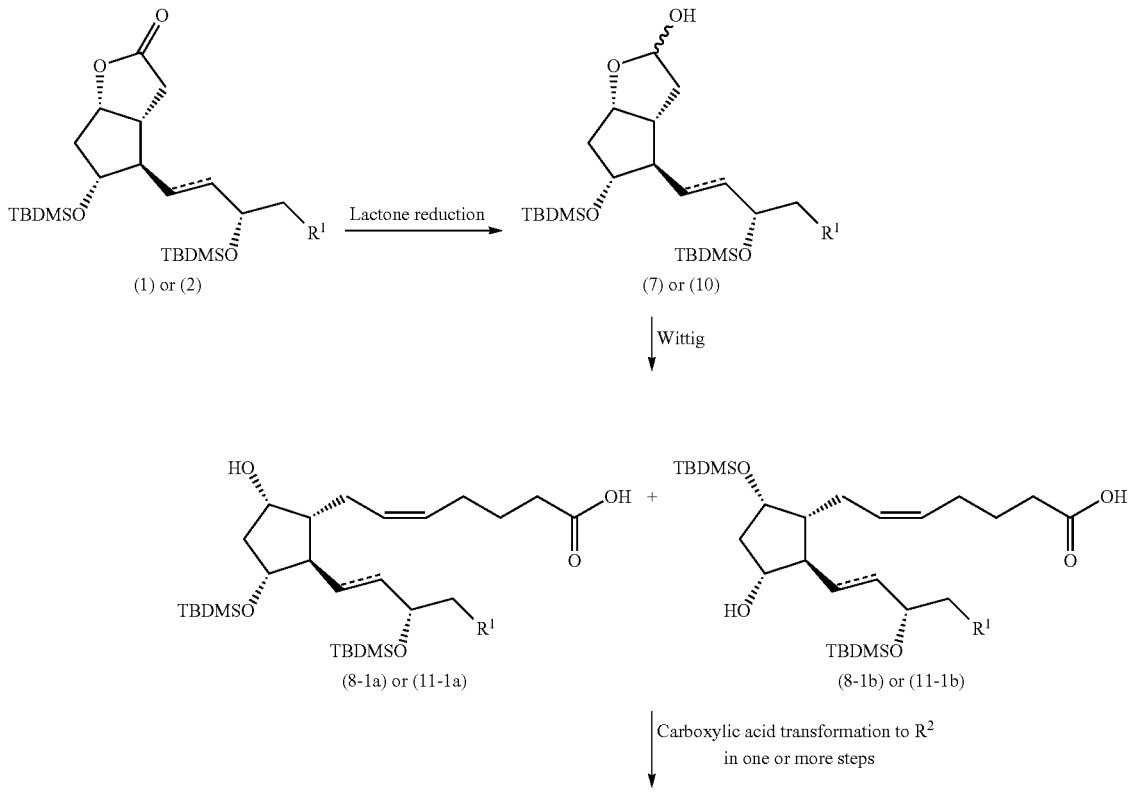

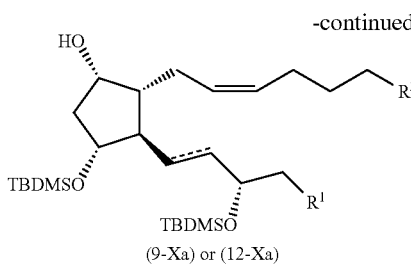

(9-Xa) or (12-Xa)

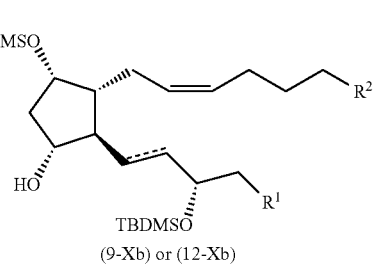

(9-Xb) or (12-Xb)

Deprotection

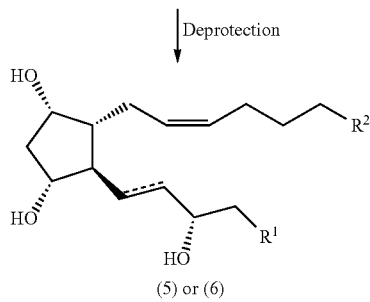

(5) or (6)

X is 1, 2, 3, ...
This suffix identifies $R^2$;
for example:
1 means $R^2 = CO_2H$,
2 means $R^2 = CONHEt$,
3 means $R^2 = CO_2{}^iPr$, etc., wherein:
$R^1$ is defined as above;
$R^2$ is $-CO_2R^3$, $-CONR^4R^5$, $-C(O)R^3$, $-C(O)CH_2X^6$, or $-CH_2X^6$;
$X^6$ is halo or $-OR^3$
$R^3$ is hydrogen, $(C_1-C_6)$-alkyl, or $-(CH_2)_n$-phenyl,
$R^4$ and $R^5$ are independently hydrogen, $(C_1-C_6)$-alkyl, or $-(CH_2)_n$-phenyl;
n is 0, 1, or 2;
⁓ represents a carbon-carbon single or double bond; and any phenyl of $R^3$, $R^4$ or $R^5$ may be optionally substituted with one or more of any one or combination of halo, trifluoromethyl, hydroxy, trifluoromethoxy, amino, cyano, $(C_1-C_6)$-alkyl, $(C_1-C_6)$-alkoxy, or $(C_1-C_6)$-alkylthio.

The process of Scheme 2 begins with a lactone reduction of (1) or (2), typically with a reducing agent such as diisobutylaluminum hydride (DIBAL-H), that provides lactol intermediates of structural formula (7) or (10), respectively. Lactol intermediate (7) or (10) may then be reacted with (4-carboxybutyl)triphenylphosphonium bromide in the presence of an excess base, such as sodium hexamethyldisilazide (NaHMDS, also called sodium bis(trimethylsilyl)amide) to afford, with cis-selectivity, free acid mixtures that contain predominantly (8-1a)/(8-1b) or (11-1a)/(11-1b), respectively. The free acid mixtures (8-1a)/(8-1b) or (11-1a)/(11-1b) may then be treated chemically using known methods in one or more steps to convert the carboxylic acid moiety to other functional groups $R^2$, as defined herein, and as described by the exemplary embodiments to provide mixtures (9-Xa)/(9-Xb) or (12-Xa)/(12-Xb), respectively. Finally, deprotection of intermediate mixture (9-Xa)/(9-Xb) or (12-Xa)/(12-Xb) provides prostaglandin $F_{2\alpha}$ analogs of structural formula (5) or (6), respectively. Examples of deprotection conditions employed to remove the TBDMS protecting groups may include the use of a desilylation reagent, preferably tetrabutylammonium fluoride (TBAF) or aqueous hydrochloric acid, mixed with an organic solvent, preferably tetrahydrofuran (THF) or isopropanol (IPA), respectively. The use of aqueous hydrochloric acid at room temperature generally provides a more efficient workup and purification of the deprotection reaction over the use of TBAF in THF.

Another related exemplary embodiment to Scheme 2 involves the deprotection of a mixture (8-1a)/(8-1b) or (11-1a)/(11-1b) to provide a free acid prostaglandin analog of structural formula (5) or (6), respectively, wherein $R^2$ is $CO_2H$.

Still another related exemplary embodiment involves the use of NaHMDS as the base in the Wittig step of Scheme 2. Use of excess NaHMDS provides more favorable cis-selectivity than the use of several other bases that may be used, including lithium hexamethyldisilazide (LiHMDS) and potassium tert-butoxide (KO$^t$Bu). Another advantage of using NaHMDS as the base is the removal of a tedious chromatography step, which is typically employed to remove quantities of trans-isomers. The use of NaHMDS as the base in the Wittig step of Scheme 2, or in a Wittig step that accomplishes the equivalent purpose of installing the prostaglandin α-chain that is not illustrated in Scheme 2, facilitates high overall chemical purity of compounds of formulas (5) and (6) of the exemplary embodiments, as will further be detailed in the examples provided below.

Yet another related exemplary embodiment involves the order of the last two steps illustrated in Scheme 2. It is an advantage of the exemplary embodiments to convert the carboxylic acid moiety of a (8-1a)/(8-1b) or (11-1a)/(11-1b) mixture to an $R^2$ moiety of a (9-Xa)/(9-Xb) or (12-Xa)/(12-Xb) mixture, wherein $R^2$ is as defined herein, followed by TBDMS deprotection according to methods described herein. This order of reaction steps provides an advantage over the reverse order, which is the order of reaction steps employed for various similar synthetic pathways disclosed in the art, because carboxylic acid conversion to $R^2$ groups as defined herein generally proceeds with lower risk of side reactions arising from the presence of multiple unprotected hydroxyl groups.

One specific exemplary embodiment of Scheme 2 may be directed to the use of a highly pure solid compound of structural formula (1a) or (2a) as a synthetic intermediate to the preparation of prostaglandin analog compounds of structural formula (5a) or (6a), respectively:

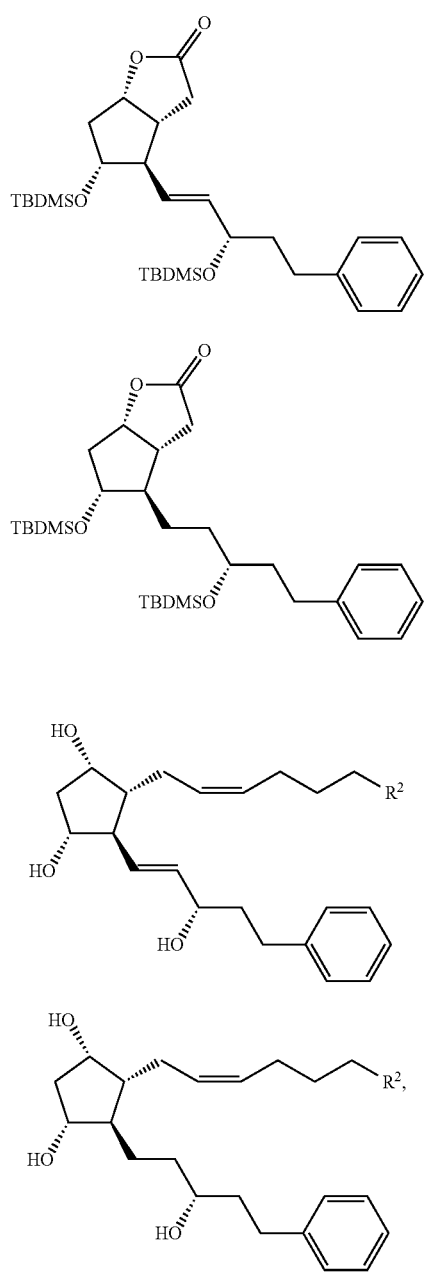

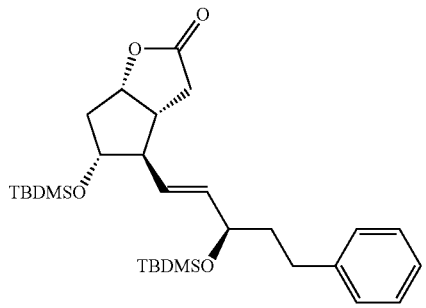

Compound (1a) may be separated from impurities, such as its epimer compound (Epi-1a), by solid precipitation to be isolated in highly pure form such as described above with respect to Scheme 1. Other synthetic intermediates analogous to Compound (1a) in which silyl protecting groups other than tert-butyldimethylsilyl (TBDMS), such as triisopropylsilyl (TIPS) or tert-butyldiphenylsilyl (TBDPS), take the place of the TBDMS protecting groups, are oils and thus may not be purified by solid precipitation. The crystallinity of Compound (1a) allows it to be separated from its impurities without the need of column chromatography. The obviation of chromatography at this stage of the synthesis of both latanoprost, bimatoprost, and their derivatives provides an improvement in manufacturing efficiency.

Compound (2a) may be prepared by reduction of the carbon-carbon double bond of compound (1a) by known methods such as catalytic hydrogenation. Compound (2a) is also crystalline and may be separated from impurities, such as its epimer compound (Epi-2a) (shown below), by solid precipitation, whereas synthetic intermediates analogous to compound 2a, in which other silyl groups take the place of the TBDMS protecting groups, are oils. Compound 2a may be used in the stereoselective syntheses of PGF$_{2\alpha}$ analogs; for example, latanoprost free acid and its ester and amide derivatives.

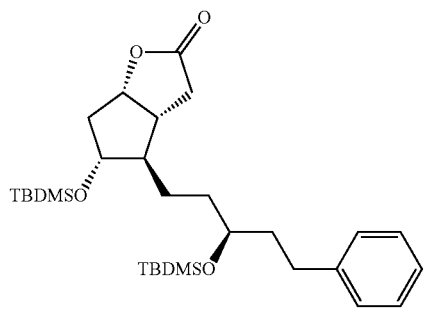

The use of the TBDMS protecting group may also be applied to the synthesis of other PGF$_{2\alpha}$ analogs and homologs, such as substituted analogs of bimatoprost and latanoprost, wherein the phenyl ring is substituted with one or more of one or a combination of halo, trifluoromethyl, hydroxy, trifluoromethoxy, (C$_1$-C$_3$)-alkyl, (C$_1$-C$_3$)-alkoxy, or (C$_1$-C$_3$)-alkylthio by way of crystalline bis-TBDMS-protected intermediates of general formula (1) or (2), respectively. The use of the TBDMS protecting group may further be applied to the synthesis of fluprostenol, substituted analogs of fluprostenol, cloprostenol, or substituted analogs of clo- Compound (1a) may be used in the stereoselective syntheses of PGF$_{2\alpha}$ analogs; for example, latanoprost free acid and its ester and amide derivatives, and bimatoprost free acid and its ester and amide derivatives. Compound (1a) may be synthesized as part of a mixture further comprising Compound (Epi-1a):

prostenol, by way of crystalline bis-TBDMS-protected intermediates of general formula (1).

The exemplary embodiments may also be directed to a process for the formation of compound (1a) (or its analogs as described above) from an unprotected diol precursor intermediate by bis-silylation. The exemplary embodiments may further be directed to a process of purifying and isolating the compound, including at least one solid precipitation of compound (1a) (or its analogs as described above). The exemplary embodiments may also be directed toward the use of purified compound (1a) (or its analogs described above) in the manufacture of useful $PGF_{2\alpha}$ analogs. The advantages over current state-of-the-art processes are as follows:

1. The synthesis and isolation of intermediates to $PGF_{2\alpha}$ analogs that are solids. A solid allows for more purification, storage, and handling options over a liquid or oil.
2. The purification of solid intermediates to $PGF_{2\alpha}$ analogs in order to avoid chromatography in the isolation of the highly pure stereoisomers. The elimination of chromatography improves efficiency, lowers costs, and minimizes waste streams.
3. The use of the highly stereochemically enriched intermediates for the synthesis of biologically active or therapeutically useful $PGF_{2\alpha}$ analogs allows for less-rigorous purification of later intermediates or final compounds, which may result in higher overall yields of desired products.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and chemical engineering described herein are those well known and commonly used in the art.

The term "alkyl," alone or in combination, means an acyclic radical, linear or branched, preferably containing from 1 to about 6 carbon atoms. Examples of such radicals include methyl, ethyl, n-propyl, isopropyl, n-butyl, isobutyl, sec-butyl, tert-butyl, pentyl, iso-amyl, hexyl, and the like. Where no specific substitution is specified, alkyl radicals may be optionally substituted with groups consisting of hydroxy, sulfhydryl, methoxy, ethoxy, amino, cyano, chloro, and fluoro. Examples of such substituted alkyl radicals include chloroethyl, hydroxyethyl, cyanobutyl, aminopentyl and the like.

The carbon atom content of various hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, '($C_1$-$C_6$)-alkyl' refers to alkyl of one to six carbon atoms, inclusive.

The terms "hydroxy" and "hydroxyl," as used herein, mean an OH radical.

The term "alkoxy" means a radical comprising an alkyl radical that is bonded to an oxygen atom, such as a methoxy radical. Preferred alkoxy radicals have one to about six carbon atoms. Examples of such radicals include methoxy, ethoxy, propoxy, isopropoxy, butoxy, and tert-butoxy.

The term "halo," as used herein, means one of the following group consisting of fluoro, chloro, bromo, or iodo.

The symbols

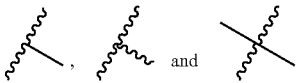

denote the point of attachment of a substituent.

The compounds of formula (1) or (2) may exist in a continuum of solid states ranging from fully amorphous to fully crystalline.

The compounds of formula (1) or (2) may also exist in a mesomorphic state (mesophase or liquid crystal) when subjected to suitable conditions. The mesomorphic state is intermediate between the true crystalline state and the true liquid state (either melt or solution).

Also, included herein are all polymorphs and crystal habits of compounds of formula (1) or (2), and isotopically-labeled forms thereof.

As used herein, the term "precipitate" refers to a substance existing in any of a continuum of solid states ranging from fully amorphous to fully crystalline that forms out of a mixture such as, but not limited to, a solution, suspension, emulsion, or microemulsion.

As used herein, the term "precipitation" refers to a purification process by which a precipitate forms or may be caused to form out of a solution, suspension, emulsion, or microemulsion. A precipitate may be caused to form out of a mixture such as, but not limited to, a solution, suspension, emulsion, or microemulsion by techniques known to those ordinarily skilled in the art. Such methods include, but are not limited to, standing over time, cooling, warming, addition of a cosolvent, agitation (such as, but not limited to scratching, stirring, or sonication), concentration of the mixture (for example, by evaporation), or seeding.

As used herein, the term "amorphous" refers to a solid material whose constituent particles or molecules possess no long-range order or repeating pattern in space.

As used herein, the term "crystal" or "crystalline solid" refers to a solid material whose constituent particles or molecules are arranged in an orderly repeating pattern extending in all three spatial dimensions. The compounds of formula (1) or (2) may exist in one or more crystalline forms, or polymorphs. A crystalline precipitate of a compound of formula (1) or (2) may exist in a single, homogenous crystalline form or in a mixture of crystalline forms, or a mixture of at least on crystalline form and at least one amorphous form.

As used herein, the term "crystallization" refers to a type of precipitation in which the precipitate is a full or partial crystalline solid. The crystalline solid precipitated may be a single crystal form, a mixture of crystal forms, or a mixture of at least one crystal form and at least one amorphous form.

As used herein, the term "recrystallization" refers to a type of crystallization in which the starting material (to be purified) is a fully or partially crystalline solid.

One solid form of a compound of formula (1) or (2) may be transformed into another solid form by subjection to varying conditions of, for example, temperature or pressure.

The above description of exemplary embodiments, and examples provided below, are merely exemplary in nature and, thus, variations thereof are not to be regarded as a departure from the spirit and scope of the invention.

EXAMPLES

The Examples provided herein describe exemplary methods for forming the solid synthetic intermediate compounds related to either compound (1) or (2), or derivatives thereof, and to their subsequent use for preparing highly pure prostaglandin analogs.

Mass spectra (MS) were obtained using a Finnigan MAT LCQ mass spectrometer (classic, serial number is LC000930).

Nuclear magnetic resonance (NMR) spectra were obtained using a Bruker (300 MHz), Varian INOVA (400 MHz), or a Varian INOVA (500 MHz) nuclear magnetic resonance spectrometer.

High performance liquid chromatography (HPLC) analytical separations were performed on an Agilent 1100 HPLC and followed by an Agilent Technologies G1315B Diode Array Detector with UV$_{max}$ @ 633 nm.

Example 1

Preparation of (3aR,4R,5R,6aS)-5-(tert-butyldimethylsilyloxy)-4-(S,E)-3-(tert-butyldimethylsilyloxy)-5-phenylpent-1-enyl)hexahydro-2H-cyclopenta[b]furan-2-one (Lactone Bis-TBDMS-protected Diol Compound (1a)

Step A: Preparation of mixture comprising (3aR,4R,5R,6aS)-4-(S,E)-3-hydroxy-5-phenylpent-1-enyl)-2-oxohexahydro-2H-cyclopenta[b]furan-5-yl biphenyl-4-carboxylate (3a) and (3aR,4R,5R,6aS)-4-((R,E)-3-hydroxy-5-phenylpent-1-enyl)-2-oxohexahydro-2H-cyclopenta[b]furan-5-yl biphenyl-4-carboxylate (Epi-3a)

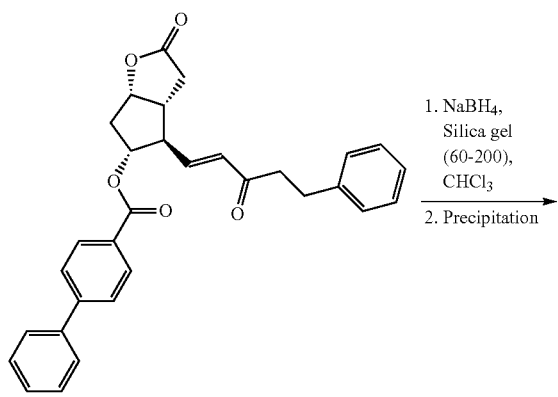

1. NaBH$_4$, Silica gel (60-200), CHCl$_3$
2. Precipitation

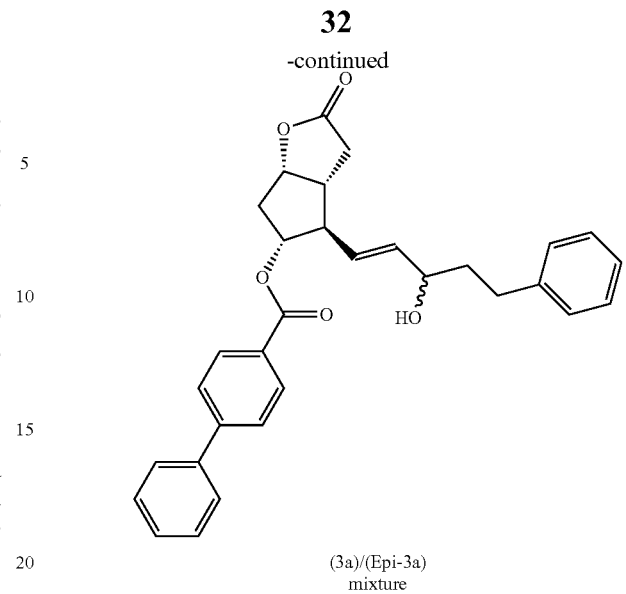

(3a)/(Epi-3a) mixture

To a round-bottom flask fitted with a thermocouple was charged (3aR,4R,5R,6aS)-2-oxo-4-((E)-3-oxo-5-phenylpent-1-enyl)hexahydro-2H-cyclopenta[b]furan-5-yl biphenyl-4-carboxylate (1.13 g, 2.35 mmol, 1.0 molar equivalent) and silica gel (1.5 g, with particle size 60-200 μm) in chloroform (10 mL, 8.8 volumes). The mixture was stirred vigorously. Sodium borohydride (0.114 g, 3.0 mmol, 1.27 molar equivalents) was dissolved in deionized water (0.22 mL) and added slowly to the reaction mixture. The reaction mixture was stirred at room temperature for one hour. The reaction mixture was cooled to 0° C., and the excess reducing reagent was reacted with 3 M aqueous hydrochloric acid (HCl) solution (1 mL). The reaction mixture was stirred for five minutes. Methanol (2 mL) was added and stirring continued for another five minutes. The silica gel was removed by filtration and washed twice with 3 mL of chloroform-methanol mixture of 5:1 volume ratio. The filtrate was diluted with ethyl acetate to a total volume of 25 mL. The filtrate was concentrated in vacuo (20-25 mmHg, bath at 30-35° C.) to provide a pasty white foam-solid residue (1.2 g); HPLC-UV (3a)/(Epi-3a) ratio is about 7:3.

The (3a)/(Epi-3a) mixture residue was mixed with a solvent mixture consisting of methanol (6 volumes) and ethyl acetate (0.2 volume) and the resulting mixture was subsequently heated to 60° C. The resulting solution was allowed to cool to room temperatures while stirring overnight. A white solid had precipitated overnight and was collected by filtration, washed twice with methanol (2×1 volume), and suctioned to afford the title intermediate as a 83.5/16.5 (3a)/(Epi-3a) mixture. The filtrate contained a 47/53 (3a)/(Epi-3a) mixture.

This procedure was repeated except that 6.2 g of (3aR,4R,5R,6aS)-2-oxo-4-((E)-3-oxo-5-phenylpent-1-enyl)hexahydro-2H-cyclopenta[b]furan-5-yl biphenyl-4-carboxylate was used instead of 1.13 g to provide the title intermediate as a 55/45 (3a)/(Epi-3a) mixture.

The (3a)/(Epi-3a) mixture ratios provided here may be further enriched in (3a) by methods such as recrystallization (or multiple recrystallizations) or chromatography to remove the (Epi-3a) stereoisomer.

Step B: Preparation of mixture comprising (3aR,4R, 5R,6aS)-5-hydroxy-4-((S,E)-3-hydroxy-5-phenyl-pent-1-enyl)hexahydro-2H-cyclopenta[b]furan-2-one (Lactone Diol Compound (4a) and (3aR,4R,5R,6aS)-5-hydroxy-4-(R,E)-3-hydroxy-5-phenylpent-1-enyl) hexahydro-2H-cyclopenta[b]furan-2-one (Lactone Diol Compound (Epi-4-a)

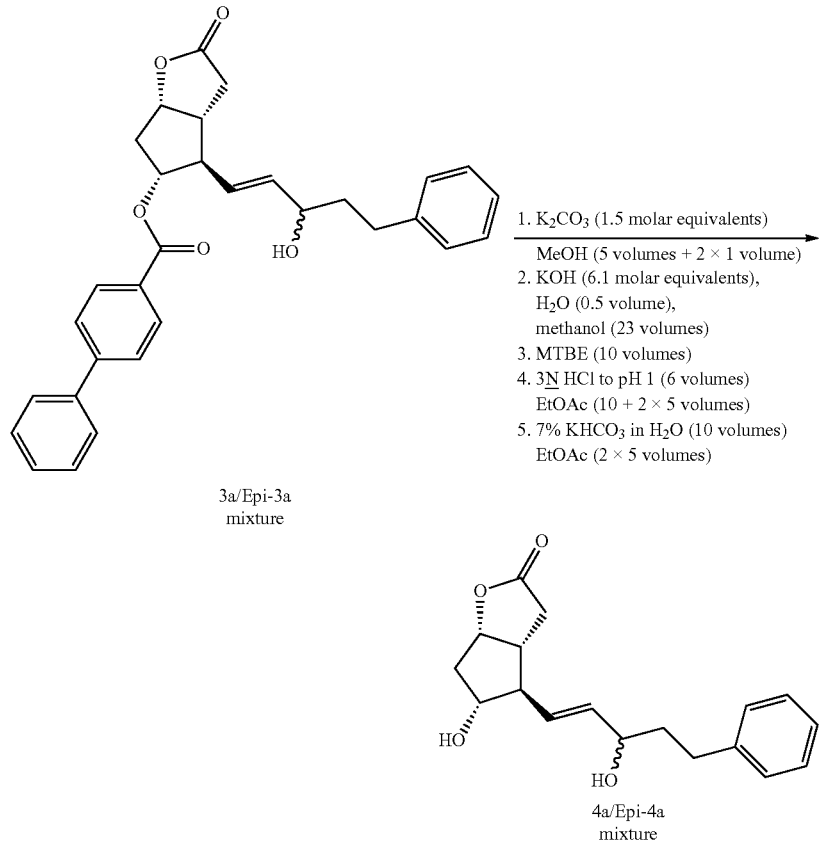

3a/Epi-3a mixture

1. $K_2CO_3$ (1.5 molar equivalents)
   MeOH (5 volumes + 2 × 1 volume)
2. KOH (6.1 molar equivalents),
   $H_2O$ (0.5 volume),
   methanol (23 volumes)
3. MTBE (10 volumes)
4. 3<u>N</u> HCl to pH 1 (6 volumes)
   EtOAc (10 + 2 × 5 volumes)
5. 7% $KHCO_3$ in $H_2O$ (10 volumes)
   EtOAc (2 × 5 volumes)

4a/Epi-4a mixture

To a three-necked flask fitted with a mechanical stirrer and thermocouple was charged material comprising (3aR,4R,5R,6aS)-4-((S,E)-3-hydroxy-5-phenylpent-1-enyl)-2-oxo-hexahydro-2H-cyclopenta[b]furan-5-yl biphenyl-4-carboxylate and (3aR,4R,5R,6aS)-4-((R,E)-3-hydroxy-5-phenylpent-1-enyl)-2-oxohexahydro-2H-cyclopenta[b]furan-5-yl biphenyl-4-carboxylate (3a)/(Epi-3a) mixture, 15 g, 31 mmol, 1.0 molar equivalent) dissolved in methanol (75 mL, 5 volumes). Potassium carbonate solid (6.44 g, 46.7 mmol, 1.5 molar equivalents) was added and the mixture was stirred at room temperature for no less than 15 hours. After completion of reaction as judged by thin layer chromatography (TLC), the solids in the reaction mixture were filtered on a medium porosity (10-16 μm) fritted funnel and rinsed with two 250-mL portions of methanol. The resulting filtrate was charged into a three-necked flask fitted with a mechanical stirrer and a thermocouple. The mixture was diluted with methanol (40 mL) and potassium hydroxide (12.22 g of 87.9% w/w pellets, 10.74 g of pure KOH, 192 mmol, 6 molar equivalents) was charged followed by water (7.5 mL, 0.5 volume). The mixture was stirred and a moderate exotherm from 23° C. to 31° C. was observed before subsiding. The mixture was stirred at room temperature for no less than 4 hours. After completion of reaction as judged by TLC, the mixture were filtered on a medium porosity (10-16 μm) fritted funnel and rinsed with two 10-mL portions of methanol. The filtrate was concentrated in vacuo (20-25 mmHg, bath at 30-35° C.) to a pasty, dark brown residue. The residue was dissolved in water (150 mL, 10 volumes) and methyl tert-butyl ether (MTBE, 70 mL, 4.7 volumes). The layers were separated and the upper organic layer was discarded. The lower aqueous layer was acidified to pH~1 with 3 M (Molar) aqueous hydrochloric acid (95 mL). The mixture was stirred at room temperature for no less than 4 hours. A dirty white solid formed at this point. The solid was dissolved by adding ethyl acetate (EtOAc, 150 mL, 10 volumes) and the layers were separated. The lower pH~1 aqueous layer was re-extracted with two 100-mL (6.7 volumes) portions of EtOAc. The combined, brown, upper organic layers were washed with 7% w/w aqueous potassium hydrogen carbonate (80 mL, 5.3 volumes). The lower aqueous layer had a dark brown color and a pH of 11. The layers were separated and the lower aqueous layer was re-extracted with two 80-mL (5.3 vol.) portions of EtOAc. The solvent was removed under reduced pressure. The water was chased with 5 volumes of toluene. The resulting solid was more than the expected yield. The reaction yield was assumed to be quantitative.

In certain instances, some solids (p-phenyl benzoic acid potassium salt) might be present at the layers interface preventing a clear view of the phase separation. If this occurs, the bulk of the lower aqueous layer would be drained and the remaining mixture (a small aqueous lower layer and the whole upper organic layer) would be filtered through a medium porosity (10-16 μm) fritted funnel. The layers of the resulting filtrate would then be separated.

Step C: Preparation of Lactone Bis-TBDMS-Protected Diol Compound Mixture (1a)/(Epi-1a)

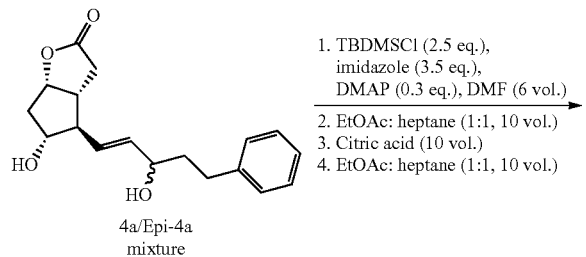

1. TBDMSCl (2.5 eq.), imidazole (3.5 eq.), DMAP (0.3 eq.), DMF (6 vol.)
2. EtOAc: heptane (1:1, 10 vol.)
3. Citric acid (10 vol.)
4. EtOAc: heptane (1:1, 10 vol.)

4a/Epi-4a mixture

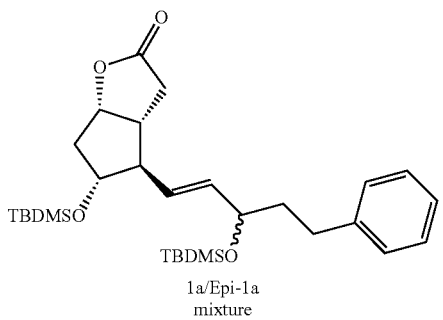

1a/Epi-1a mixture

To a three-necked flask fitted with a mechanical stirrer and thermocouple was charged lactone diol compound mixture (4a)/(Epi-4a) (9.4 g, 31 mmol, 1 molar equivalent) dissolved in N,N-dimethylformamide (DMF, 60 mL, 6.4 volumes). Tert-Butyldimethylsilyl chloride (TBDMSCl, 11.65 g, 77.30 mmol, 2.5 molar equivalents), imidazole (7.38 g, 108 mmol, 3.5 molar equivalents), and 4-dimethylaminopyridine (DMAP, 1.13 g, 9.2 mmol, 0.3 molar equivalent) were added and the mixture was stirred at room temperature for no less than 15 hours. After completion of reaction as judged by TLC, the reaction mixture was cooled to 0±5° C. The reaction mixture was subsequently diluted with ethyl acetate-heptane solution (1:1 v/v, 80 mL, 8.5 volumes). The mixture was acidified to pH~4 with 5% aqueous citric acid solution. The layers were separated. The aqueous phase was re-extracted with two portions of ethyl acetate-heptane solution (1:1 v/v, 80 mL, 8.5 volumes). The combined upper organic layers were combined and concentrated under reduced pressure to provide the crude compound mixture 1a/Epi-1a as a residue.

Steps D and E

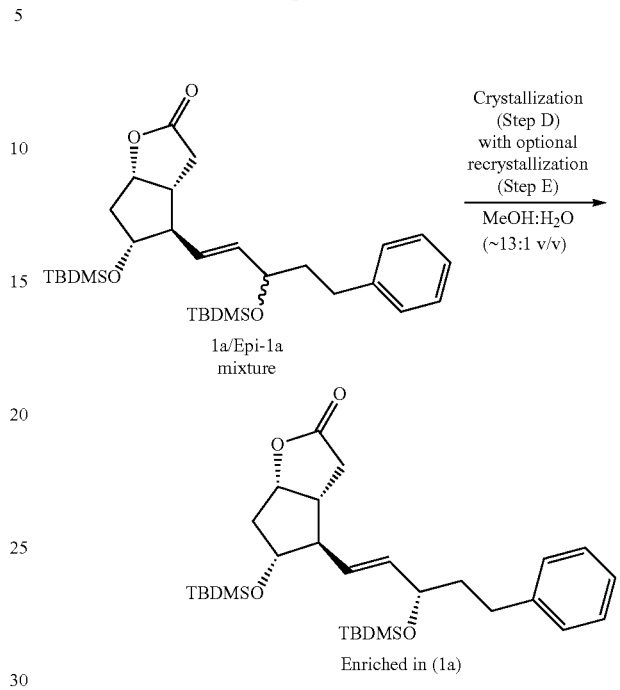

1a/Epi-1a mixture

Crystallization (Step D) with optional recrystallization (Step E)
MeOH:H₂O (~13:1 v/v)

Enriched in (1a)

Step D: Crystallization of Lactone Bis-TBDMS-Protected Diol Compound Mixture (1a)/(Epi-1a) to Provide Enantiomerically-Enriched Compound (1a)

The residue (crude compound mixture (1a)/(Epi-1a) prepared in Step C above) was dissolved in methanol (135 mL, 14.4 volumes) and charged to a 500-mL three-necked flask fitted with a mechanical stirrer and a thermocouple. The mixture was stirred at room temperature. Deionized water (10.5 mL, 1.1 volumes) was added slowly to the stirred solution. A white solid crystallized. The mixture was stirred at room temperature for no less than one hour. The mixture was cooled to 0±5° C. The white solid was filtered on a medium porosity (10-16 μm) fritted glass funnel, rinsed with three 15-mL portions of deionized water, collected, and dried under vacuum (5 mmHg, 45° C.) to afford the title compound (14.27 g, 86.5% recrystallization recovery, 85% overall yield) as a white solid; $^1$H-NMR (500 MHz; CDCl$_3$) d 7.31-7.27 (m, 2H), 7.22-7.16 (m, 3H), 5.58-5.53 (m, 1H), 5.46-5.40 (m, 1H), 4.99-4.94 (m, 1H), 4.17-4.12 (m, 1H), 4.03-3.98 (m, 1H), 2.81-2.73 (m, 1H), 2.72-2.57 (m, 3H), 2.51 (dd, 1H, J=18, 3 Hz), 2.50-2.45 (m, 1H), 2.28-2.22 (m, 1H), 2.03-1.98 (m, 1H), 1.88-1.74 (m, 2H); MS (ESI+) m/z 553.8 (M+Na+).

Step E: Recrystallization of Enantiomerically-Enriched Lactone Bis-TBDMS-Protected Diol Compound (1a)

Crystallized material from Step D above may be recrystallized by repeating the crystallization procedure described above in Step D to provide a solid compound further enriched in compound (1a).

The following table records 3a/Epi-3a and 1a/Epi-1a epimeric ratios of mixtures, which are provided as described by the procedures of Example 1, as determined by HPLC-UV. Relative absorbance between single entities of epimeric pairs is assumed to be equivalent.

| Trial # | 3a/Epi-3a ratio (starting mat.) Step B | 1a/Epi-1a ratio (crude) Step C | 1a/Epi-1a ratio (crystallized once) Step D | 1a/Epi-1a ratio (crystallized twice) Step E |
|---|---|---|---|---|
| 1 | 98.67/1.3 | 98.42/1.48 | 99.8/0.2 | >99.9/<0.1 |
| 2 | 92.91/7.09 | 96.27/3.73 | 99.14/0.85 | 99.79/0.21 |
| 3 | 99.49/0.5 | 99.68/0.319 | 99.9/0.077 | 99.97/0.03 |
| 4 | 97.49/2.51 | 96.75/3.245 | 98.98/1.02 | 99.32/0.68 |
| 5 | 96.03/3.97 | 92.52/7.48 | 97.11/2.89 | 99.19/0.81 |
| 6 | 85.08/14.91 | N/A | 92.08/7.92 | 98.5/1.5 |
| 7 | 98.9/1.1 | N/A | 99.5/0.5 | 99.8/0.2 |

Example 2

Preparation of (3aR,4R,5R,6aS)-5-(tert-butyldimethylsilyloxy)-4-(R)-3-(tert-butyldimethylsilyloxy)-5-phenylpentyl)hexahydro-2H-cyclopenta[b]furan-2-one (Lactone Bis-TBDMS-protected Diol Compound 2a)

Step A: Preparation of Lactone Bis-TBDMS-Protected Diol Compound Mixture 2a/Epi-2a

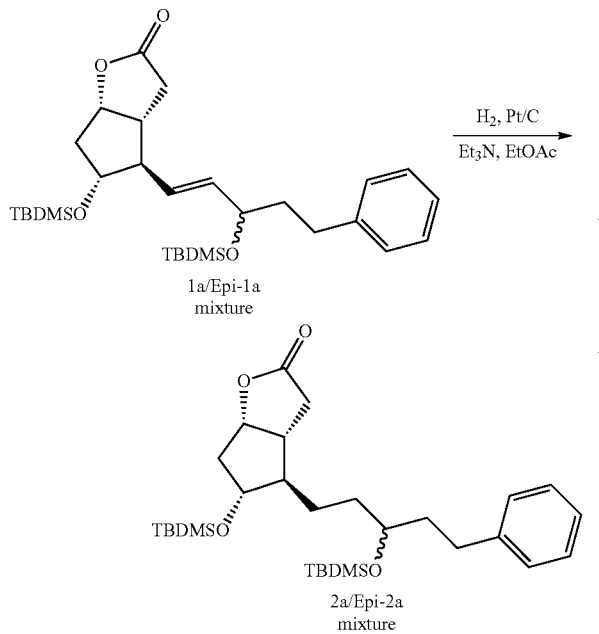

The lactone bis-TBDMS-protected diol compound 1a/Epi-1a mixture (Example 1, 3.05 g, 5.75 mmol, 1 molar equivalent) was dissolved in EtOAc (30 mL, 10 volumes) and charged to a pressure tube under nitrogen. Platinum on carbon (10%, 0.3 g, 10% wt/wt, dry catalyst) and triethylamine (Et₃N, 0.88 g., 8.7 mmol, 1.5 molar equivalents) were added to the solution. The pressure tube was sealed and purged with hydrogen gas three times at 30 pounds per square inch (psi). The pressure tube was pressurized to 40 psi and shaken on the shaker at room temperature for no less than 15 hours. After completion of reaction, as judged by TLC and NMR, the reaction mixture was filtered to remove the catalyst. The filtrate was concentrated under reduced pressure to provide the product mixture as a residue.

Steps B and C

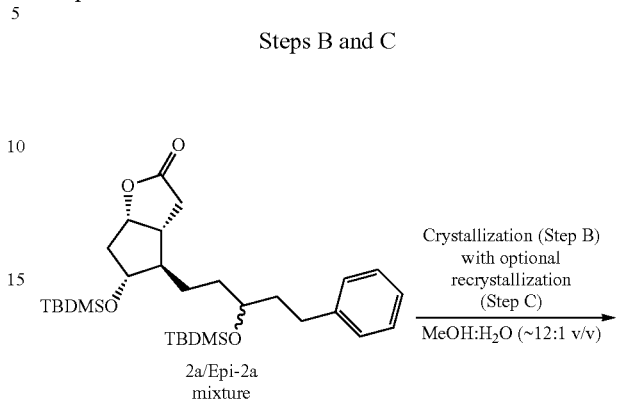

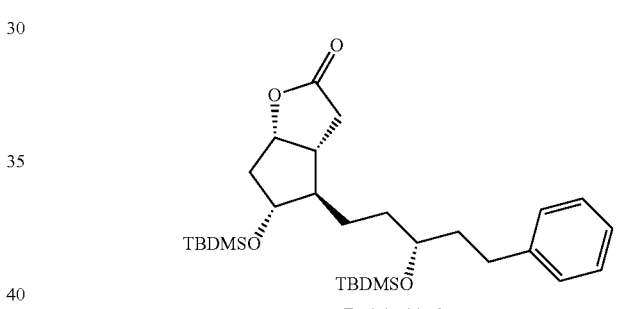

Step B: Crystallization of Lactone Bis-TBDMS-protected Diol Compound Mixture 2a/Epi-2a The residue (crude compound mixture 1a/Epi-1a prepared in Step B of Example 2 above) was dissolved in methanol (18 mL, 6 volumes) and charged to a round bottom flask fitted with a mechanical stirrer, and a thermocouple. The mixture was stirred at room temperature. Deionized water (1.5 mL, 0.5 volume) was added slowly to the stirred solution. A white solid crystallized. The mixture was stirred at room temperature for no less than one hour. The mixture was cooled to 0±5° C. The white solid was filtered on a medium porosity (10-16 μm) fritted glass funnel, rinsed with two 2-mL portions of deionized water, collected, and dried under vacuum (5 mmHg, 45° C.) to afford 2.65 g (87%) of the enantiomerically-enriched title compound (2a) as a white solid.

Step C: Recrystallization of Enantiomerically-enriched Lactone Bis-TBDMS-protected Diol Compound (2a)

Crystallized material from Step C may be recrystallized by repeating the crystallization procedure described above in Step C of Example 2 to provide solid compound further enriched in compound 2a.

The following table records 3a/Epi-3a (not mentioned in Example 2, but the material from which the Step A starting material originated), 1a/Epi-1a, and 2a/Epi-2a epimeric ratios of mixtures, which are provided as described by the procedures of Example 2, as determined by HPLC-UV. Relative absorbance between single entities of epimeric pairs is assumed to be equivalent. In this set of trials, mixture 1a/Epi-1a that had been obtained from a single crystallization (from Example 1, Step C), was used as starting material in this Example (Example 2), Step A.

| Trial # | 3a/Epi-3a ratio (starting mat.) | 1a/Epi-1a ratio (crystallized once) Ex. 1, Step C | 2a/Epi-2a ratio (crystallized once) Step B | 2a/Epi-2a ratio (crystallized twice) Step C |
|---|---|---|---|---|
| 1 | 98.67/1.3 | 99.8/0.2 | >99.93/ND | N/A |
| 2 | 92.91/7.09 | 99.14/0.85 | 99.93/0.065 | N/A |
| 3 | 97.49/2.51 | 96.75/3.245 | | 99.85/0.15 |
| 4 | 96.03/3.97 | 97.11/2.89 | 99.41/0.59 | >99.99/ND |
| 5 | 85.08/14.91 | 92.08/7.92 | 97.72/2.28 | 99.07/0.93 |
| 6 | 98.9/1.1 | 99.5/0.5 | >99.99/ND | >99.99/ND |

The following table records 3a/Epi-3a (not mentioned in Example 2, but the material from which the Example 2, Step A starting material originated), 1a/Epi-1a, and 2a/Epi-2a epimeric ratios of mixtures, which are provided as described by the procedures of Example 2, as determined by HPLC-UV. Relative absorbance between single entities of epimeric pairs is assumed to be equivalent. In this set of trials, mixture 1a/Epi-1 a that had been obtained from crystallization and recrystallization (from Example 1, Step D), was used as starting material in Example 2, Step A.

| Trial # | 3a/Epi-3a ratio (starting mat.) | 1a/Epi-1a ratio (crystallized twice) Ex. 1, Step D | 2a/Epi-2a ratio (crystallized once) Step B | 2a/Epi-2a ratio (crystallized twice) Step C |
|---|---|---|---|---|
| 1 | 92.91/7.09 | 99.79/0.21 | 99.905/0.095 | N/A |
| 2 | 99.49/0.5 | 99.97/0.03 | >99.95/ND | N/A |
| 3 | 97.49/2.51 | 99.32/0.68 | 99.83/0.17 | >99.99/ND |
| 4 | 96.03/3.97 | 99.19/0.81 | 98.97/0.86 | 99.61/0.384 |
| 5 | 85.08/14.91 | 98.5/1.5 | 98.81/0.85 | 99.14/0.54 |
| 6 | 98.9/1.1 | 99.8/0.2 | 94.85/1.59 | 96.69/0.89 |

Example 3

Preparation of bimatoprost ethyl amide (5α-2) from purified (3aR,4R,5R,6aS)-5-(tert-butyldimethylsilyloxy)-4-((S,E)-3-(tert-butyldimethylsilyloxy)-5-phenylpent-1-enyl)hexahydro-2H-cyclopenta[b]furan-2-one (1a)

Step A: Preparation of (3aR,4R,5R,6aS)-5-(tert-butyldimethylsilyloxy)-4-(S,E)-3-(tert-butyldimethylsilyloxy)-5-phenylpent-1-enyl)hexahydro-2H-cyclopenta[b]furan-2-ol (7a) from highly pure (3aR,4R,5R,6aS)-5-(tert-butyldimethylsilyloxy)-4-((S,E)-3-(tert-butyldimethylsilyloxy)-5-phenylpent-1-enyl)hexahydro-2H-cyclopenta[b]furan-2-one (1a)

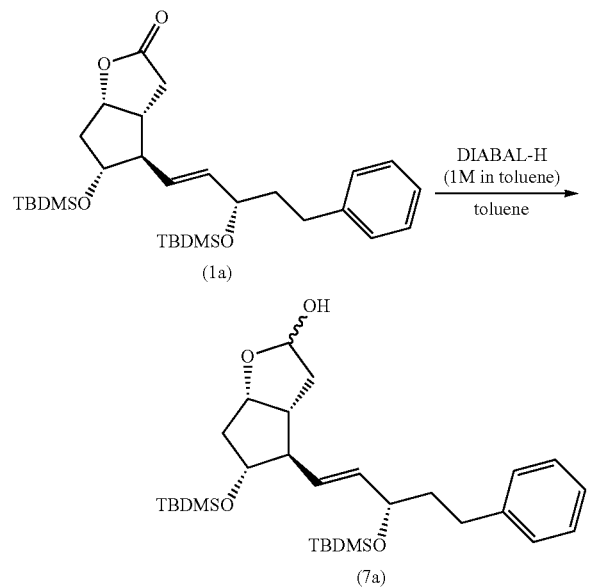

To a jacketed flask fitted with a mechanical stirrer, nitrogen inlet addition funnel, and a thermocouple was charged a solution consisting of (3aR,4R,5R,6aS)-5-(tert-butyldimethylsilyloxy)-4-((S,E)-3-(tert-butyldimethylsilyloxy)-5-phenylpent-1-enyl)hexahydro-2H-cyclopenta[b]furan-2-one (1a) (prepared according to the method described in Example 1, 50 g, 94 mmol, 1.0 molar equivalent) dissolved in toluene (500 mL, 10 volumes). The solution was cooled to −40° C.±5° C. with a refrigerated circulator while the solution continued stirring. One molar DIBAL-H in toluene (135 mL, 1.4 molar equivalents) was added slowly via the addition funnel while maintaining the reaction mixture temperature at −40° C.±5° C. After completion of reaction, as judged by TLC, the reaction mixture was quenched by ethyl acetate (100 mL, 2 volumes all at once). After stirring for 15 minutes, a 30% solution of Rochelle salt (500 mL, 10 volumes) was added and the mixture was allowed to stir at room temperature overnight. The layers were separated and the lower aqueous layer was discarded. The upper organic layer was concentrated under reduced pressure to provide an oil. The resulting oil was further dried under high vacuum for about 2-18 hours to afford the title intermediate (50 g, quantitative yield) as an oil.

Step B: Preparation of a mixture of (Z)-7-((1R,2R, 3R,5S)-3-(tert-butyldimethylsilyloxy)-2-((S,E)-3-(tert-butyldimethylsilyloxy)-5-phenylpent-1-enyl)-5-hydroxycyclopentyl)hept-5-enoic acid (8a-1a) and (Z)-7-(1R,2R,3R,5S)-5-(tert-butyldimethylsilyloxy)-2-(S,E)-3-(tert-butyldimethylsilyloxy)-5-phenylpent-1-env-1)-3-hydroxycyclopentyl)hept-5-enoic acid (8α-1b) from (3aR,4R,5R,6aS)-5-(tert-butyldimethylsilyloxy)-4-((S,E)-3-(tert-butyldimethylsilyloxy)-5-phenylpent-1-enyl)hexahydro-2H-cyclopenta[b]furan-2-ol (7a)

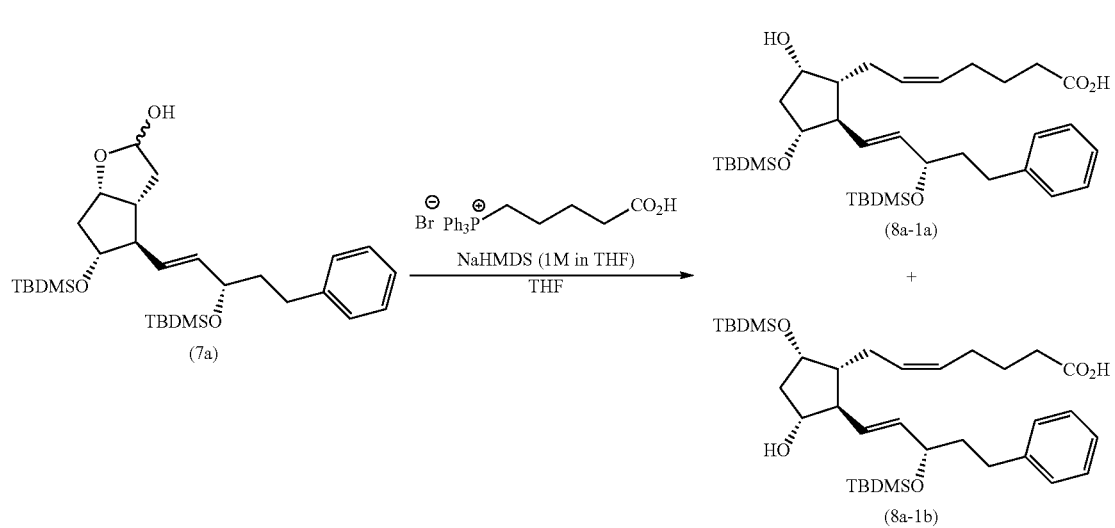

Step B.1: Ylide Formation

To a jacketed flask fitted with a mechanical stirrer, nitrogen inlet addition funnel, and a thermocouple was charged (4-carboxybutyl)triphenylphosphonium bromide (103.7 g., 234.0 mmol, 2.5 molar equivalents) with anhydrous THF (750 mL, 15 volumes). Sodium bis(trimethylsilyl)amide (NaHMDS, 1 M in THF, 505 mL, 5.4 molar equivalents) was placed in the addition funnel via canula and added dropwise to the stirring slurry in the reaction vessel at a rate suitable to maintain the internal temperature of the reaction at 20±5° C. The mixture was allowed to stir for 80 to 100 minutes at 20±5° C. and was subsequently cooled to −15±5° C. using a refrigerated circulator.

Step B.2: Reaction of Ylide with Lactol (7a)

(3aR,4R,5R,6aS)-5-(tert-Butyldimethylsilyloxy)-4-(S,E)-3-(tert-butyldimethylsilyloxy)-5-phenylpent-1-enyl)hexahydro-2H-cyclopenta[b]furan-2-ol (7a) (50 g, 93.9 mmol, 1 molar equivalent) was dissolved in THF (150 mL, 3 volumes) and added to the reaction mixture at a rate suitable to maintain the internal reaction temperature at −15±5° C. After complete addition, the reaction mixture temperature was adjusted to an internal temperature of −5±2.5° C. The reaction mixture was stirred for 3-6 hours while maintaining the internal temperature at −5±2.5° C. After completion of the reaction as judged by TLC, the reaction mixture was quenched by slow addition of 20% ammonium chloride (aqueous) solution (1000 mL, 20 volumes) to the cooled reaction vessel. A solution consisting of 1:1 v/v heptane-ethyl acetate (500 mL, 10 volumes) was added to the reaction mixture and allowed it to stir at room temperature (15-30° C.) for 1-18 hours. The layers were separated and the lower aqueous layer was re-extracted with a solution consisting of 1:1 v/v heptane-ethyl acetate (250 mL, 5 volumes). The combined organic layers were combined and washed five times with 7% brine solution (250 mL, 5 volumes). The upper organic layer was concentrated under reduced pressure. The resulting oil was dissolved in heptanes (500 mL, 10 volumes) and concentrated under reduced pressure. The resulting oil was dissolved in heptanes (500 mL, 10 volumes) and stirred for 15 minutes until completely dissolved. The solution was cooled to −20° C. The mixture was filtered through a coarse fritted funnel to remove the solids. The filtrate was concentrated to an oil under reduced pressure. The resulting oil was further dried under high vacuum for about 2-18 hours to afford the title intermediate mixture (57 g, quantitative yield) as a pale yellow oil.

The following table shows the distribution of the four products, (8a-1a), (8a-1b), and the trans isomers of each (8a-1a) and (8a-1b), called trans-(8a-1a) and trans-(8a-1b), produced by Example 3, Step B with varying parameters of base, time, and reaction temperature of Step B.1, and varying parameters of time and reaction of Step B.2:

|       |        | Step B.1    |              | Step B.2    |              | Products (% of product mixture - HPLC) |         |                    |                    |                        |
|-------|--------|-------------|--------------|-------------|--------------|----------------------------------------|---------|--------------------|--------------------|------------------------|
| Trial # | Base | Time (h)    | Temp. (° C.) | Time (h)    | Temp. (° C.) | (8a-1a)                                | (8a-1b) | trans-<br>(8a-1a)  | trans-<br>(8a-1b)  | Total isolated<br>% yield |
| 1     | NaHMDS | 1           | room temp.   | 4           | −5           | 79.40                                  | 12.20   | 1.07               | 0.41               | 81                     |
| 2     | NaHMDS | 1           | room temp.   | 2           | −10          | 86.16                                  | 11.97   | 0.44               | 1.43               | 95                     |
| 3     | NaHMDS | 1           | −25          | 3           | 0            | 88.70                                  | 9.00    | 1.74               | 0.50               | 95                     |
| 4     | NaHMDS | 1           | room temp.   | 2.5         | −10          | 89.80                                  | 7.80    | 1.84               | 0.56               | 95                     |
| 5     | KO$^t$Bu | 1         | room temp.   | 4           | −5           | 63.30                                  | 20.60   | 1.70               | 1.17               | 95                     |
| 6     | KO$^t$Bu | 1         | room temp.   | 2.5         | −10          | 72.9                                   | 23.8    | 2.0                | 1.4                | 95                     |

Step C: Preparation of a mixture of (Z)-7-((1R,2R,3R,5S)-3-(tert-butyldimethylsilyloxy)-2-((S,E)-3-(tert-butyldimethylsilyloxy)-5-phenylpent-1-enyl)-5-hydroxycyclopentyl)-N-ethylhept-5-enamide (9a-2a) and (Z)-7-((1R,2R,3R,5S)-5-(tert-butyldimethylsilyloxy)-2-((S,E)-3-(tert-butyldimethylsilyloxy)-5-phenylpent-1-enyl)-3-hydroxycyclopentyl)-N-ethylhept-5-enamide (9a-2b) from a mixture of (Z)-7-((1R,2R,3R,5S)-3-(tert-butyldimethylsilyloxy)-2-((S,E)-3-(tert-butyldimethylsilyloxy)-5-phenylpent-1-enyl)-5-hydroxycyclopentyl)hept-5-enoic acid (8a-1a) and (Z)-7-((1R,2R,3R,5S)-5-(tert-butyldimethylsilyloxy)-2-((S,E)-3-(tert-butyldimethylsilyloxy)-5-phenylpent-1-enyl)-3-hydroxycyclopentyl)hept-5-enoic acid (8a-1b)

To a three-necked round bottom flask equipped with a mechanical stirrer, nitrogen inlet addition funnel, and a thermocouple was charged a solution consisting of crude bis-TBDMS bimatoprost free acid mixture (8a-1a) and (8a-1b) (57 g, 92 mmol, 1 molar equivalent) in dichloromethane (570 mL. 10 volumes). N-hydroxysuccinimide (21.2 g, 185 mmol, 2 molar equivalents) was added to the solution followed by N,N' dicyclohexylcarbodiimide (DCC, 38.1 g, 185 mmol, 2 molar equivalents). The mixture was allowed to stir for at least two hours at 20±5° C. After completion of the reaction, as judged by TLC, the reaction mixture was filtered through a sintered glass funnel and the solid was washed with dichloromethane (115 mL, 2 volumes). The filtrate was returned to the round bottom flask and treated with 2 M ethyl amine in THF (93 mL, 2 molar equivalents). The reaction mixture was stirred at room temperature for at least two hours, but no longer than overnight (do we want a hard number here). After completion of the reaction, as judged by TLC, the reaction mixture was filtered through a sintered glass funnel and the solid was washed with dichloromethane (115 mL., 2 volumes). The reaction mixture was washed with deionized

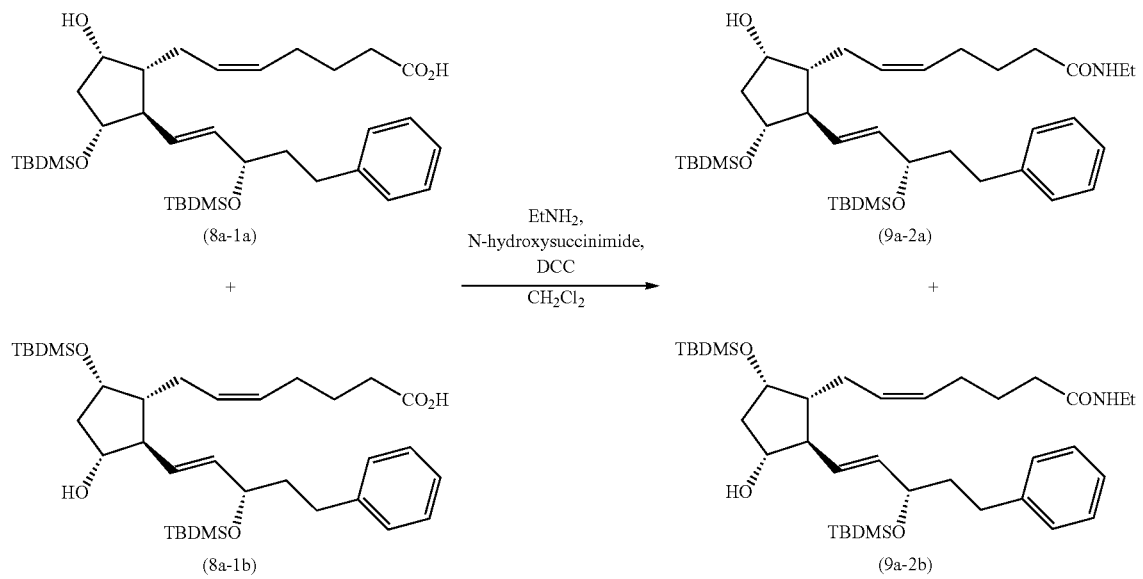

water (3×250 mL, 3×4.4 volumes). The organic solution was concentrated under reduced pressure to afford the title intermediate mixture (63.4 g) as an oil.

Step D: Preparation of bimatoprost ethyl amide (5α-2) from a mixture of (Z)-7-((1R,2R,3R,5S)-3-(tert-butyldimethylsilyloxy)-2-((S,E)-3-(tert-butyldimethylsilyloxy)-5-phenylpent-1-enyl)-5-hydroxycyclopentyl)-N-ethylhept-5-enamide (9a-2a) and (Z)-7-((1R,2R,3R,5S)-5-(tert-butyldimethylsilyloxy)-2-((S,E)-3-(tert-butyldimethylsilyloxy)-5-phenylpent-1-enyl)-3-hydroxycyclopentyl)-N-ethylhept-5-enamide (9a-2b)

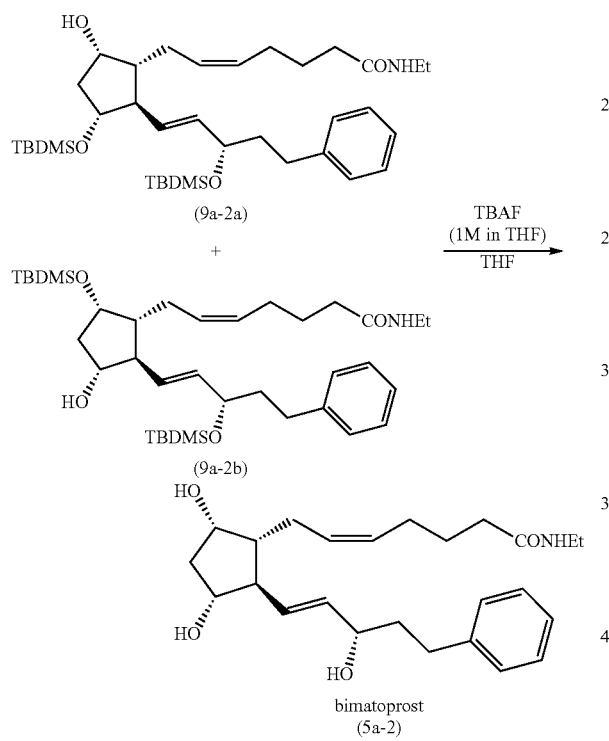

To a three-necked round bottom flask equipped with a mechanical stirrer, nitrogen inlet addition funnel, and a thermocouple was charged a solution comprising a mixture of (Z)-7-((1R,2R,3R,5S)-3-(tert-butyldimethylsilyloxy)-2-((S,E)-3-(tert-butyldimethylsilyloxy)-5-phenylpent-1-enyl)-5-hydroxycyclopentyl)-N-ethylhept-5-enamide (9a-2a) and (Z)-7-((1R,2R,3R,5S)-5-(tert-butyldimethylsilyloxy)-2-((S,E)-3-(tert-butyldimethylsilyloxy)-5-phenylpent-1-enyl)-3-hydroxycyclopentyl)-N-ethylhept-5-enamide (9a-2b) (57 g, 89 mmol, 1 molar equivalent) in THF (570 mL, 10 volumes). Tetrabutylammonium fluoride (TBAF, 355 mL, 355 mmol, 4 molar equivalents) was added to the solution at once. The mixture was allowed to stir at 40±5° C. overnight. After completion of the reaction, as judged by TLC, the reaction mixture was diluted with ethyl acetate (400 mL, 7 volumes) and cooled to 5±5° C. Deionized water (570 mL, 10 volumes) was added to the reaction. The layers were separated and the lower aqueous layer was treated with 1.8 parts of sodium chloride (100 g) and re-extracted with ethyl acetate (400 mL, 7 volumes). The organic solution was concentrated under reduced pressure. The residue was redissolved in ethyl acetate (420 mL, 7.4 volumes) and with 7% sodium chloride solution (4×240 mL, 4×4.2 volumes). The organic solution was concentrated under reduced pressure to afford an oily product (52 g). The crude product was purified on AnaLogix® flash silica column (600 g). Ethyl acetate and methanol were used as eluents. The product fractions were combined and concentrated to afford a white solid (23 g). The solid was further purified by dissolving in acetone (184 mL, 8 volumes) and diluted with slow addition of methyl tert-butyl ether (MTBE, 736 mL, 32 volumes). The resulting mix was stirred overnight at room temperature. The mixture was cooled to 5±5° C. and was subsequently filtered and the solid was washed with MTBE (2×50 mL). The solid was dried under high vacuum at about 50° C. to afford a white solid (21.5 g). The obtained solid was dissolved in acetone (170 mL, 8 volumes) and diluted with slow addition of MTBE (690 mL, 32 volumes). The resulting mix was stirred overnight at room temperature. The mixture was cooled to 5±5° C. and was subsequently filtered and the solid was washed with MTBE (2×50 mL). The solid was dried under hi vacuum at about 50° C. to afford the purified title compound (18.54 g, >99.99% pure by HPLC-UV) as white solid.

Example 4

Preparation of latanoprost isopropyl ester (6a-3) from purified (3aR,4R,5R,6aS)-5-(tert-butyldimethylsilyloxy)-4-((R)-3-(tert-butyldimethylsilyloxy)-5-phenylpentyl)hexahydro-2H-cyclopenta[b]furan-2-one (2a)

Step A: Preparation of (3aR,4R,5R,6aS)-5-(tert-butyldimethylsilyloxy)-4-((R)-3-(tert-butyldimethylsilyloxy)-5-phenylpentyl)hexahydro-2H-cyclopenta[b]furan-2-ol (10a) from highly pure (3aR,4R,5R,6aS)-5-(tert-butyldimethylsilyloxy)-4-(R)-3-(tert-butyldimethylsilyloxy)-5-phenylpentyl)hexahydro-2H-cyclopenta[b]furan-2-one (2a)

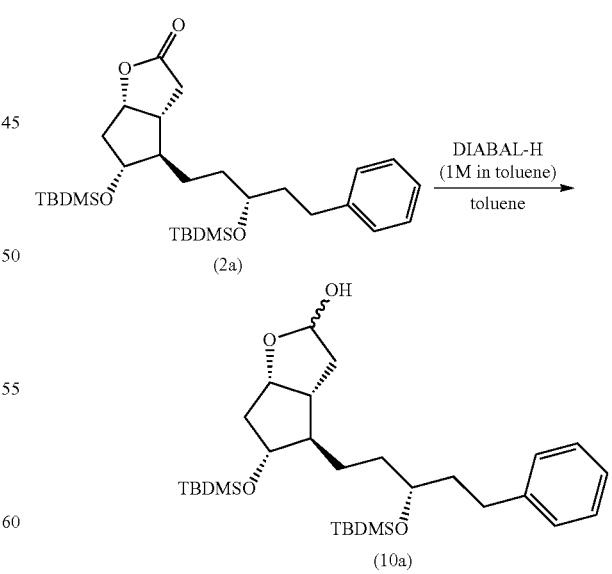

To a 10-L jacketed flask fitted with a mechanical stirrer, nitrogen inlet addition funnel, and a thermocouple was charged a solution consisting of (3aR,4R,5R,6aS)-5-(tert-butyldimethylsilyloxy)-4-((R)-3-(tert-butyldimethylsilyloxy)-

5-phenylpentyl)hexahydro-2H-cyclopenta[b]furan-2-one (2a) (prepared according to the method described in Example 2, 300.15 g, 563.2 mmol, 1 molar equivalent) dissolved in toluene (3000 mL, 10 volumes). The stirring solution was cooled to −40±5° C. with a refrigerated circulator. Diisopropylaluminum hydride (1 M in toluene, 850 mL, 1.5 molar equivalents) was added slowly via the addition funnel while maintaining the reaction mixture temperature at −40±5° C. After completion of reaction, as judged by TLC, the reaction mixture was quenched by ethyl acetate (600 mL, 2 volumes all at once). After stirring for 15 minutes, a 30% solution of Rochelle salt (3000 mL, 10 volumes) was added and the mixture was allowed to stir at room temperature overnight. The layers were separated and the lower aqueous layer was discarded. The upper organic layer was concentrated under reduced pressure. The resulting oil was dissolved in heptanes (3000 mL, 10 volumes) and concentrated under reduced pressure at 40±5° C. Again, the resulting oil was dissolved in heptanes (3000 mL, 10 volumes) and concentrated under reduced pressure at 40±5° C. The resulting oil was further dried under high vacuum for about 2-18 hours to afford the title intermediate (298.3 g, 99.4% yield), as an oil.

Step B: Preparation of a mixture of (Z)-7-((1R,2R,3R,5S)-3-(tert-butyldimethylsilyloxy)-2-((R)-3-(tert-butyldimethylsilyloxy)-5-phenylpentyl)-5-hydroxycyclopentyl)hept-5-enoic acid (11a-1a) and (Z)-7-((1R,2R,3R,5S)-5-(tert-butyldimethylsilyloxy)-2-((R)-3-(tert-butyldimethylsilyloxy)-5-phenylpentyl)-3-hydroxycyclopentyl)hept-5-enoic acid (11a-1b) from (3aR,4R,5R,6aS)-5-(tert-butyldimethylsilyloxy)-4-((R)-3-(tert-butyldimethylsilyloxy)-5-phenylpentyl)hexahydro-2H-cyclopenta[b]furan-2-ol (10a)

M in THF, 2780 mL, 5.4 molar equivalents) was placed in the addition funnel via canula and added dropwise to the stirring slurry in the reaction vessel at a rate suitable to maintain the internal temperature of the reaction at 20±5° C. The mixture was allowed to stir for 80 to 100 minutes at 20±5° C. and was subsequently cooled to −15±5° C. using a refrigerated circulator.

(3aR,4R,5R,6aS)-5-(tert-Butyldimethylsilyloxy)-4-((R)-3-(tert-butyldimethylsilyloxy)-5-phenylpentyl)hexahydro-2H-cyclopenta[b]furan-2-ol (10a) (296.6 g, 555 mmol, 1 molar equivalent) was dissolved in THF (1100 mL, 4 volumes) and added to the reaction mixture at a rate suitable to maintain the internal reaction temperature at −15±5° C. After complete addition, the reaction mixture temperature was adjusted to an internal temperature of −5±2.5° C. The reaction mixture was stirred for 3-6 hours while maintaining the internal temperature at −5±2.5° C. After completion of the reaction, as judged by TLC, the reaction mixture was quenched by slow addition of 20% ammonium chloride (aqueous) solution (5500 mL, 20 volumes) to the cooled reaction vessel. A solution consisting of 1:1 v/v heptane-ethyl acetate (2750 mL, 10 volumes) was added to the reaction mixture and allowed it to stir at room temperature (15-30° C.) for 1-18 hours. The layers were separated and the lower aqueous layer was extracted twice with a solution consisting of 1:1 v/v heptane-ethyl acetate (2×1375 mL, 2×5 volumes). The combined organic layers were combined and washed five times with a 7% brine solution (5×1375 mL, 5×5 volumes). The upper organic layer was concentrated under reduced pressure. The resulting oil was dissolved in heptanes (2750 mL, 10 volumes) and concentrated under reduced pressure. The resulting oil was dissolved in heptanes (2750 mL, 10 volumes) and stirred for 15 minutes until completely dissolved. The solution was cooled to −20° C. The mixture was filtered through

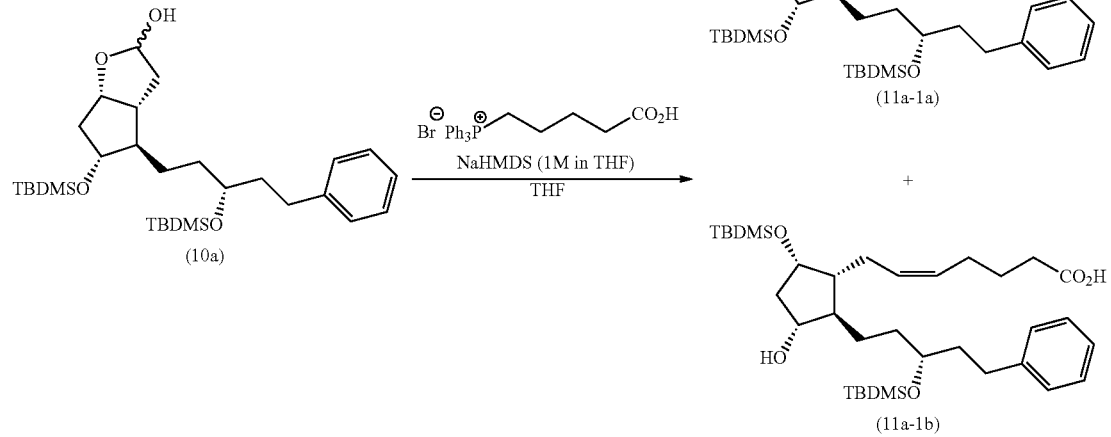

To a jacketed flask fitted with a mechanical stirrer, nitrogen inlet addition funnel, and a thermocouple was charged (4-carboxybutyl)triphenylphosphonium bromide (570.5 g., 1287 mmol, 2.5 molar equivalents) with anhydrous THF (4125 mL, 15 volumes). Sodium bis(trimethylsilyl)amide (NaHMDS, 1 a coarse fritted funnel to remove the solids. The filtrate was concentrated to an oil under reduced pressure. The resulting oil was further dried under high vacuum for about 2-18 hours to afford the title intermediate mixture (364.4 g, quantitative yield) as a pale yellow oil.

Step C: Preparation of a mixture of (Z)-isopropyl 7-((1R,2R,3R,5S)-3-(tert-butyldimethylsilyloxy)-2-(R)-3-(tert-butyldimethylsilyloxy)-5-phenylpentyl)-5-hydroxycyclopentyl)hept-5-enoate (12a-3a) and (Z)-isopropyl 7-((1R,2R,3R,5S)-5-(tert-butyldimethylsilyloxy)-2-(R)-3-(tert-butyldimethylsilyloxy)-5-phenylpentyl)-3-hydroxycyclopentyl)hept-5-enoate (12a-3b) from a mixture of (Z)-7-((1R,2R,3R,5S)-3-(tert-butyldimethylsilyloxy)-2-((R)-3-(tert-butyldimethylsilyloxy)-5-phenylpentyl)-5-hydroxycyclopentyl)hept-5-enoic acid (11a-1a) and (Z)-7-((1R,2R,3R,5S)-5-(tert-butyldimethylsilyloxy)-2-((R)-3-(tert-butyldimethylsilyloxy)-5-phenylpentyl)-3-hydroxycyclopentyl)hept-5-enoic acid (11a-1b)

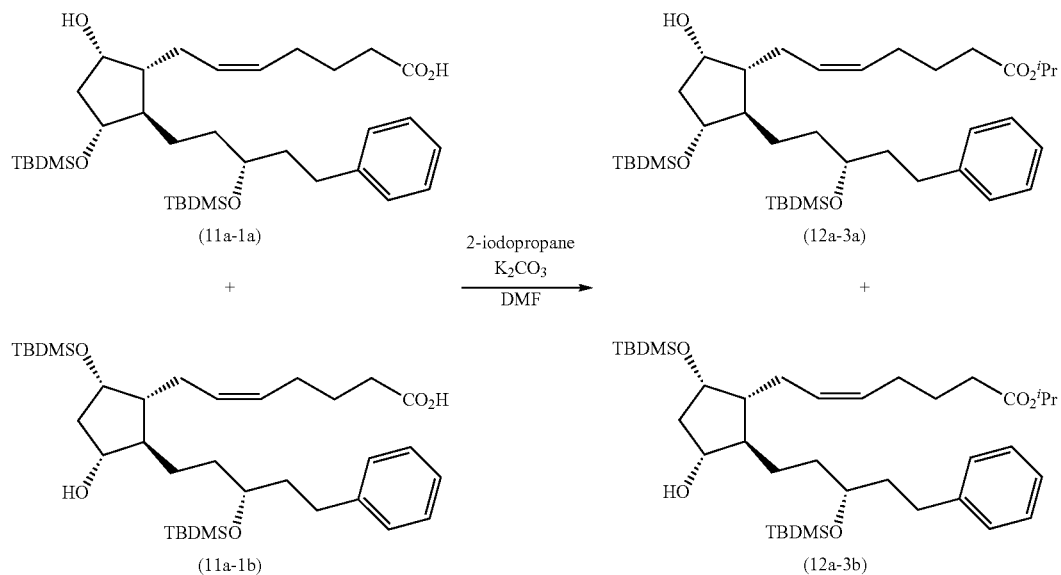

To a three-necked round bottom flask equipped with a mechanical stirrer, nitrogen inlet addition funnel, and a thermocouple was added a solution consisting of a mixture of (Z)-7-((1R,2R,3R,5S)-3-(tert-butyldimethylsilyloxy)-2-((R)-3-(tert-butyldimethylsilyloxy)-5-phenylpentyl)-5-hydroxycyclopentyl)hept-5-enoic acid (11a-1a) and (Z)-7-((1R,2R,3R,5S)-5-(tert-butyldimethylsilyloxy)-2-((R)-3-(tert-butyldimethylsilyloxy)-5-phenylpentyl)-3-hydroxycyclopentyl)hept-5-enoic acid (11a-1b) (318.7 g, 1 molar equivalent) in DMF (3200 mL. 10 volumes). Potassium carbonate (149.5 g, 2.1 molar equivalents) was added to the solution followed by 2-iodopropane (202 g, 2.3 molar equivalents). The reaction mixture was heated to 40±5° C. and stirred for 2 to 6 hours at 40±5° C. After completion of the reaction as judged by TLC, the reaction mixture was cooled to 0±5° C. The reaction mixture was diluted with distilled water (6360 mL, 20 volumes) was subsequently quenched by slow addition of a 5% aqueous citric acid solution (4770 mL, 15 volumes). A solution consisting of 1:1 v/v heptane-ethyl acetate (3180 mL, 10 volumes) was added and the reaction mixture was allowed to stir at room temperature (15-30° C.) for no longer than 5 minutes. The layers were separated and the lower aqueous layer was extracted with a solution consisting of 1:1 v/v heptane-ethyl acetate (2×3180 mL, 2×10 volumes). The combined organic solution was washed with 14% sodium chloride solution (3180 mL, 10 volumes) and was subsequently concentrated under reduced pressure to afford an oily product (366.3 g). The crude product was purified on a Biotage® column using heptanes and ethyl acetate as eluents. The product fractions were combined and concentrated to afford the title intermediate mixture (329 g) as an oil.

Step D: Preparation of latanoprost isopropyl ester (6a-3) from a mixture of (Z)-isopropyl 7-((1R,2R,3R,5S)-3-(tert-butyldimethylsilyloxy)-2-((R)-3-(tert-butyldimethylsilyloxy)-5-phenylpentyl)-5-hydroxy-cyclopentyl)hept-5-enoate (12a-3a) and (Z)-isopropyl 7-((1R,2R,3R,5S)-5-(tert-butyldimethylsilyloxy)-2-((R)-3-(tert-butyldimethylsilyloxy)-5-phenylpentyl)-3-hydroxycyclopentyl)hept-5-enoate (12a-3b)

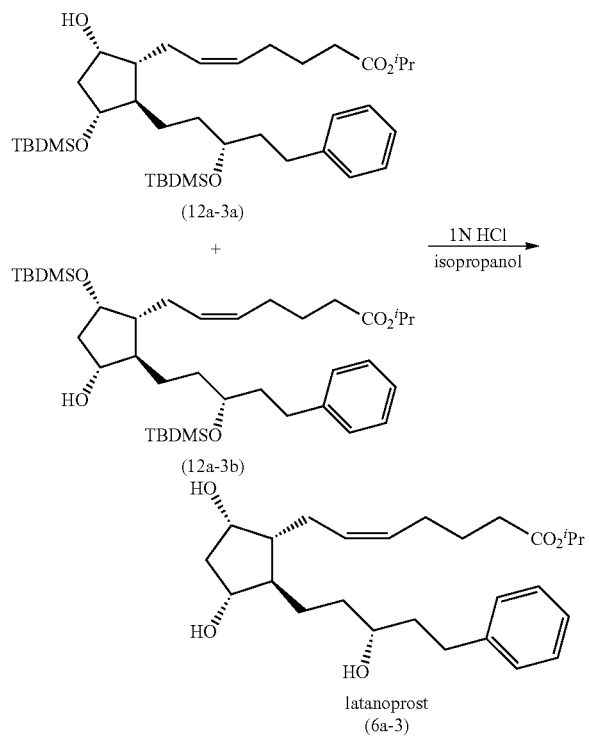

To a three-necked round bottom flask equipped with a mechanical stirrer, nitrogen inlet addition funnel, and a thermocouple was added a solution consisting of a mixture of (Z)-isopropyl 7-((1R,2R,3R,5S)-3-(tert-butyldimethylsilyloxy)-2-((R)-3-(tert-butyldimethylsilyloxy)-5-phenylpentyl)-5-hydroxycyclopentyl)hept-5-enoate (12a-3a) and (Z)-isopropyl 7-((1R,2R,3R,5S)-5-(tert-butyldimethylsilyloxy)-2-((R)-3-(tert-butyldimethylsilyloxy)-5-phenylpentyl)-3-hydroxycyclopentyl)hept-5-enoate (12a-3b) (176.2 g, 1 molar equivalent) in isopropyl alcohol (IPA) (2480 mL., 14 volumes). A 1 M aqueous hydrochloric acid solution (234 mL, 0.8 molar equivalent) was added to the solution at once. The mixture was allowed to stir at 25±5° C. overnight. After completion of the reaction, as judged by TLC, the reaction mixture was cooled to 0±5° C. and quenched with a 10% aqueous KHCO₃ solution (880 mL, 5 volumes). Isopropyl acetate (IPAc) (2640 mL, 15 volumes) was added to the quenched reaction and stirred for no longer than five minutes. The layers were separated and the lower aqueous layer was extracted with IPAc (2×880 mL, 2×5 volumes). The combined organic solution was washed with a 7% aqueous sodium chloride solution (2640 mL, 15 volumes). The organic solution was concentrated under reduced pressure to afford an oil (118.1 g). The crude product was purified on an Analogix® silica column (50 μm silica particles). Heptane and IPA were used as eluents. The product fractions were combined and concentrated under reduced pressure to afford highly pure (chemically and stereochemically) latanoprost isopropyl ester (6a-3) (107.8 g) as an oil.

Example 5

Preparation of (Z)-isopropyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (fluprostenol isopropyl ester, or Travoprost®) (5b-3)

Step A: Preparation of methyl 2-(3-(trifluoromethyl)phenoxy)acetate

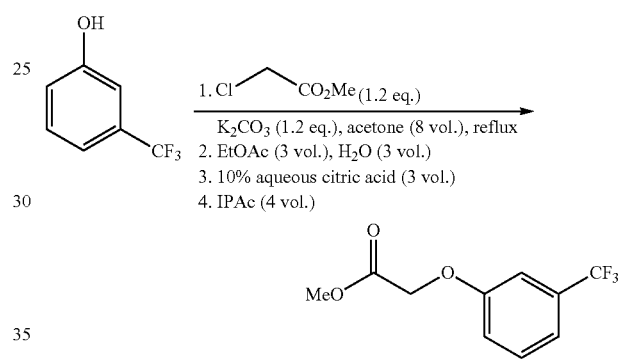

To a 12-L three-necked round-bottom flask fitted with a mechanical stirrer and a thermocouple was charged solid potassium carbonate (709.4 g, 5.140 mol, 1.2 molar equivalents) and acetone (5300 mL). The mixture was stirred and 3-trifluoromethylphenol (694.4 g, 4.28 mol, 1.0 molar equivalent) was added dropwise via 500-mL addition funnel over one hour. The internal temperature rose from 19.6° C. to 28.1° C. during the addition. The addition funnel was rinsed with acetone (100 mL). The rinse was charged to the vessel. The mixture was stirred and methyl chloroacetate (786.3 g, 5.140 mol, 1.2 molar equivalents) was charged dropwise via 500-mL addition funnel over one hour. The addition funnel was rinsed with acetone (100 mL). The rinse was charged to the vessel. The resulting mixture was stirred and heated to reflux for no less than 15 hours. After completion of reaction, as judged by TLC, the reaction mixture was cooled to room temperature and diluted with ethyl acetate (2000 mL) and water (2000 mL). Some solids did not dissolve but that did not prevent a clean layer separation. The layers were separated (pH of lower aqueous layer: 11). The upper organic layer was treated (slow addition) with 10% w/w aqueous citric acid (2000 mL). All solids dissolved and the layers were separated (pH of lower aqueous layer: 8). The organic layer was concentrated in vacuo (20 mmHg, bath at 30-35° C.). The resulting biphasic residue was dissolved in isopropyl acetate (3000 mL). The layers of the resulting biphasic mixture were separated (pH of lower aqueous layer: 8). The upper organic layer was concentrated in vacuo (20 mmHg, bath at 30-35° C.). The resulting residue was distilled under reduced pressure (boil-

Step B: Preparation of dimethyl 2-oxo-3-(3-(trifluoromethyl)phenoxy)propylphosphonate

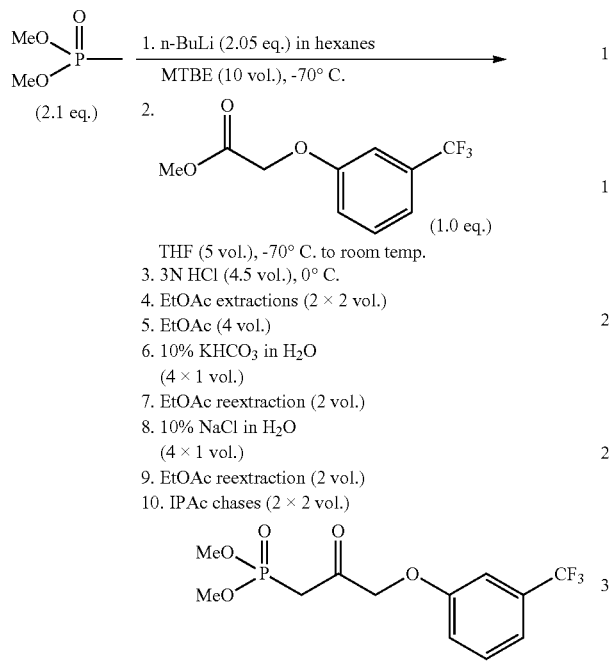

1. n-BuLi (2.05 eq.) in hexanes MTBE (10 vol.), -70° C.
2. [structure]
   THF (5 vol.), -70° C. to room temp.
3. 3N HCl (4.5 vol.), 0° C.
4. EtOAc extractions (2 × 2 vol.)
5. EtOAc (4 vol.)
6. 10% KHCO₃ in H₂O (4 × 1 vol.)
7. EtOAc reextraction (2 vol.)
8. 10% NaCl in H₂O (4 × 1 vol.)
9. EtOAc reextraction (2 vol.)
10. IPAc chases (2 × 2 vol.)

To a nitrogen-purged 12-L three-necked round-bottom flask fitted with a mechanical stirrer, a nitrogen inlet, a Claisen head supporting a thermocouple, and a nitrogen outlet was charged n-butyllithium (n-BuLi, 1.6 M, 2.58 L, 4.13 mol, 2.05 molar equivalents) and MTBE (2580 mL). The mixture was stirred under a sweep of nitrogen and cooled to between −75 and −70° C. using a dry ice-acetone bath. Dimethyl methylphosphonate (524.6 g, 4.23 mol, 2.1 molar equivalents) dissolved in MTBE (1032 mL) was charged dropwise to the reaction vessel via 1-L addition funnel while maintaining an internal temperature below −65° C. The addition lasted about 3.5 hours. The mixture was allowed to stir for 0.5 hour at about −70° C. and 4-trifluoromethyl-phenoxy-acetic acid methyl ester (471.4 g, 2.02 mol, 1.0 molar equivalent) dissolved in THF (1800 mL) was charged dropwise to the reaction vessel via 1-L addition funnel while maintaining an internal temperature below −65° C. The addition lasted about 6 hours. The mixture stirred for no less than 15 hours while gradually warming to room temperature. The resulting reaction mixture was cooled to between 0 and 5° C. with an ice-water bath. Hydrochloric acid (3 N, 2000 mL) was added dropwise via 1-L addition funnel while maintaining an internal temperature below 25° C. The layers were separated. The lower aqueous layer was reextracted with two portions of ethyl acetate (2×750 mL). The combined organic extracts were concentrated in vacuo (20-25 mmHg, bath at 30-35° C.). The residue was dissolved in ethyl acetate (1550 mL). The resulting solution was washed with four 400-mL portions of 10% w/w aqueous potassium bicarbonate. The pH of last wash was about 9. The combined potassium bicarbonate washes were reextracted with one portion of ethyl acetate (750 mL). The combined organic extracts were washed with four portions of aqueous 10% w/w sodium chloride (4×650 mL). The combined sodium chloride washes were reextracted with one 750-mL portion of ethyl acetate. The combined organic extracts were concentrated in vacuo (20-25 mmHg, bath at 30-35° C.). The resulting residue was azeotropically distilled with two 600-mL portions of isopropyl acetate to afford the title intermediate (783.3 g, potency: 86.3% w/w by ¹H NMR, 92.4% potency adjusted yield) as a cloudy brown oil. The oil was used without further purification in the next step.

Step C: Preparation of (3aR,4R,5R,6aS)-4-formyl-2-oxohexahydro-2H-cyclopenta[b]furan-5-yl biphenyl-4-carboxylate ((−)-Corey aldehyde, PPB-protected) from (3aR,4S,5R,6aS)-4-(hydroxymethyl)-2-oxohexahydro-2H-cyclopenta[b]furan-5-yl biphenyl-4-carboxylate ((−)-Corey alcohol, PPB-protected)

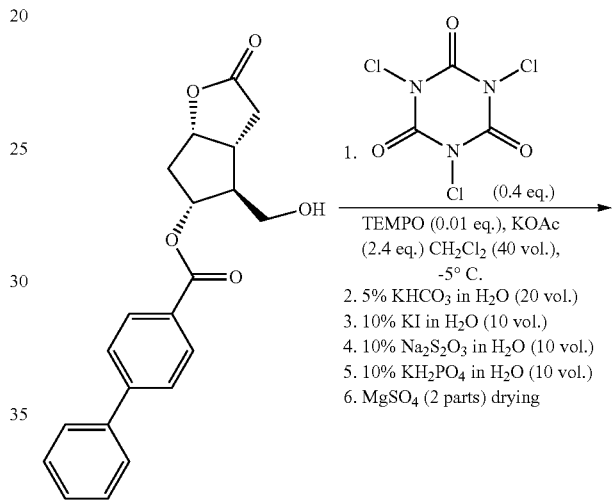

1. [trichloroisocyanuric acid] (0.4 eq.) TEMPO (0.01 eq.), KOAc (2.4 eq.) CH₂Cl₂ (40 vol.), −5° C.
2. 5% KHCO₃ in H₂O (20 vol.)
3. 10% KI in H₂O (10 vol.)
4. 10% Na₂S₂O₃ in H₂O (10 vol.)
5. 10% KH₂PO₄ in H₂O (10 vol.)
6. MgSO₄ (2 parts) drying

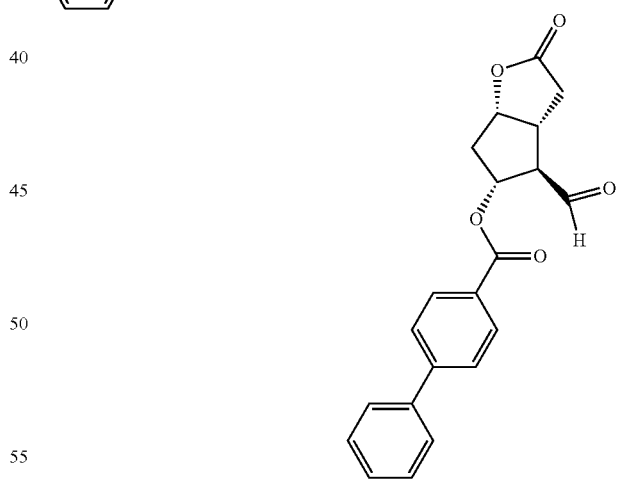

To a 20-L jacketed reactor fitted with a mechanical stirrer and a thermocouple was charged the (−)-Corey alcohol, PPB-protected (250 g, 0.71 mol, 1 molar equivalent), trichloroisocyanuric acid (66 g, 0.29 mol, 0.4 molar equivalent), potassium acetate (166.9 g, 1.74 mol, 2.4 molar equivalents), and dichloromethane (8000 mL). The mixture was stirred and cooled to −5° C. with a circulator. Once the mixture was at the desired temperature, a solution consisting of 2,2,6,6-tetramethyl-piperidin-1-oxyl (TEMPO, 1.13 g, 7 mmol, 0.01 molar equivalent) dissolved in dichloromethane (3 mL) was added in one portion via pipet. The mixture changed from white to a light orange within 30 seconds. The internal temperature rose to 17° C. within 5 minutes. The circulator was adjusted to 3° C. and the mixture was stirred for one hour. After about 15 minutes of stirring, the light orange color turned to white and the internal temperature started to gradually cool to 3° C. The resulting white slurry was treated (strongly effervesces!) with aqueous 5% w/w potassium bicarbonate (5000 mL). The resulting white reaction mixture was filtered through a coarse porosity (40-60 μm) glass fritted funnel. The filtration could be quite slow. The reactor was rinsed with dichloromethane (1000 mL). The rinse was passed through the filter. The layers of the resulting biphasic filtrate were separated and the lower dichloromethane layer was washed with 10% w/w aqueous potassium iodide (2500 mL), 10% w/w aqueous sodium thiosulfate (2500 mL), and 10% w/w potassium dihydrogenphosphate (2500 mL). The lower dichloromethane layer was dried over magnesium sulfate (500 g). The solids were filtered and the title intermediate was carried onto the next step as the filtrate solution.

Step D: Preparation of (3aR,4R,5R,6aS)-2-oxo-4-((E)-3-oxo-4-(3-(trifluoromethyl)phenoxy)but-1-enyl)hexahydro-2H-cyclopenta[b]furan-5-yl biphenyl-4-carboxylate from (−)-Corey aldehyde, PPB-protected To a 20-L jacketed reactor fitted with a mechanical stirrer and a thermocouple was charged the dichloromethane solution of crude (−) Corey aldehyde, PPB-protected (filtrate from Step C, 248.4 g of aldehyde theoretical, 0.71 mol, 1.0 molar equivalent), dimethyl 2-oxo-3-(3-(trifluoromethyl)phenoxy)propylphosphonate (prepared in Step B, 294.8 g with a potency of 86.3% w/w, 254.4 g of theoretical phosphonate, 0.78 mol, 1.1 molar equivalents), and oven-dried lithium chloride (32.8 g, 0.78 mol, 1.1 molar equivalents) dissolved in tetrahydrofuran (2000 mL). The resulting cloudy mixture was cooled to −10° C. with a circulator. Triethylamine (NEt$_3$, 108.5 mL, 78.8 g, 0.78 mol, 1.1 molar equivalent) was added dropwise via 125-mL addition funnel over 30 minutes. At the end of the addition, the circulator was adjusted to −5° C. and the mixture was stirred for no less than 15 hours at this temperature. After completion of the reaction, as judged by $^1$H NMR, the mixture was treated with aqueous 5% w/w citric acid (2500 mL). The layers were separated (pH of upper aqueous layer: 3). The lower dichloromethane layer was concentrated in vacuo (20-25 mmHg, bath at 30-35° C.) to a volume of about 1250 mL. The resulting residue was azeotropically distilled with two 2500-mL portions of methanol. Each time, the distillation was stopped when a final volume of about 1250 mL had been reached. A white solid crystallized during the second azeotropic distillation. The solid was filtered on a medium porosity (10-16 μm) fritted glass funnel,

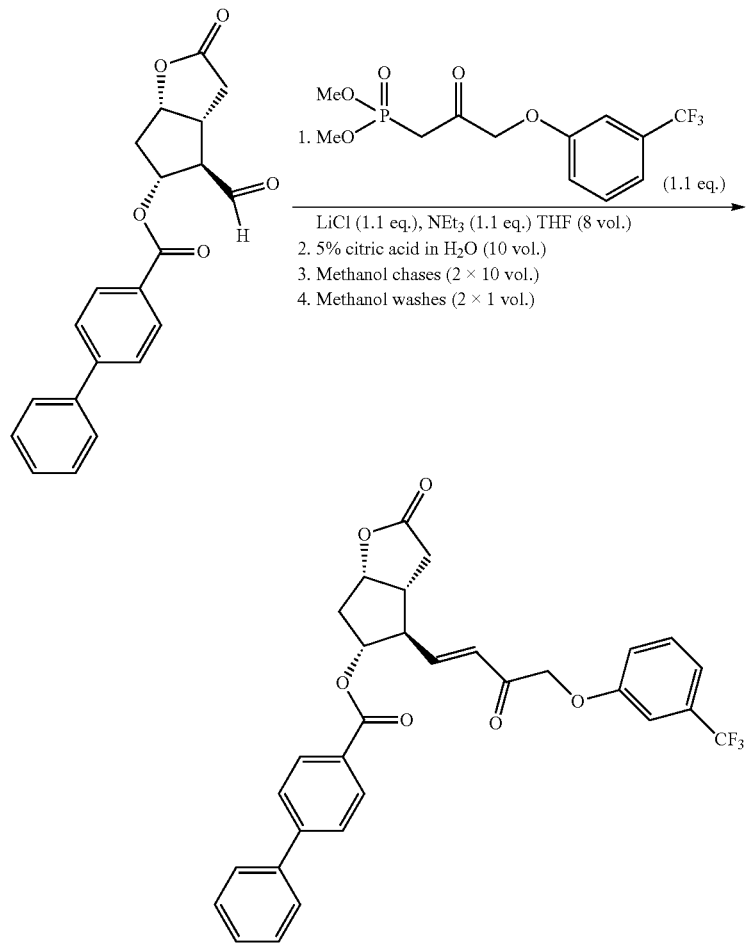

rinsed with three 250-mL portions of methanol, collected, and dried under vacuum (5 mmHg, 25° C.) to afford the title intermediate (184.6 g, 47% yield over two steps from (−)-Corey alcohol, PPB-protected) as a white solid.

Step E: Preparation of mixture comprising (3aR,4R, 5R,6aS)-4-(R,E)-3-hydroxy-4-(3-(trifluoromethyl) phenoxy)but-1-enyl)-2-oxohexahydro-2H-cyclopenta [b]furan-5-yl biphenyl-4-carboxylate (3b) and (3aR, 4R,5R,6aS)-4-((S,E)-3-hydroxy-4-(3-(trifluoromethyl)phenoxy)but-1-enyl)-2-oxohexahydro-2H-cyclopenta[b]furan-5-yl biphenyl-4-carboxylate (Epi-3b) from (3aR,4R,5R,6aS)-2-oxo-4-((E)-3-oxo-4-(3-(trifluoromethyl)phenoxy) but-1-enyl)hexahydro-2H-cyclopenta[b]furan-5-yl biphenyl-4-carboxylate

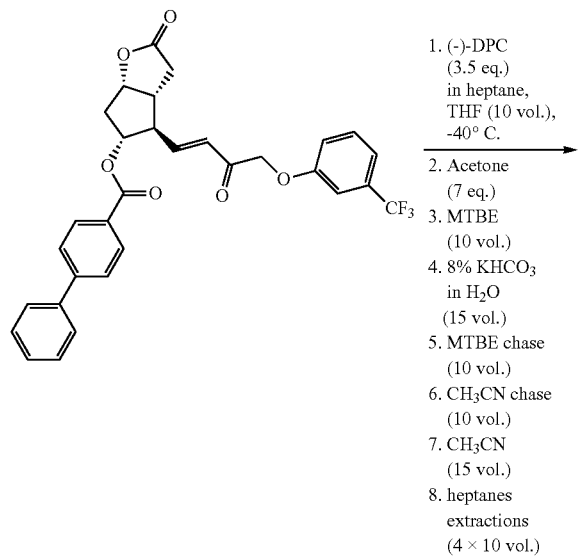

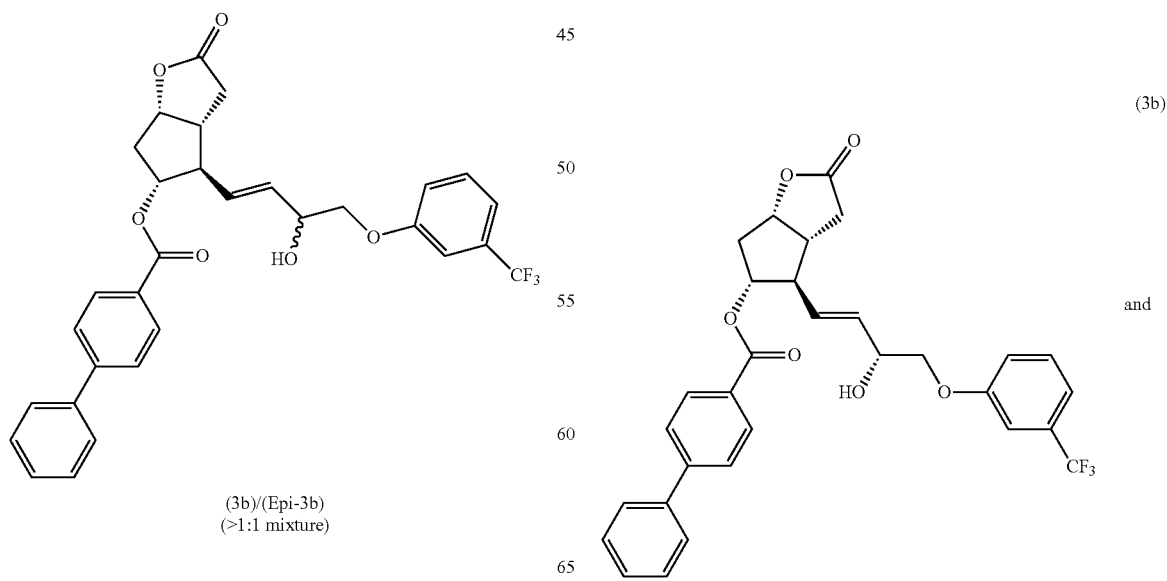

(−)-B-chlorodiisopinocampheylborane ((−)-DPC) solution (878.57 g of 63% w/w solution in heptanes, 553.5 g of theoretical (−)-DPC, 1.72 mol, 3.5 molar equivalents) and tetrahydrofuran (1200 mL). The mixture was then cooled to −40° C. with a circulator set at −43° C. (3aR,4R,5R,6aS)-2-oxo-4-((E)-3-oxo-4-(3-(trifluoromethyl)phenoxy)but-1-enyl) hexahydro-2H-cyclopenta[b]furan-5-yl biphenyl-4-carboxylate (prepared in Step D, 271.4 g, 0.493 mol, 1.0 molar equivalent) dissolved in tetrahydrofuran (1800 mL) was charged dropwise via 1-L addition funnel while maintaining an internal temperature below −35° C. Once the addition was complete, the mixture was stirred for no less than 15 hours at between −42 and −38° C. After completion of reaction, as judged by HPLC, acetone (253 mL, 200.15 g, 3.45 mol, 7.0 molar equivalents) was added and the mixture was gradually warmed to room temperature. The mixture was diluted with MTBE (2700 mL) and treated with aqueous 8% w/w potassium bicarbonate (4000 mL). The layers were separated (pH of lower aqueous layer: 8). The upper organic layer was concentrated in vacuo (20-25 mmHg, bath at 30-35° C.). The residue was azeotropically distilled with two 4000-mL portions of MTBE, then with 2700 mL of acetonitrile. The residue was dissolved in acetonitrile (4000 mL) and heptane (2700 mL). The layers were separated and the lower acetonitrile layer was further washed with three 2700-mL portions of heptanes. The lower acetonitrile layer was concentrated in vacuo (20-25 mmHg, bath at 30-35° C.) to afford the title intermediate as a clear, light-yellow oil. The oil product was analyzed by normal phase HPLC having the following parameters:

i. Eluent: hexanes:ethanol:acetic acid (90:10:0.1), isocratic elution;

ii. Column: Luna, 4.6×150 mm 3 micron, Silica (2), 100 Å, Part Number: 00E-4162-E0;

iii. Detection wavelength (λ): 210 nm;

iv. Result: (3b)/(Epi-3b) mixture:

To a 20-L jacketed reactor fitted with a mechanical stirrer and a thermocouple and flushed with nitrogen was charged a

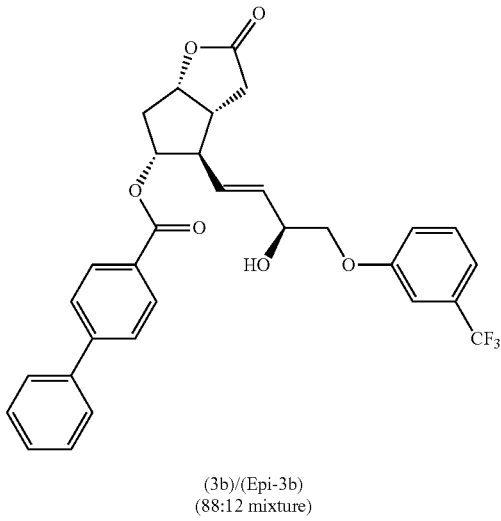

(Epi-3b)

(3b)/(Epi-3b)
(88:12 mixture)

This product was used without further purification in the next step.

Step F: Removal of PPB Protecting Group from Mixture Comprising 3b and Epi-3b To a 3-L three-necked flask fitted with a mechanical stirrer and a thermocouple was charged potassium carbonate solid (102 g, 0.739 mol, 1.5 molar equivalents). The mixture of (3b) and (Epi-3b) prepared in Step E (272.22 g, 0.493 mol, 1.0 molar equivalent) dissolved in methanol (1350 mL) was added and the mixture was stirred at room temperature for no less than 15 hours. After completion of reaction, as judged by TLC, the solids in the reaction mixture were filtered on a medium porosity (10-16 μm) fritted funnel and rinsed with two 250-mL portions of methanol. The resulting filtrate was charged into a three-necked 12-L flask fitted with a mechanical stirrer and a thermocouple. The mixture was diluted with methanol (6300 mL) and potassium hydroxide (KOH, 191.8 g of 87.9% w/w pellets, 168.4 g of theoretical KOH, 3.01 mol, 6.1 molar equivalents) was added followed by water (135 mL). The mixture was stirred and a moderate exotherm from 23° C. to 31° C. was observed before subsiding. The mixture was stirred at room temperature for no less than 15 hours. After completion of reaction, as judged by TLC, the mixture was concentrated in vacuo (20-25 mmHg, bath at 30-35° C.) to a pasty, dark brown residue. The residue was dissolved in water (2700 mL) and MTBE (2700 mL). The layers were separated and the upper organic layer was discarded. The lower aqueous layer was acidified to pH 1 with 3N hydrochloric acid (1630 mL). An impure white solid formed. The solid was dissolved by adding MTBE (2700 mL) and the layers were separated. The lower pH 1 aqueous layer was reextracted with two 1350-mL portions of MTBE. The combined, brown, upper organic layers were washed with a 7% w/w aqueous potassium carbonate (2700 mL). The lower aqueous layer had a dark brown color and a pH of 11. The layers were separated and the lower aqueous layer was reextracted with two 1350-mL portions of MTBE. Some solids (p-phenyl benzoic acid potassium salt) were present at the layers' interface preventing a clear view of the phase separation. The bulk of the lower aqueous layer was drained and the remaining mixture (a small aqueous lower layer and the whole upper organic layer) filtered through a medium porosity (10-16 μm) fritted funnel. The layers of the resulting filtrate were subsequently separated. The combined MTBE layers were charged to a 12-L 3-necked flask fitted with a mechanical stirrer and a thermocouple. A solution of potassium hydroxide (53.4 g of 87.9% w/w pellets, 46.93 g of theoretical KOH, 0.838 mol, 1.7 molar equivalents) in water (2700 mL) was added and the resulting biphasic mixture was vigorously stirred at room temperature for no less than 15 hours. After completion of reaction as judged by TLC, the lower aqueous layer was poured over a mechanically stirred slurry of citric acid (161 g, 0.838 mol, 1.7 molar equivalents) in ethyl acetate (2700 mL) contained in a 5-L three-necked flask. After 15-20 minutes of stirring, the layers were separated. The aqueous phase was reextracted with five 1250-mL portions of ethyl acetate. The combined ethyl acetate extracts were concentrated in vacuo (50 mm Hg, bath at 25° C.) to a volume of about 2160 mL. The resulting mixture was further azeotropically distilled with two 1350-mL portions of ethyl acetate. Each time, the distillation was stopped when a final volume of about 2160 mL had been reached. A white solid began to precipitate at the end of the first azeotropic distillation. The white solid was filtered on a medium porosity (10-16 μm) fritted glass funnel, rinsed with two 270-mL portion of ethyl acetate, collected, and dried under vacuum (5 mmHg, 25° C.) to afford a product mixture (95.5 g, 49.6% yield over three steps from (3aR,4R,5R,6aS)-2-oxo-4-((E)-3-oxo-4-(3-(trifluoromethyl)phenoxy)but-1-enyl)hexahydro-2H-cyclopenta[b]furan-5-yl biphenyl-4-carboxylate) as an off-white solid. The product mixture includes 2-((1R,2R,3R,5S)-3,5-dihydroxy-2-((R,E)-3-hydroxy-4-(3-(trifluoromethyl)phenoxy)but-1-enyl)cyclopentyl)acetic acid (13b), 2-((1R,2R,3R,5S)-3,5-dihydroxy-2-((S,E)-3-hydroxy-4-(3-(trifluoromethyl)phenoxy)but-1-enyl)cyclopentyl)acetic acid (Epi-13b), and (3aR,4R,5R,6aS)-5-hydroxy-4-((R,E)-3-hydroxy-4-(3-(trifluoromethyl)phenoxy)but-1-enyl)hexahydro-2H-cyclopenta[b]furan-2-one (4b) as described below:

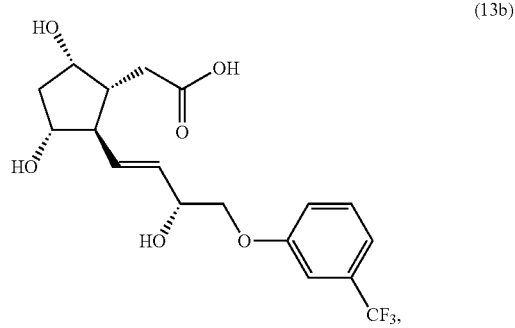

(13b)

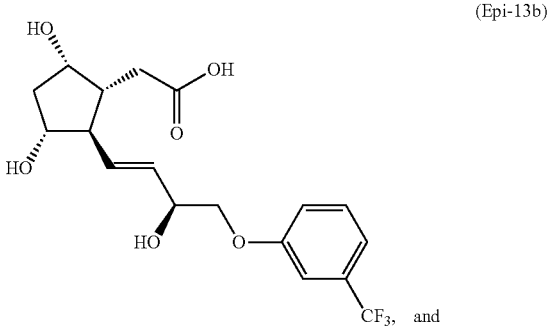

(Epi-13b)

and

-continued

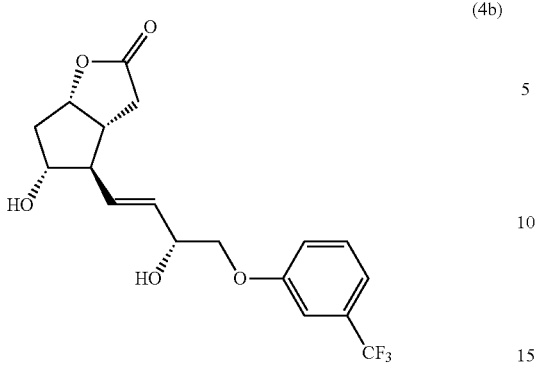
(4b)

The solid was analyzed by normal phase HPLC having the following parameters:
  i. Eluent: hexanes:ethanol:acetic acid (90:10:0.1), isocratic elution
  ii. Column: Luna, 4.6×150 mm 3 micron, Silica (2), 100A, Part Number: 00E-4162-E0
  iii. Detection wavelength (λ): 210 nm
  iv. Result: (13b)/(Epi-13b)-to-(4b) ratio=99.69/0.31; retention time of (13b)/(Epi-13b) mixture=23.549 minutes; retention time of (4b)=27.037 minutes; the relative ratio of (13b)/(Epi-13b) was not assessed, as the two entities did not separate under these conditions.

Step G: Conversion of Mixture Including Compounds (13b), (Epi-13b), and (4b) to Mixture Including Compounds (4b) and (Epi-4-b)

To a 1-L three-necked flask fitted with a mechanical stirrer and a thermocouple was charged the mixture including compounds (13b), (Epi-13b), and (4b) (prepared in Step F, 47.5 g, 0.122 mol, 1.0 molar equivalent) and p-toluenesulfonic acid monohydrate (2.32 g, 0.0122 mol, 0.1 molar equivalent) as solids. Ethyl acetate (380 mL) was added and the resulting white slurry was stirred at room temperature. After 15 minutes of stirring, the solids had completely dissolved and the reaction was complete as judged by TLC. The mixture was further stirred at room temperature for another hour during which time a white solid precipitated. The mixture was cooled to −24.1° C. with a dry-ice acetone bath. The white solid was filtered on a medium porosity (10-16 μm) fritted glass funnel, rinsed with two 50-mL portions of ethyl acetate, collected, and dried under vacuum (5 mmHg, 25° C.) to afford the title intermediate mixture (33.4 g, 73.7% yield) as a white solid; normal phase HPLC analysis having the following parameters:

i. Eluent: Hexanes:EtOH:AcOH (90:10:0.1), isocratic elution
  ii. Column: Luna, 4.6×150 mm 3 micron, Silica (2), 100 Å, Part Number: 00E-4162-E0
  iii. Detection wavelength (λ) 210 nm
  iv. Result:

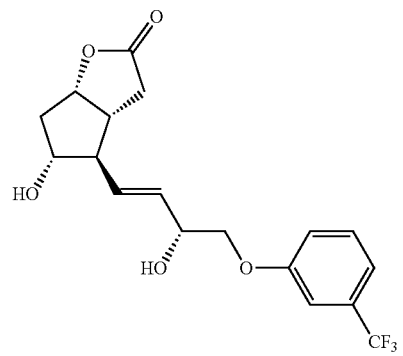
(4b)
retention time ($t_r$) = 26.094 minutes (min)

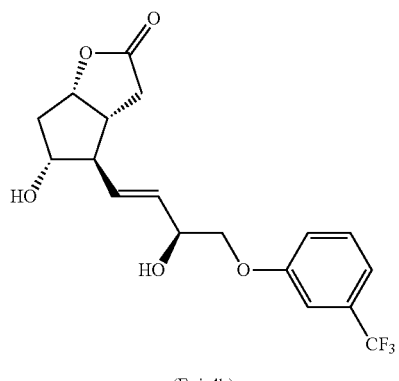
(Epi-4b)
$t_r$ = 29.756 min (4b)/(Epi-4b)
(99.21/0.79 mixture)

Step H: Preparation of highly pure (3aR,4R,5R,6aS)-5-(tert-butyldimethylsilyloxy)-4-((R,E)-3-(tert-butyldimethylsilyloxy)-4-(3-(trifluoromethyl)phenoxy)but-1-enyl)hexahydro-2H-cyclopenta[b]furan-2-one (1b) from the (4b)/(Epi-4-b) mixture

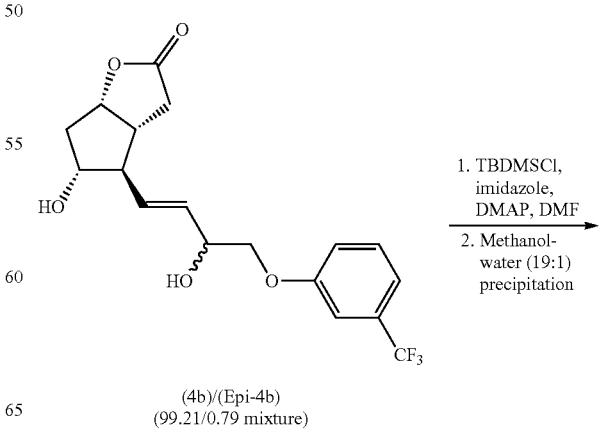

(4b)/(Epi-4b)
(99.21/0.79 mixture)

1. TBDMSCl, imidazole, DMAP, DMF
2. Methanol-water (19:1) precipitation

-continued

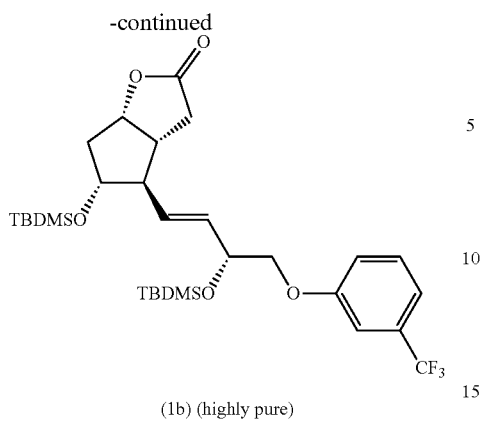

(1b) (highly pure)

To a 1-L three-necked flask fitted with a mechanical stirrer and a thermocouple were charged a mixture comprising (4b)/(Epi-4-b) (prepared in Step G, 25 g, 0.067 mol, 1.0 molar equivalent), imidazole (16 g, 0.24 mol, 3.5 molar equivalent), DMAP (2.2 g, 0.018 mole, 0.3 molar equivalent), and TBDMSCl (25.3 g, 0.168 mol, 2.5 molar equivalent) as solids. N,N-Dimethylformamide (250 mL) was added and the resulting mixture was stirred at room temperature. After 15 hours of stirring, the solids had completely dissolved and the reaction was complete, as judged by TLC. The mixture was diluted with heptanes (250 mL) and cooled to 5.0° C. with an ice-water bath. The mixture was subsequently treated with 5% w/w aqueous citric acid (375 mL). An exotherm to 24° C. was noticed. The cold bath was withdrawn. The layers of the biphasic mixture were separated (pH of lower aqueous layer: 5.5-6). The lower aqueous layer was reextracted with heptanes-ethyl acetate [(1:1), 250 mL]. The combined upper organic layers were concentrated in vacuo (20-25 mmHg, bath at 30-35° C.) to afford a solid residue. The solid residue was dissolved in methanol (365 mL). The resulting solution was transferred to a 1-L three-necked flask fitted with a mechanical stirrer and a thermocouple. Water (30 mL) was added via 60-mL addition funnel over 5 minutes. A white solid precipitated. The white solid was filtered on a medium porosity (10-16 μm) fritted glass funnel, rinsed with two 50-mL portions of water, collected, and dried under vacuum (5 mmHg, 50° C.) for 48 hours to afford the title compound (36.1 g, 89.4% yield) as a white solid; melting point 91-93° C.; $^1$H NMR (400 MHz, CDCl$_3$) δ 7.38 (t, J=8.06 Hz, 1H), 7.20 (d, J=7.57 Hz, 1H), 7.08 (s, 1H), 7.04 (d, J=8.3 Hz, 1H), 5.64 (m, 2H), 4.94 (td, J$_1$=7.08 Hz, J$_2$=2.20 Hz, 1H), 4.51 (m, 1H), 3.99 (q, J=5.86 Hz, 1H), 3.86 (d, J=5.86 Hz, 2H), 2.75 (dd, J$_1$=17.82 Hz, J$_2$=10.01 Hz, 1H), 2.63 (qd, J$_1$=7.33, J$_2$=2.20 Hz, 1H), 2.47 (dd, J$_1$=17.82 Hz, J$_2$=2.20 Hz, 1H), 2.46 (m, 1H), 2.30 (dt, J$_1$=14.90 Hz, J$_2$=6.60 Hz, 1H), 1.97 (ddd, J$_1$=11.23 Hz, J$_2$=5.37 Hz, J$_3$=2.20 Hz, 1H), 0.90 (s, 9H), 0.87 (s, 9H), 0.09 (s, 6H), 0.05 (s, 3H), 0.04 (s, 3H).

The title product (1b) may be used to prepare PGF$_{2\alpha}$ analogs of formulas (5b) and (6b); for example, (1b) may replace (1a) in Example 3, Steps A, B, and D (skipping Step C) to prepare highly pure (+)-fluprostenol free acid. The highly pure fluprostenol free acid may be converted to highly pure (+)-fluprostenol isopropyl ester (Travoprost®) using the conditions described in Example 4, Step C, except that (+)-fluprostenol free acid is used instead of the (11a-1a)/(11a-1b) mixture.

The examples herein described purifications of "crude" (1)/(Epi-1) or (2)/(Epi-2) equimolar mixture ratios starting from >90:10 (i.e. greater than 90% in the desired stereoisomer vs. the undesired stereoisomer). These solid mixtures with (1)/(Epi-1) or (2)/(Epi-2) equimolar mixture ratios of between about 1:1 and 90:10 may also be purified by the methods described herein.

What is claimed is:
1. A method for forming a solid, highly pure compound of formula

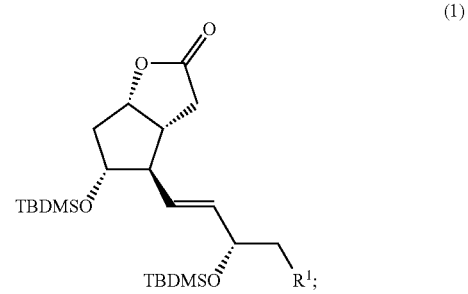

comprising:
(a) providing a compound according to formula (C1);

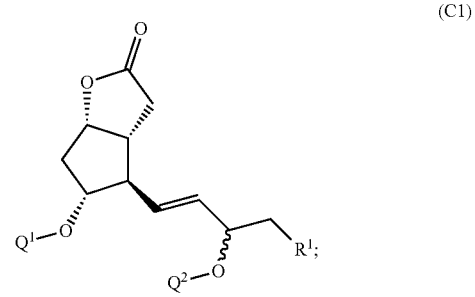

wherein:
R$^1$ is

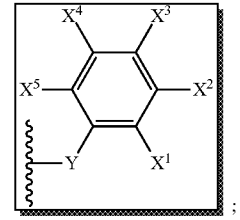

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and
each Q$^1$ and Q$^2$ is independently a protecting group that is not tert-butyldimethylsilyl (TBDMS); or wherein one of Q$^1$ and Q$^2$ is TBDMS and the other is a protecting group that is not TBDMS; or wherein one of Q$^1$ and Q$^2$ is hydrogen and the other is a protecting group that is not TBDMS;
(b) forming a compound according to formula (B1) by removing the protecting groups of Q$^1$ and Q$^2$ of said compound according to formula (C1) that are not TBDMS;

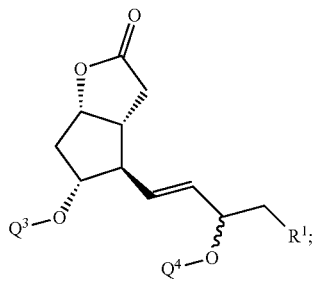

(B1)

wherein each $Q^3$ and $Q^4$ is hydrogen; or wherein one of $Q^3$ and $Q^4$ is TBDMS and the other is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

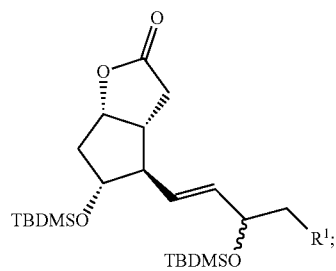

(A1)

and (d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1).

2. A method for forming a solid, highly pure compound of formula (1),

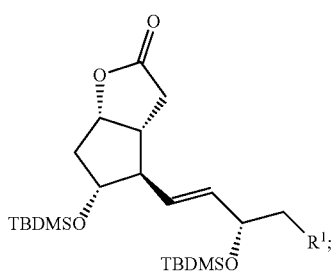

(1)

comprising:
(a) providing a compound according to formula (C1);

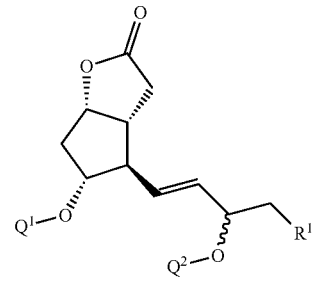

(C1)

wherein:
$R^1$ is

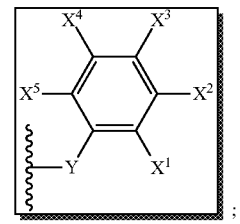

;

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1$-$C_3)$-alkyl, $(C_1$-$C_3)$-alkoxy, or $(C_1$-$C_3)$-alkylthio; and
each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;
(b) forming a compound according to formula (B1) by removing the protecting groups of $Q^1$ and $Q^2$ of said compound according to formula (C1);

(B1)

wherein each $Q^3$ and $Q^4$ is hydrogen;
(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

(A1)

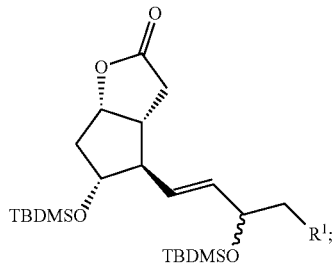

and (d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1).

3. The method of claim 2, wherein (d) purifying said compound according to formula (A1) comprises:

(e) dissolving said compound according to formula (A1) in an organic solvent to form an organic solution;

(f) adding water to said organic solution to form a solid precipitate; and (g) filtering said organic solution to isolate said solid precipitate.

4. The method of claim 3, wherein (d) purifying said compound according to formula (A1) further comprises:

(h) dissolving said isolated solid precipitate in an organic solvent to form an organic solution;

(i) adding water to said organic solution to precipitate said isolated solid precipitate; and (j) filtering said organic solution to isolate said isolated solid precipitate.

5. A method for forming a solid, highly pure compound of formula (2), (2)

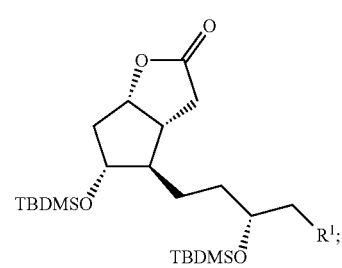

comprising:

(a) providing a compound according to formula (C1);

(C1)

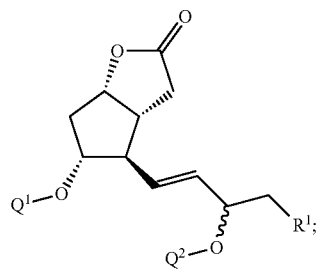

wherein:

R$^1$ is

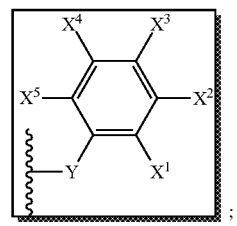

;

Y is CH$_2$, O, S, or NH;

X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and each Q$^1$ and Q$^2$ is independently a protecting group that is not tert-butyldimethylsilyl (TBDMS); or wherein one of Q$^1$ and Q$^2$ is TBDMS and the other is a protecting group that is not TBDMS; or wherein one of Q$^1$ and Q$^2$ is hydrogen and the other is a protecting group that is not TBDMS;

(b) forming a compound according to formula (B1) by removing the protecting groups of Q$^1$ and Q$^2$ from said compound according to formula (C1) that are not TBDMS;

(B1)

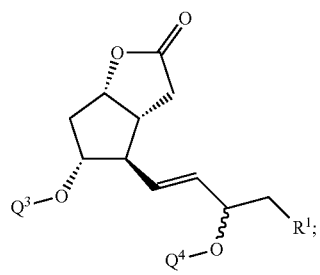

wherein each Q$^3$ and Q$^4$ is hydrogen; or wherein one of Q$^3$ and Q$^4$ is TBDMS and the other is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

(A1)

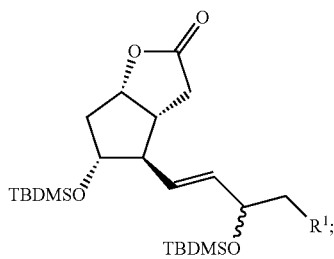

(d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1);

(1)

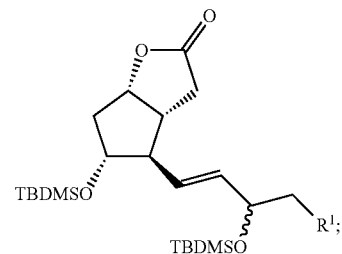

and (e) introducing elemental hydrogen to reduce a double bond on a aliphatic chain extending off a cyclopentyl ring to said compound according to formula (1) to form the compound according to formula (2).

6. A method for forming a solid, highly pure compound of formula (2), (2)

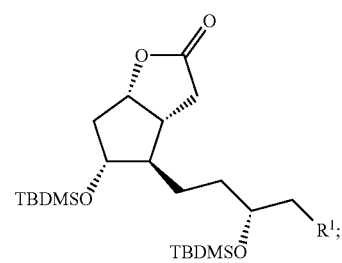

comprising:
(a) providing a compound according to formula (C1);

(C1)

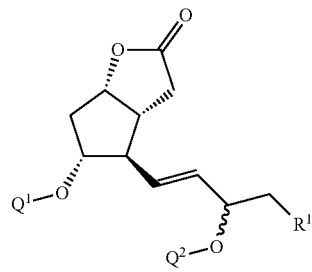

wherein:
$R^1$ is

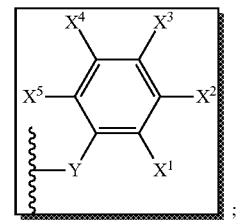

;

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and
each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;
(b) forming a compound according to formula (B1) by removing the protecting groups of $Q^1$ and $Q^2$ from said compound according to formula (C1);

(B1)

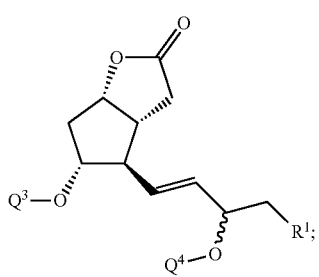

wherein each $Q^3$ and $Q^4$ is hydrogen;
(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

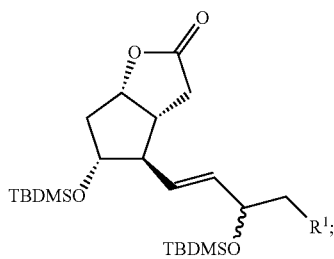

(A1)

(d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1);

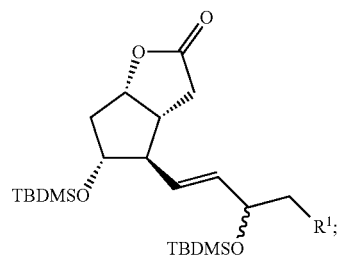

(1)

and (e) introducing elemental hydrogen to reduce a double bond on a aliphatic chain extending off a cyclopentyl ring to said compound according to formula (1) to form the compound according to formula (2).

7. The method of claim 6, wherein the steps of: (d) purifying said compound according to formula (A1) and (e) introducing elemental hydrogen comprises:

(f) dissolving said compound according to formula (A1) in an organic solvent to form an organic solution;
(g) adding water to said organic solution to form a solid precipitate of a highly pure form of said compound according to formula (1);
(h) filtering said organic solution to isolate said solid precipitate;
(i) adding elemental hydrogen or an equivalent to a solution comprising said isolated solid precipitate to reduce the carbon-carbon double bond of said isolated solid precipitate to form the compound according to formula (2);
(j) dissolving said solid precipitate of the compound according to formula (2) in an organic solvent to form an organic solution;
(k) adding water to said organic solution to precipitate said reduced and isolated solid precipitate in a highly pure form of the compound according to formula (2); and
(l) filtering said organic solution to isolate said reduced and isolated solid precipitate of the compound according to formula (2).

8. The method of claim 7, wherein the steps of: (d) purifying said compound according to formula (A1) and (e) introducing elemental hydrogen further comprises:

(m) dissolving said isolated solid precipitate of said compound according to formula (1) prior to step (i) in an organic solvent to form an organic solution;
(n) adding water to said organic solution after step (m) and prior to step (i) to precipitate said isolated solid precipitate in a highly pure form of said compound according to formula (1); and
(o) filtering said organic solution to isolate said isolated solid precipitate of said compound according to formula (1) prior to step (i) and after step (n).

9. The method of claim 7 wherein the steps of: (d) purifying said compound according to formula (A1) and (e) introducing elemental hydrogen further comprises:

(m) dissolving said reduced and isolated solid precipitate of the compound of formula (2) in an organic solvent to form an organic solution;
(n) adding water to said organic solution to reprecipitate said dissolved reduced and isolated solid precipitate of the compound of formula (2); and
(o) isolating said reprecipitated precipitate of the compound of formula (2).

10. The method of claim 8 wherein the steps of: (d) purifying said compound according to formula (A1) and (e) introducing elemental hydrogen further comprises:

(p) dissolving said reduced and isolated solid precipitate of the compound of formula (2) in an organic solvent to form an organic solution;
(q) adding water to said organic solution to reprecipitate said dissolved reduced and isolated solid precipitate of the compound of formula (2); and
(r) isolating said reprecipitated precipitate of the compound of formula (2).

11. A method for forming a solid, highly pure compound of formula (2),

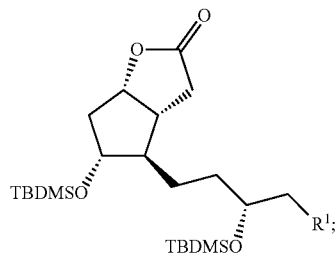

(2)

comprising:

(a) providing a compound according to formula (C1);

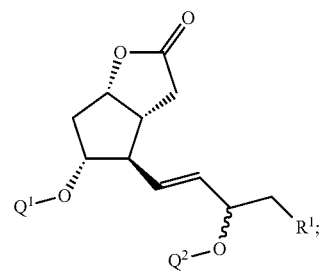

(C1)

wherein:

R[1] is

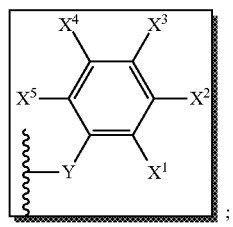

Y is CH$_2$, O, S, or NH;

X[1], X[2], X[3], X[4], and X[5] are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and each Q[1] and Q[2] is independently a protecting group that is not tert-butyldimethylsilyl (TBDMS); or wherein one of Q[1] and Q[2] is TBDMS and the other is a protecting group that is not TBDMS; or wherein one of Q[1] and Q[2] is hydrogen and the other is a protecting group that is not TBDMS;

(b) introducing elemental hydrogen to reduce a double bond on a aliphatic chain extending off a cyclopentyl ring to said compound according to formula (C1) to form the compound according to formula (C2);

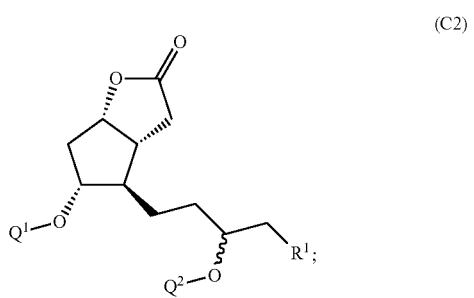

(c) forming a compound according to formula (B2) by removing the protecting groups of Q[1] and Q[2] from said compound according to formula (C2) that are not TBDMS;

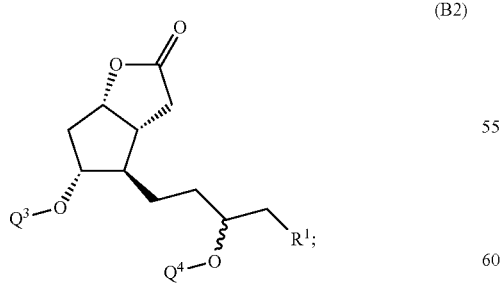

wherein each Q[3] and Q[4] is hydrogen; or wherein one of Q[3] and Q[4] is TBDMS and the other is hydrogen;

(d) transforming said compound according to formula (B2) to a compound according to formula (A2) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

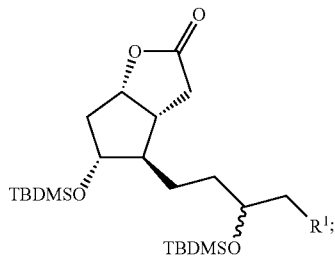

and (e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

12. A method for forming a solid, highly pure compound of formula (2),

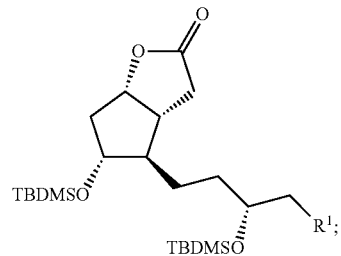

comprising:

(a) providing a compound according to formula (C1);

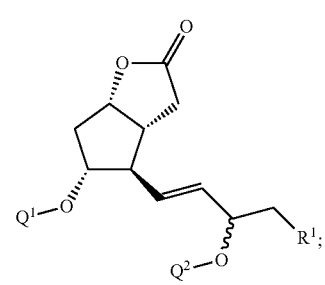

wherein:

R¹ is

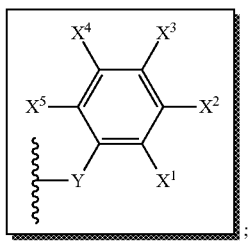

Y is CH₂, O, S, or NH;

X¹, X², X³, X⁴, and X⁵ are independently hydrogen, halo, trifluoromethyl, hydroxy, trifluoromethoxy, (C₁-C₃)-alkyl, (C₁-C₃)-alkoxy, or (C₁-C₃)-alkylthio; and each Q¹ and Q² is independently a protecting group that is not tert-butyldimethylsilyl (TBDMS); or wherein one of Q¹ and Q² is TBDMS and the other is a protecting group that is not TBDMS; or wherein one of Q¹ and Q² is hydrogen and the other is a protecting group that is not TBDMS;

(b) introducing elemental hydrogen to reduce a double bond on a aliphatic chain extending off a cyclopentyl ring to said compound according to formula (C1) to form the compound according to formula (C2);

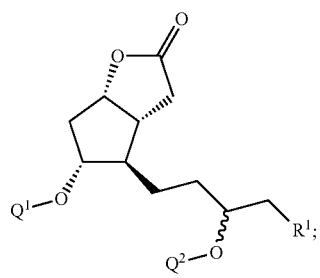
(C2)

(c) forming a compound according to formula (B2) by removing the protecting groups of Q¹ and Q² from said compound according to formula (C2);

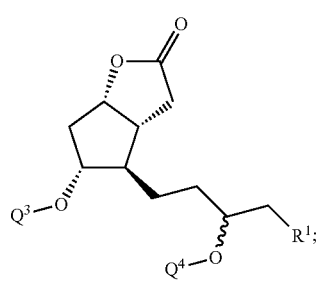
(B2)

wherein each Q³ and Q⁴ is hydrogen;

(d) transforming said compound according to formula (B2) to a compound according to formula (A2) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

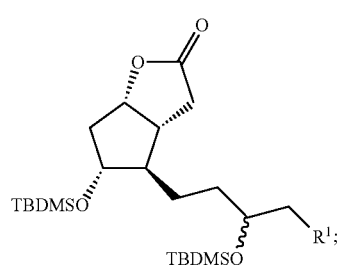
(A2)

and (e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

13. A method for forming a solid, highly pure compound of formula (2):

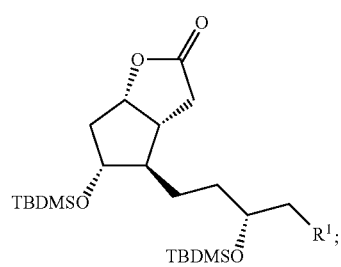
(2)

comprising:

(a) providing a compound according to formula (C1);

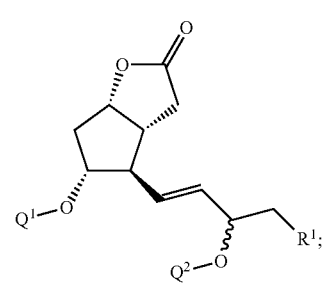
(C1)

wherein:

R¹ is

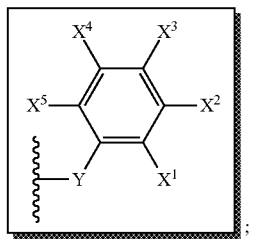

Y is CH₂, O, S, or NH;

X¹, X², X³, X⁴, and X⁵ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and each Q¹ and Q² is independently a protecting group that is not tert-butyldimethylsilyl (TBDMS); or wherein one of Q¹ and Q² is TBDMS and the other is a protecting group that is not TBDMS; or wherein one of Q¹ and Q² is hydrogen and the other is a protecting group that is not TBDMS;

(b) forming a compound according to formula (B1) by removing the protecting groups of Q¹ and Q² from said compound according to formula (C1) that are not TBDMS;

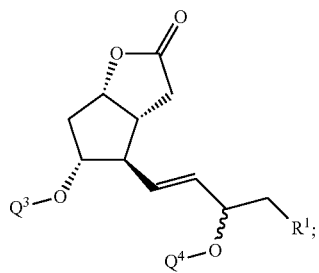

(B1)

wherein each Q³ and Q⁴ is hydrogen; or wherein one of Q³ and Q⁴ is TBDMS and the other is hydrogen;

(c) introducing elemental hydrogen to reduce a double bond on a aliphatic chain extending off a cyclopentyl ring to said compound according to formula (B1) to form the compound according to formula (B2);

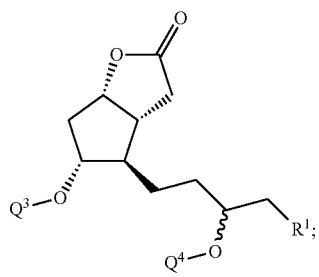

(B2)

(d) transforming said compound according to formula (B2) to a compound according to formula (A2) by the step of tert-butyldimethylsilylation, wherein said compound according to formula (A2) includes a mixture of α-OTBDMS and β-OTBDMS on its aliphatic chain, said mixture therefore defining an aliphatic chain α-OTBDMS/β-OTBDMS mixture ratio;

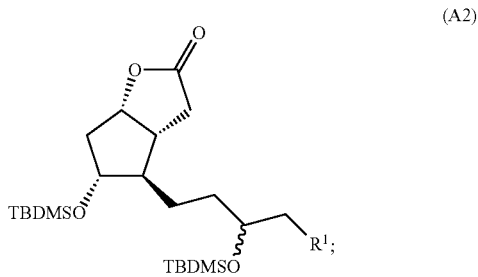

(A2)

and (e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

14. A method for forming a solid, highly pure compound of formula (2):

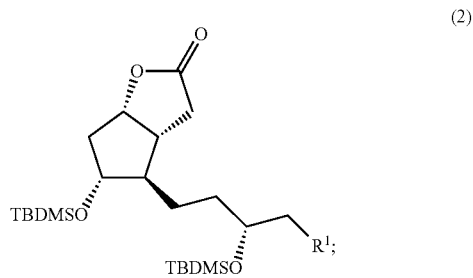

(2)

comprising:

(a) providing a compound according to formula (C1);

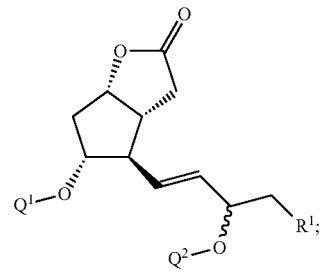

(C1)

wherein:

R[1] is

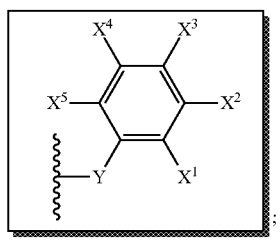

Y is $CH_2$, O, S, or NH;

X[1], X[2], X[3], X[4], and X[5] are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and each Q[1] and Q[2] is independently a protecting group that is not tert-butyldimethylsilyl (TBDMS); or wherein one of Q[1] and Q[2] is TBDMS and the other is a protecting group that is not TBDMS; or wherein one of Q[1] and Q[2] is hydrogen and the other is a protecting group that is not TBDMS;

(b) forming a compound according to formula (B1) by removing the protecting groups of Q[1] and Q[2] from said compound according to formula (C1);

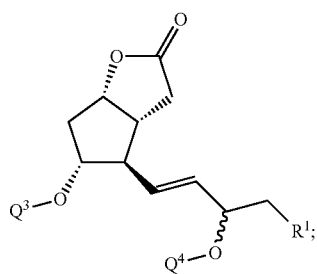

(B1)

wherein each Q[3] and Q[4] is hydrogen;

(c) introducing elemental hydrogen to reduce a double bond on a aliphatic chain extending off a cyclopentyl ring to said compound according to formula (B1) to form the compound according to formula (B2);

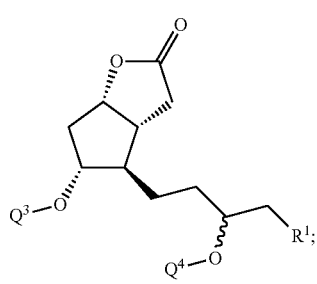

(B2)

(d) transforming said compound according to formula (B2) to a compound according to formula (A2) by the step of tert-butyldimethylsilylation, wherein said compound according to formula (A2) includes a mixture of α-OTBDMS and β-OTBDMS on its aliphatic chain, said mixture therefore defining an aliphatic chain α-OTBDMS/β-OTBDMS mixture ratio;

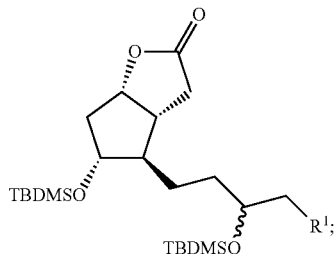

(A2)

and (e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

15. A method for forming a solid, highly pure compound of formula (2),

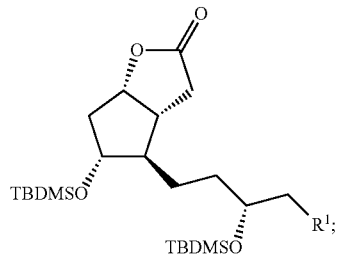

(2)

comprising:

(a) providing a compound according to formula (C1);

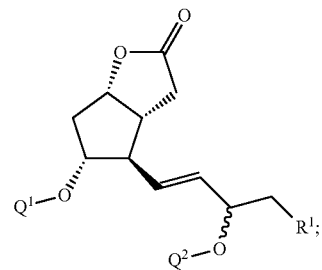

(C1)

wherein:
R[1] is

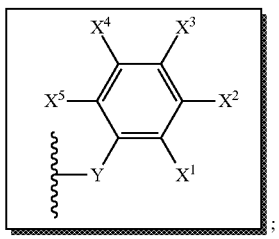
;

Y is CH$_2$, O, S, or NH;
X[1], X[2], X[3], X[4], and X[5] are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and
each Q[1] and Q[2] is independently a protecting group that is not tert-butyldimethylsilyl (TBDMS); or wherein one of Q[1] and Q[2] is TBDMS and the other is a protecting group that is not TBDMS; or wherein one of Q[1] and Q[2] is hydrogen and the other is a protecting group that is not TBDMS;
(b) forming a compound according to formula (B1) by removing the protecting groups of Q[1] and Q[2] from said compound according to formula (C1) that are not TBDMS;

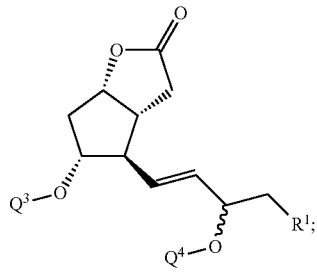
(B1)

wherein each Q[3] and Q[4] is hydrogen; or wherein one of Q[3] and Q[4] is TBDMS and the other is hydrogen;
(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

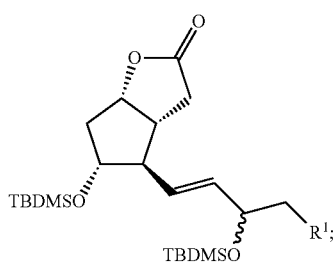
(A1)

(d) introducing elemental hydrogen to reduce a double bond on a aliphatic chain extending off a cyclopentyl ring to said compound according to formula (A1) to form the compound according to formula (A2);

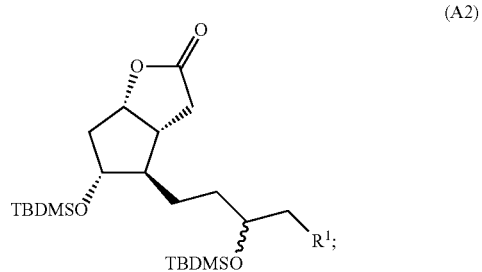
(A2)

and
(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

16. A method for forming a solid, highly pure compound of formula (2),

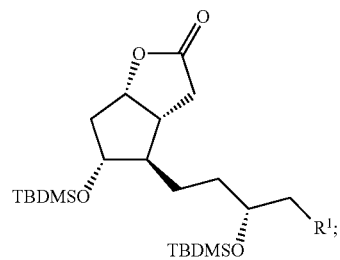
(2)

comprising:
(a) providing a compound according to formula (C1);

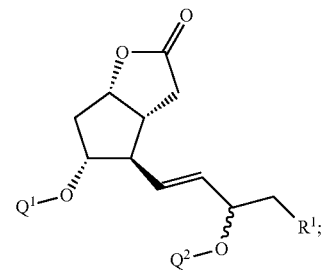
(C1)

wherein:
R$^1$ is

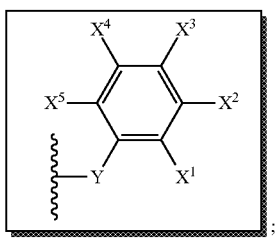

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and
each Q$^1$ and Q$^2$ is independently a protecting group that is not tert-butyldimethylsilyl (TBDMS); or wherein one of Q$^1$ and Q$^2$ is TBDMS and the other is a protecting group that is not TBDMS; or wherein one of Q$^1$ and Q$^2$ is hydrogen and the other is a protecting group that is not TBDMS;

(b) forming a compound according to formula (B1) by removing the protecting groups of Q$^1$ and Q$^2$ from said compound according to formula (C1);

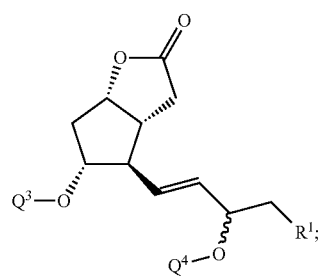

(B1)

wherein each Q$^3$ and Q$^4$ is hydrogen;
(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

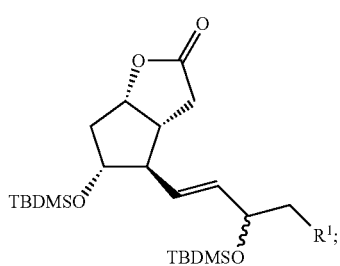

(A1)

(d) introducing elemental hydrogen to reduce a double bond on a aliphatic chain extending off a cyclopentyl ring to said compound according to formula (A1) to form the compound according to formula (A2);

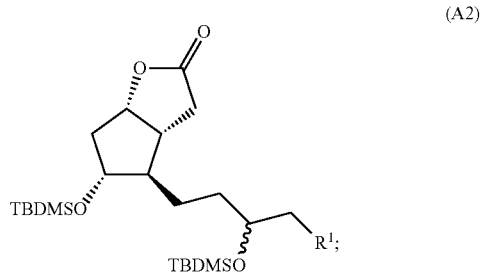

(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2).

17. A method of forming a high purity prostaglandin F$_{2\alpha}$ analog of structural formula (5) comprising:
(a) providing a compound according to formula (C1);

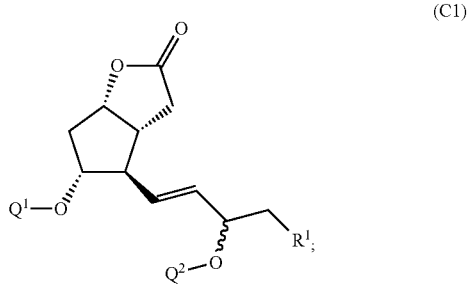

(C1)

wherein:
R$^1$ is

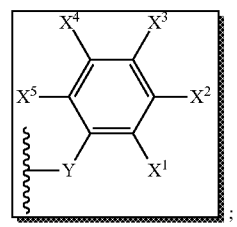

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio; and
each Q$^1$ and Q$^2$ is independently a protecting group that is not tert-butyldimethylsilyl (TBDMS); or wherein one of Q$^1$ and Q$^2$ is TBDMS and the other is a protecting group that is not TBDMS; or wherein one of Q$^1$ and Q$^2$ is hydrogen and the other is a protecting group that is not TBDMS;

(b) forming a compound according to formula (B1) by removing the protecting groups of $Q^1$ and $Q^2$ of said compound according to formula (C1) that are not TBDMS;

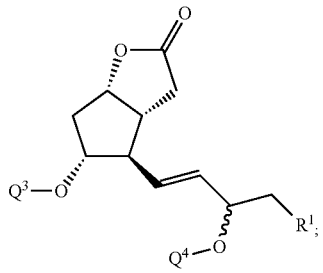
(B1)

wherein each $Q^3$ and $Q^4$ is hydrogen; or wherein one of $Q^3$ and $Q^4$ is TBDMS and the other is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

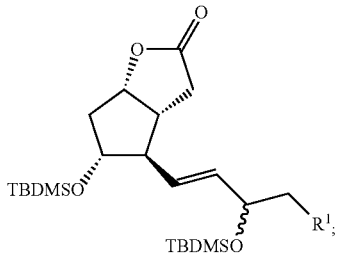
(A1)

and (d) purifying said compound according to formula (A1) by forming a solid precipitate comprising a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1), wherein purifying said compound according to formula (A1) comprises:

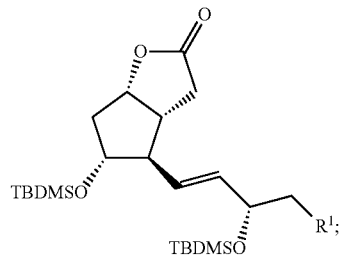
(1)

(aa) dissolving said compound according to formula (A1) in an organic solvent to form an organic solution;
(bb) adding water to said organic solution to form a solid precipitate;

(cc) filtering said organic solution to isolate said solid precipitate;

(e) performing a lactone reduction of said solid precipitate of a compound according to formula (1) to form a compound according to formula (7);

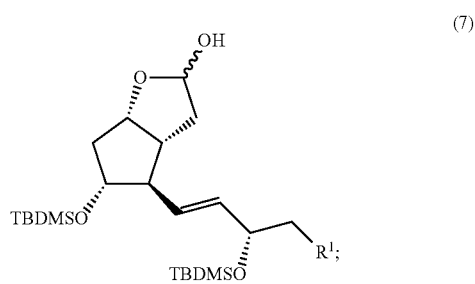
(7)

(f) reacting said compound according to formula (7) with (4-carboxybutyl)triphenylphosphonium bromide in the presence of an excess base to form a mixture comprising a compound according to formula (8-1a) and a compound according to formula (8-1b);

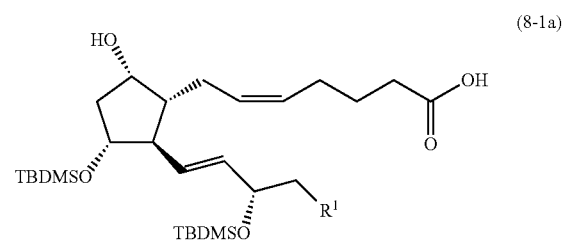
(8-1a)

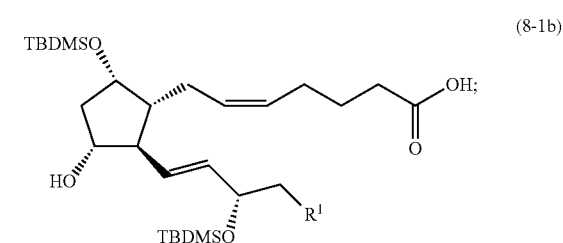
(8-1b)

(g) treating said mixture to convert the carboxylic acid moiety to other functional groups $R^2$ to form a mixture comprising a compound according to formula (9-Xa) and a compound according to formula (9-Xb);

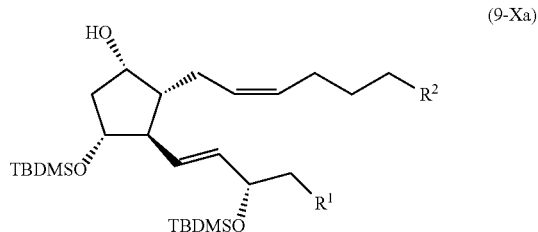
(9-Xa)

-continued

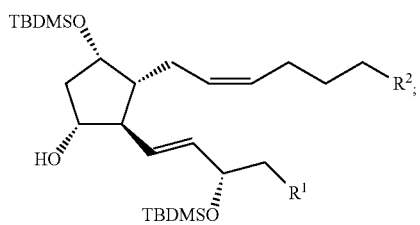

(9-Xb)

wherein:
R² is —CO₂R³, —CONR⁴R⁵, —C(O)R³, —C(O)CH₂X⁶, or —CH₂X⁶;
X⁶ is halo or —OR³
R³ is hydrogen, (C₁-C₆)-alkyl, or —(CH₂)ₙ-phenyl;
R⁴ and R⁵ are independently hydrogen, (C₁-C₆)-alkyl, or —(CH₂)ₙ-phenyl;
n is 0, 1, or 2; and
any phenyl of R³, R⁴ or R⁵ may be optionally substituted with one or more of any one or combination of halo, trifluoromethyl, hydroxy, trifluoromethoxy, amino, cyano, (C₁-C₆)-alkyl, (C₁-C₆)-alkoxy, or (C₁-C₆)-alkylthio;

and (h) deprotecting said mixture comprising said compound according to formula (9-Xa) and said compound according to formula (9-Xb) to form a prostaglandin F₂α analog of structural formula (5):

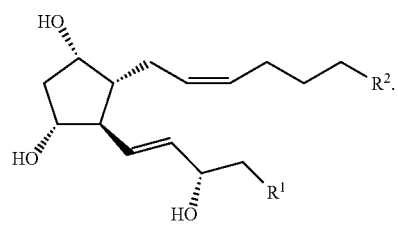

(5)

18. A method of forming a high purity prostaglandin F₂α analog of structural formula (5) comprising:

(a) providing a compound according to formula (C1):

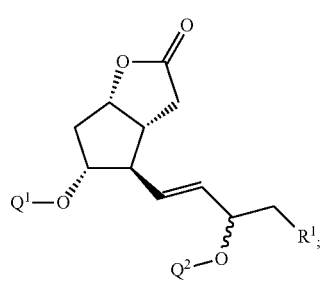

(C1)

wherein:
R¹ is

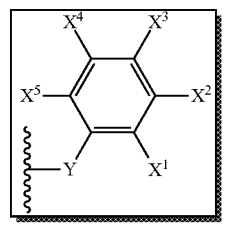

;

Y is CH₂, O, S, or NH;
X¹, X², X³, X⁴, and X⁵ are independently hydrogen, halo, trifluoromethyl, hydroxy, trifluoromethoxy, (C₁-C₃)-alkyl, (C₁-C₃)-alkoxy, or (C₁-C₃)-alkylthio; and
each Q¹ and Q² is independently a protecting group that is not tert-butyldimethylsilyl (TBDMS); or wherein one of Q¹ and Q² is TBDMS and the other is a protecting group that is not TBDMS; or wherein one of Q¹ and Q² is hydrogen and the other is a protecting group that is not TBDMS;

(b) forming a compound according to formula (B1) by removing the protecting groups of Q¹ and Q² of said compound according to formula (C1);

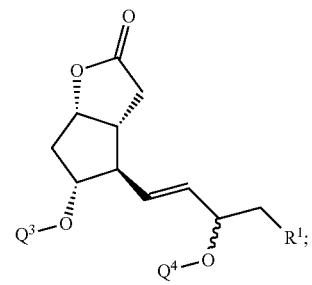

(B1)

wherein each Q³ and Q⁴ is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

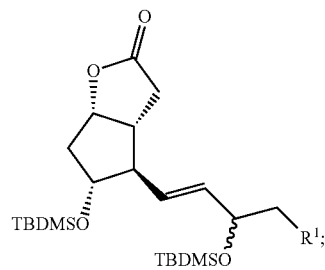

(A1)

and (d) purifying said compound according to formula (A1) by forming a solid precipitate comprising a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1), wherein purifying said compound according to formula (A1) comprises:

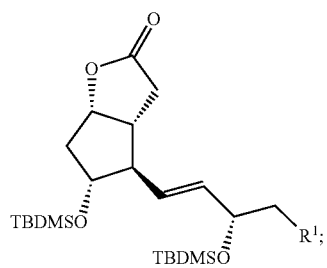

(aa) dissolving said compound according to formula (A1) in an organic solvent to form an organic solution;

(bb) adding water to said organic solution to form a solid precipitate;

(cc) filtering said organic solution to isolate said solid precipitate;

(e) performing a lactone reduction of said solid precipitate of a compound according to formula (1) to form a compound according to formula (7);

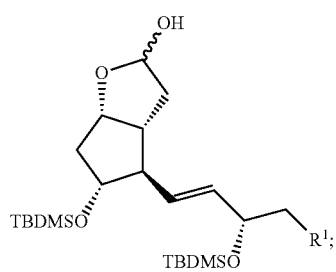

(f) reacting said compound according to formula (7) with (4-carboxybutyl)triphenylphosphonium bromide in the presence of an excess base to form a mixture comprising a compound according to formula (8-1a) and a compound according to formula (8-1b);

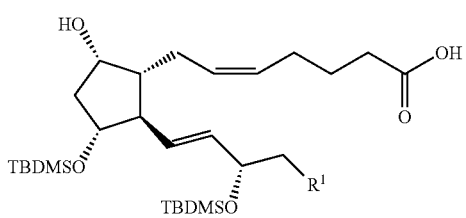

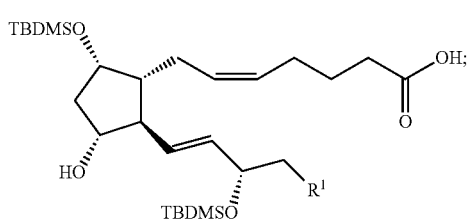

(g) treating said mixture to convert the carboxylic acid moiety to other functional groups $R^2$ to form a mixture comprising a compound according to formula (9-Xa) and a compound according to formula (9-Xb);

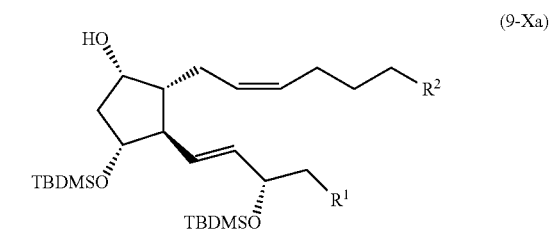

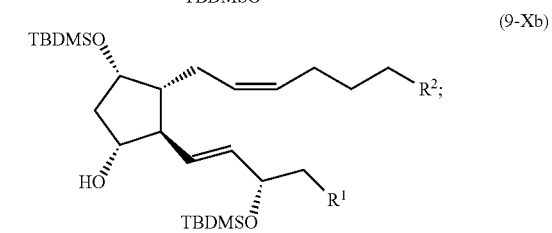

wherein:
$R^2$ is —$CO_2R^3$, —$CONR^4R^5$, —$C(O)R^3$, —$C(O)CH_2X^6$, or —$CH_2X^6$;
$X^6$ is halo or —$OR^3$;
$R^3$ is hydrogen, $(C_1-C_6)$-alkyl, or —$(CH_2)_n$-phenyl;
$R^4$ and $R^5$ are independently hydrogen, $(C_1-C_6)$-alkyl, or —$(CH_2)_n$-phenyl;
n is 0, 1, or 2; and
any phenyl of $R^3$, $R^4$ or $R^5$ may be optionally substituted with one or more of any one or combination of halo, trifluoromethyl, hydroxy, trifluoromethoxy, amino, cyano, $(C_1-C_6)$-alkyl, $(C_1-C_6)$-alkoxy, or $(C_1-C_6)$-alkylthio;
and
(h) deprotecting said mixture comprising said compound according to formula (9-Xa) and said compound according to formula (9-Xb) to form a prostaglandin $F_{2\alpha}$ analog of structural formula (5):

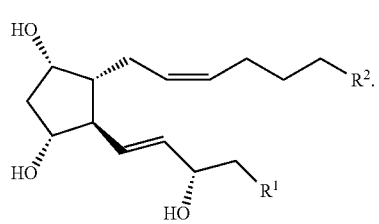

19. The method of claim 17, wherein (d) purifying said compound according to formula (A1) further comprises:

(dd) dissolving said isolated solid precipitate in an organic solvent to form an organic solution;

(ee) adding water to said organic solution to precipitate said isolated solid precipitate; and (ff) filtering said organic solution to isolate said isolated solid precipitate.

20. The method of claim 18, wherein (d) purifying said compound according to formula (A1) further comprises:

(dd) dissolving said isolated solid precipitate in an organic solvent to form an organic solution;

(ee) adding water to said organic solution to precipitate said isolated solid precipitate; and (ff) filtering said organic solution to isolate said isolated solid precipitate.

21. A method of forming a high purity prostaglandin $F_{2\alpha}$ analog of structural formula (6) comprising:

(a) providing a compound according to formula (C1):

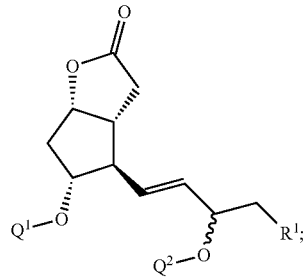

(C1)

wherein:

$R^1$ is

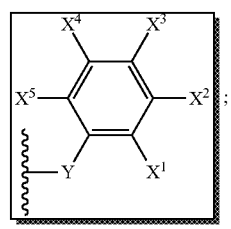

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1) that are not TBDMS;

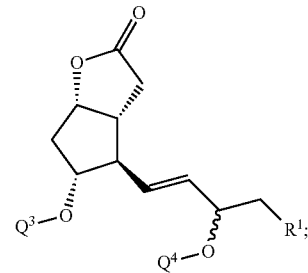

(B1)

wherein each $Q^3$ and $Q^4$ is hydrogen; or wherein one of $Q^3$ and $Q^4$ is TBDMS and the other is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

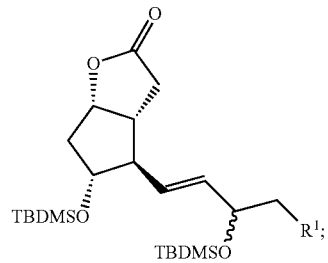

(A1)

(d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1);

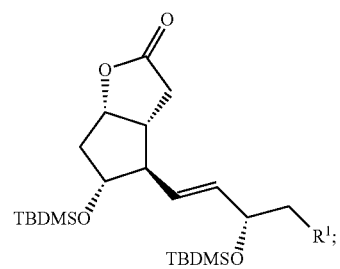

(1)

(e) introducing elemental hydrogen to reduce a double bond on a aliphatic chain extending off a cyclopentyl ring to said compound according to formula (1) to form the compound according to formula (2);

(2)

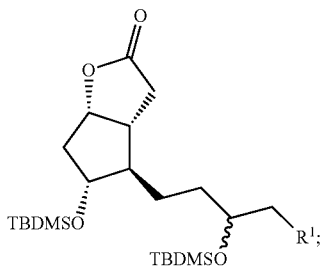

wherein:

R¹ is

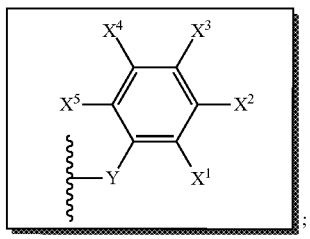

Y is CH₂, O, S, or NH;

X¹, X², X³, X⁴, and X⁵ are independently hydrogen, halo, trifluoromethyl, hydroxy, trifluoromethoxy, (C₁-C₃)-alkyl, (C₁-C₃)-alkoxy, or (C₁-C₃)-alkylthio;

(f) performing a lactone reduction of said solid compound according to formula (1) to form a compound according to formula (10);

(10)

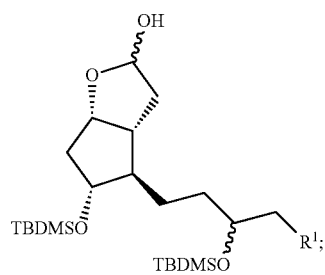

(g) reacting said compound according to formula (10) with (4-carboxybutyl)triphenylphosphonium bromide in the presence of an excess base to form a mixture comprising a compound according to formula (11-1a) and a compound according to formula (11-1b);

(11-1a)

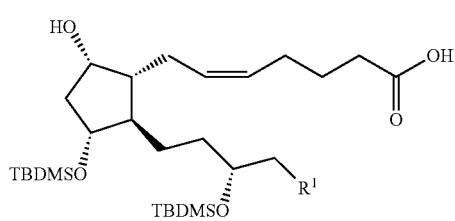

(11-1b)

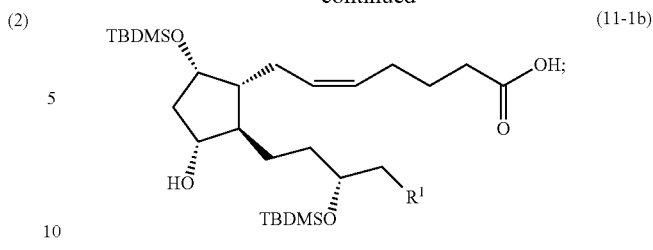

(h) treating said mixture to convert the carboxylic acid moiety to other functional groups R² to form a mixture comprising a compound according to formula (12-Xa) and a compound according to formula (12-Xb);

(12-Xa)

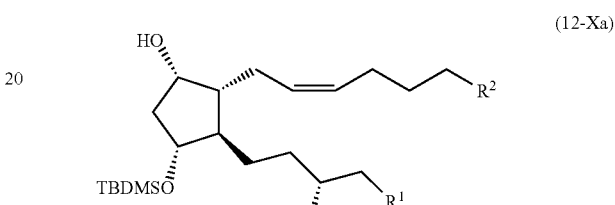

(12-Xb)

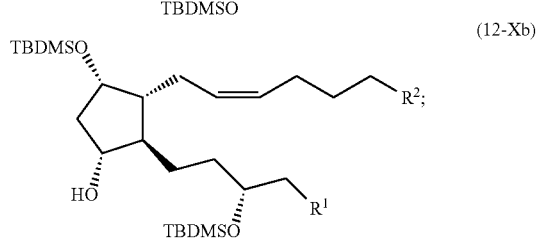

wherein:

R² is —CO₂R³, —CONR⁴R⁵, —C(O)R³, —C(O)CH₂X⁶, or —CH₂X⁶;

X⁶ is halo or —OR³

R³ is hydrogen, (C₁-C₆)-alkyl, or —(CH₂)ₙ-phenyl;

R⁴ and R⁵ are independently hydrogen, (C₁-C₆)-alkyl, or —(CH₂)ₙ-phenyl;

n is 0, 1, or 2; and any phenyl of R³, R⁴ or R⁵ may be optionally substituted with one or more of any one or combination of halo, trifluoromethyl, hydroxy, trifluoromethoxy, amino, cyano, (C₁-C₆)-alkyl, (C₁-C₆)-alkoxy, or (C₁-C₆)-alkylthio;

and (i) deprotecting said mixture comprising said compound according to formula (12-Xa) and said compound according to formula (12-Xb) to form a prostaglandin F₂α analog of structural formula (6):

(6)

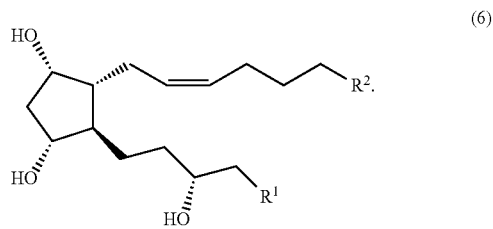

22. A method of forming a high purity prostaglandin $F_{2\alpha}$ analog of structural formula (6) comprising:

(a) providing a compound according to formula (C1):

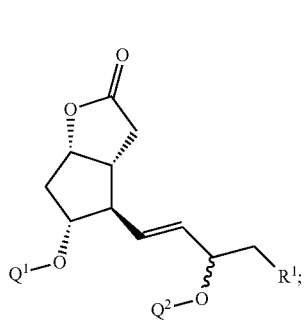
(C1)

wherein:
$R^1$ is

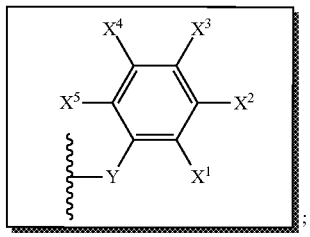

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1\text{-}C_3)$-alkyl, $(C_1\text{-}C_3)$-alkoxy, or $(C_1\text{-}C_3)$-alkylthio; and
each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1);

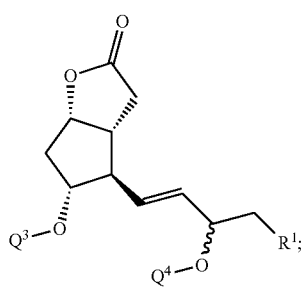
(B1)

wherein each $Q^3$ and $Q^4$ is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio; and

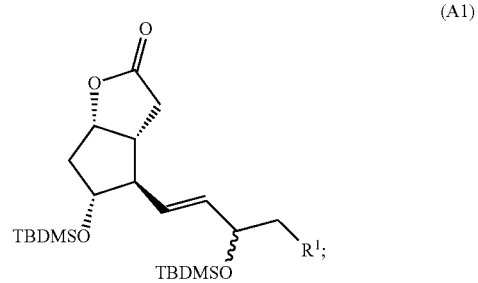
(A1)

(d) purifying said compound according to formula (A1) to form a solid precipitate of a compound according to formula (1), said solid precipitate of said compound according to formula (1) having a higher aliphatic chain α-OTBDMS/β-OTBDMS mixture ratio than said α-OTBDMS/β-OTBDMS ratio of said compound according to formula (A1);

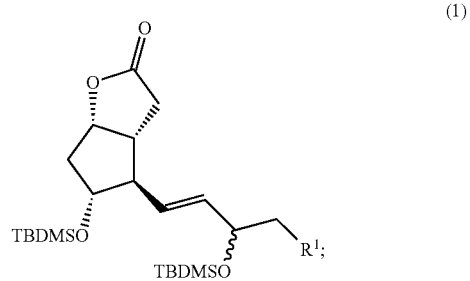
(1)

(e) introducing elemental hydrogen to reduce a double bond on a aliphatic chain extending off a cyclopentyl ring to said compound according to formula (1) to form the compound according to formula (2);

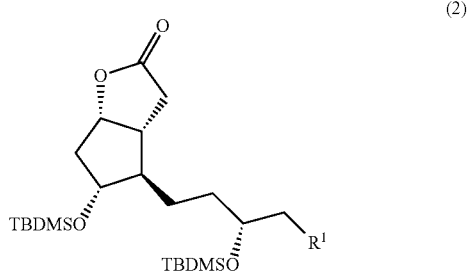
(2)

wherein:

R¹ is

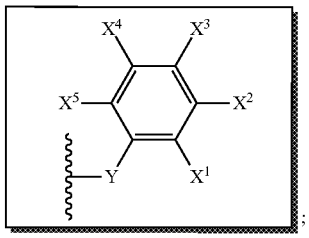

Y is CH₂, O, S, or NH;

X¹, X², X³, X⁴, and X⁵ are independently hydrogen, halo, trifluoromethyl, hydroxy, trifluoromethoxy, (C₁-C₃)-alkyl, (C₁-C₃)-alkoxy, or (C₁-C₃)-alkylthio;

(f) performing a lactone reduction of said solid compound according to formula (1) to form a compound according to formula (10);

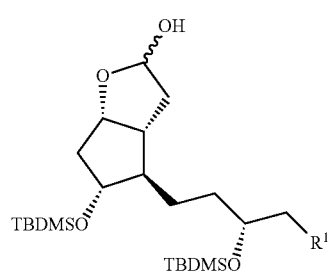

(g) reacting said compound according to formula (10) with (4-carboxybutyl)triphenylphosphonium bromide in the presence of an excess base to form a mixture comprising a compound according to formula (11-1a) and a compound according to formula (11-1b);

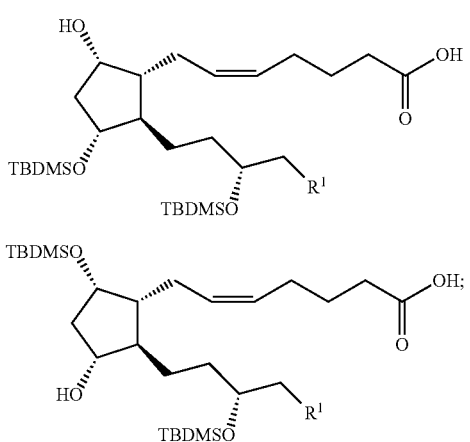

(h) treating said mixture to convert the carboxylic acid moiety to other functional groups R² to form a mixture comprising a compound according to formula (12-Xa) and a compound according to formula (12-Xb);

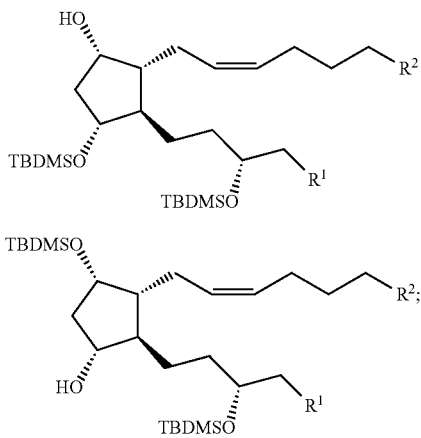

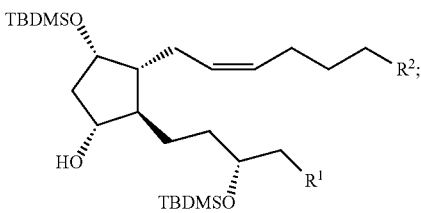

wherein:
R² is —CO₂R³, —CONR⁴R⁵, —C(O)R³, —C(O)CH₂X⁶, or —CH₂X⁶;
X⁶ is halo or —OR³
R³ is hydrogen, (C₁-C₆)-alkyl, or —(CH₂)ₙ-phenyl;
R⁴ and R⁵ are independently hydrogen, (C₁-C₆)-alkyl, or —(CH₂)ₙ-phenyl;
n is 0, 1, or 2; and
  any phenyl of R³, R⁴ or R⁵ may be optionally substituted with one or more of any one or combination of halo, trifluoromethyl, hydroxy, trifluoromethoxy, amino, cyano, (C₁-C₆)-alkyl, (C₁-C₆)-alkoxy, or (C₁-C₆)-alkylthio;
and
(i) deprotecting said mixture comprising said compound according to formula (12-Xa) and said compound according to formula (12-Xb) to form a prostaglandin F₂α analog of structural formula (6):

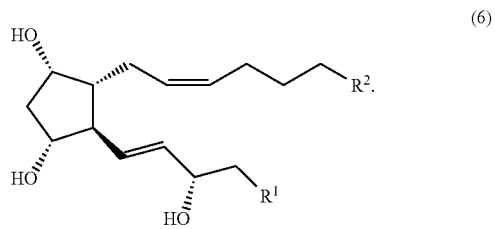

23. The method of claim 22, wherein the steps of: (d) purifying said compound according to formula (A1) and (e) introducing elemental hydrogen comprises:

(k) dissolving said compound according to formula (A1) in an organic solvent to form an organic solution;
(l) adding water to said organic solution to form a solid precipitate of a highly pure form of said compound according to formula (1);
(m) filtering said organic solution to isolate said solid precipitate;
(n) adding elemental hydrogen or an equivalent to a solution comprising said isolated solid precipitate to reduce the carbon-carbon double bond of said isolated solid precipitate to form the compound according to formula (2);
(o) dissolving said solid precipitate of the compound according to formula (2) in an organic solvent to form an organic solution;

(p) adding water to said organic solution to precipitate said reduced and isolated solid precipitate in a highly pure form of the compound according to formula (2); and (q) filtering said organic solution to isolate said reduced and isolated solid precipitate of the compound according to formula (2).

24. The method of claim 23, wherein the steps of: (d) purifying said compound according to formula (A1) and (e) introducing elemental hydrogen further comprises:

(r) dissolving said isolated solid precipitate of said compound according to formula (1) prior to step (d) in an organic solvent to form an organic solution;

(s) adding water to said organic solution after step (r) and prior to step (d) to precipitate said isolated solid precipitate in a highly pure form of said compound according to formula (1); and (t) filtering said organic solution to isolate said isolated solid precipitate of said compound according to formula (1) prior to step (d) and after step (s).

25. The method of claim 23 wherein the steps of: (d) purifying said compound according to formula (A1) and (e) introducing elemental hydrogen further comprises:

(r) dissolving said reduced and isolated solid precipitate of the compound of formula (2) in an organic solvent to form an organic solution;

(s) adding water to said organic solution to reprecipitate said dissolved reduced and isolated solid precipitate of the compound of formula (2); and (t) isolating said reprecipitated precipitate of the compound of formula (2).

26. The method of claim 25 wherein the steps of: (d) purifying said compound according to formula (A1) and (e) introducing elemental hydrogen further comprises:

(u) dissolving said reduced and isolated solid precipitate of the compound of formula (2) in an organic solvent to form an organic solution;

(v) adding water to said organic solution to reprecipitate said dissolved reduced and isolated solid precipitate of the compound of formula (2); and (w) isolating said reprecipitated precipitate of the compound of formula (2).

27. A method of forming a high purity prostaglandin $F_{2\alpha}$ analog of structural formula (6) comprising:

(a) providing a compound according to formula (C1):

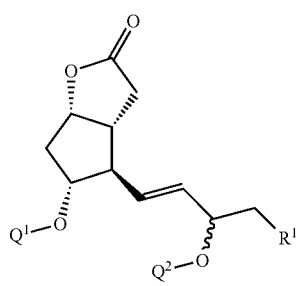

(C1)

wherein:
$R^1$ is

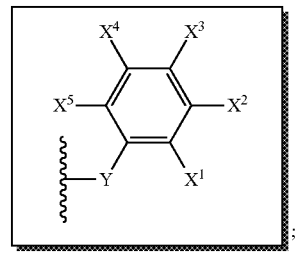

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1$-$C_3)$-alkyl, $(C_1$-$C_3)$-alkoxy, or $(C_1$-$C_3)$-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) introducing elemental hydrogen to reduce a double bond on a aliphatic chain extending off a cyclopentyl ring to said compound according to formula (C1) to form the compound according to formula (C2);

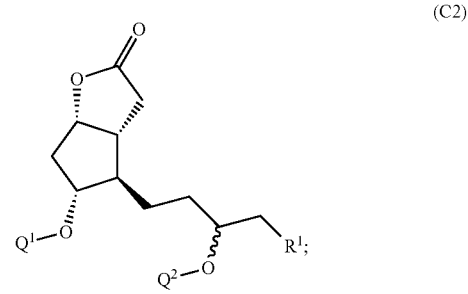

(C2)

(c) forming a compound according to formula (B2) by removing the protecting groups of $Q^1$ and $Q^2$ from said compound according to formula (C2) that are not TBDMS;

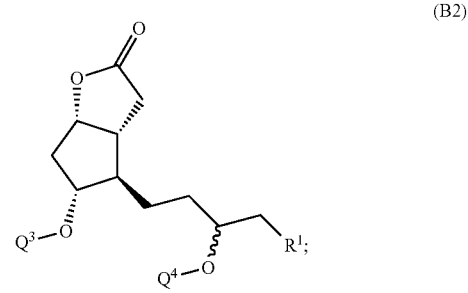

(B2)

wherein each $Q^3$ and $Q^4$ is hydrogen; or wherein one of $Q^3$ and $Q^4$ is TBDMS and the other is hydrogen;

(d) transforming said compound according to formula (B2) to a compound according to formula (A2) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

(A2)

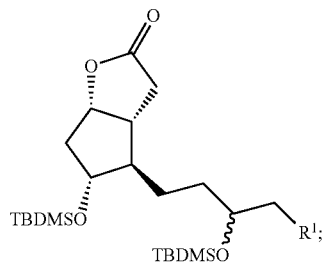

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

(2)

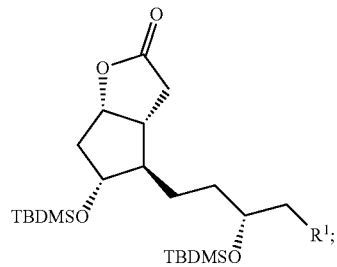

wherein:

$R^1$ is

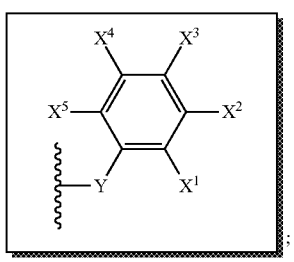

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio;

(f) performing a lactone reduction of said solid compound according to formula (1) to form a compound according to formula (10);

(10)

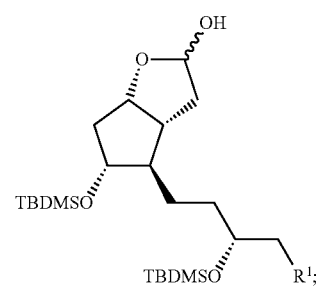

(g) reacting said compound according to formula (10) with (4-carboxybutyl)triphenylphosphonium bromide in the presence of an excess base to form a mixture comprising a compound according to formula (11-1a) and a compound according to formula (11-1b);

(11-1a)

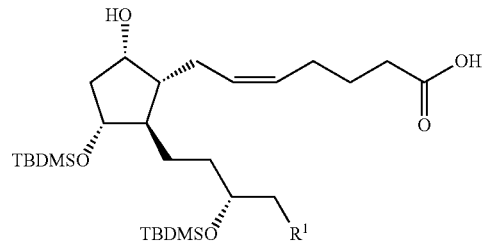

(11-1b)

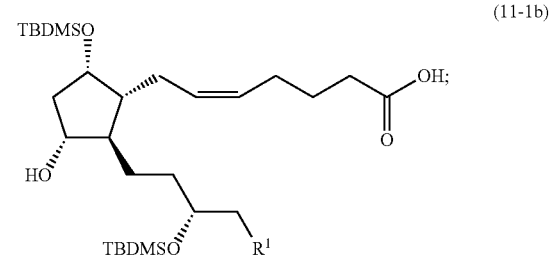

(h) treating said mixture to convert the carboxylic acid moiety to other functional groups $R^2$ to form a mixture comprising a compound according to formula (12-Xa) and a compound according to formula (12-Xb);

(12-Xa)

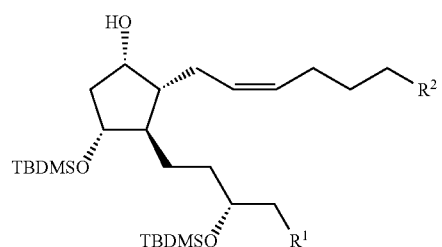

-continued

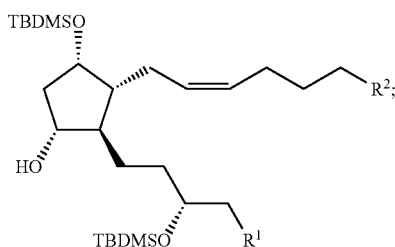

(12-Xb)

wherein:
$R^2$ is —$CO_2R^3$, —$CONR^4R^5$, —$C(O)R^3$, —$C(O)CH_2X^6$, or —$CH_2X^6$;
$X^6$ is halo or —$OR^3$
$R^3$ is hydrogen, $(C_1-C_6)$-alkyl, or —$(CH_2)_n$-phenyl;
$R^4$ and $R^5$ are independently hydrogen, $(C_1-C_6)$-alkyl, or —$(CH_2)_n$-phenyl;
n is 0, 1, or 2; and
any phenyl of $R^3$, $R^4$ or $R^5$ may be optionally substituted with one or more of any one or combination of halo, trifluoromethyl, hydroxy, trifluoromethoxy, amino, cyano, $(C_1-C_6)$-alkyl, $(C_1-C_6)$-alkoxy, or $(C_1-C_6)$-alkylthio;
and
(i) deprotecting said mixture comprising said compound according to formula (12-Xa) and said compound according to formula (12-Xb) to form a prostaglandin $F_{2\alpha}$ analog of structural formula (6):

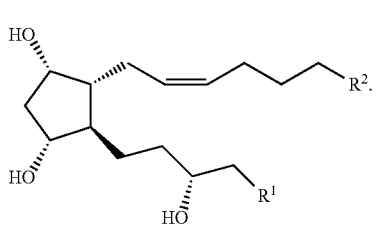

(6)

28. A method of forming a high purity prostaglandin $F_{2\alpha}$ analog of structural formula (6) comprising:
(a) providing a compound according to formula (C1):

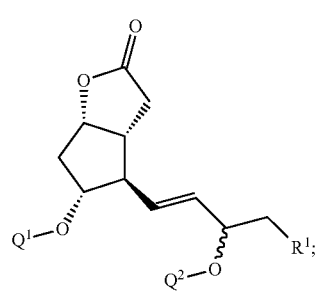

(C1)

wherein:
$R^1$ is

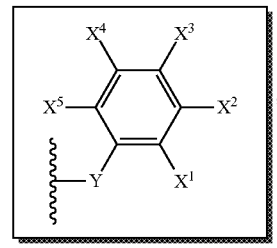

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and
each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;
(b) introducing elemental hydrogen to reduce a double bond on a aliphatic chain extending off a cyclopentyl ring to said compound according to formula (C1) to form the compound according to formula (C2);

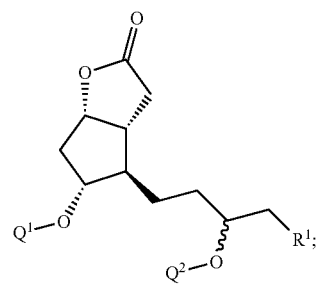

(C2)

(c) forming a compound according to formula (B2) by removing the protecting groups of $Q^1$ and $Q^2$ from said compound according to formula (C2);

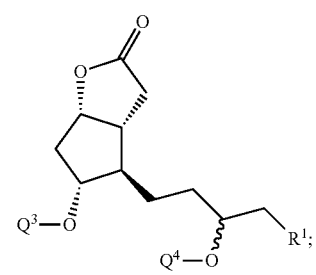

(B2)

wherein each $Q^3$ and $Q^4$ is hydrogen;
(d) transforming said compound according to formula (B2) to a compound according to formula (A2) by the step of tert-butyldimethylsilylation, wherein said compound according to formula (A2) includes a mixture of α-OT- BDMS and β-OTBDMS on its aliphatic chain, said mixture therefore defining an aliphatic chain α-OTBDMS/β-OTBDMS mixture ratio;

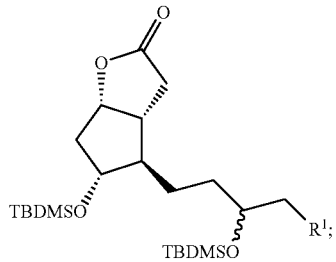

(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

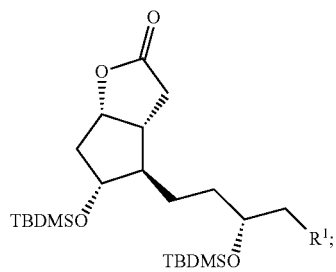

(2)

wherein:
R$^1$ is

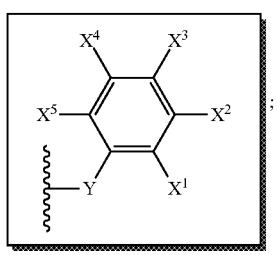

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio;

(f) performing a lactone reduction of said solid compound according to formula (1) to form a compound according to formula (10);

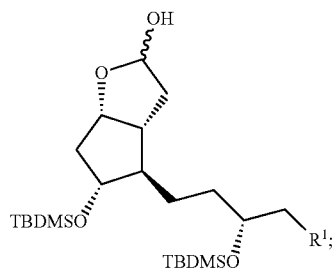

(10)

(g) reacting said compound according to formula (10) with (4-carboxybutyl)triphenylphosphonium bromide in the presence of an excess base to form a mixture comprising a compound according to formula (11-1a) and a compound according to formula (11-1b);

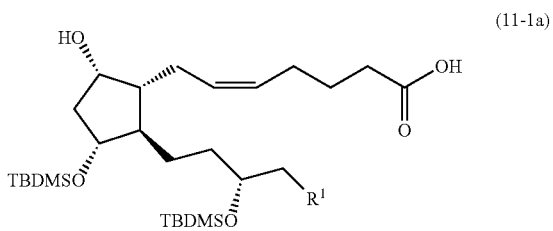

(11-1a)

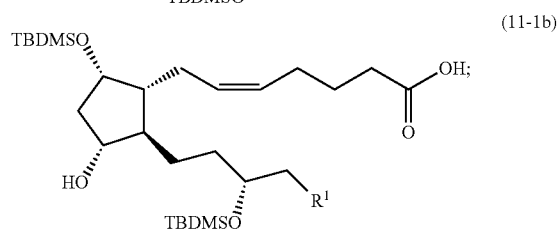

(11-1b)

(h) treating said mixture to convert the carboxylic acid moiety to other functional groups R$^2$ to form a mixture comprising a compound according to formula (12-Xa) and a compound according to formula (12-Xb);

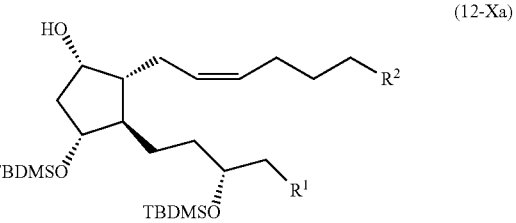

(12-Xa)

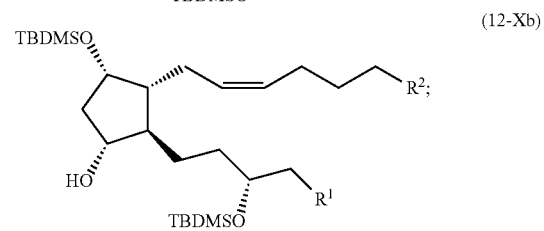

(12-Xb)

wherein:
R$^2$ is —CO$_2$R$^3$, —CONR$^4$R$^5$, —C(O)R$^3$, —C(O)CH$_2$X$^6$, or —CH$_2$X$^6$;

$X^6$ is halo or $-OR^3$ $R^3$ is hydrogen, $(C_1-C_6)$-alkyl, or $-(CH_2)_n$-phenyl;

$R^4$ and $R^5$ are independently hydrogen, $(C_1-C_6)$-alkyl, or $-(CH_2)_n$-phenyl;

n is 0, 1, or 2; and any phenyl of $R^3$, $R^4$ or $R^5$ may be optionally substituted with one or more of any one or combination of halo, trifluoromethyl, hydroxy, trifluoromethoxy, amino, cyano, $(C_1-C_6)$-alkyl, $(C_1-C_6)$-alkoxy, or $(C_1-C_6)$-alkylthio;

and (i) deprotecting said mixture comprising said compound according to formula (12-Xa) and said compound according to formula (12-Xb) to form a prostaglandin $F_{2\alpha}$ analog of structural formula (6):

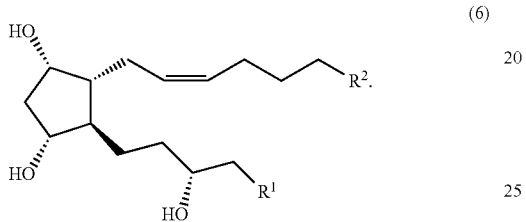

29. A method of forming a high purity prostaglandin $F_{2\alpha}$ analog of structural formula (6) comprising:

(a) providing a compound according to formula (C1):

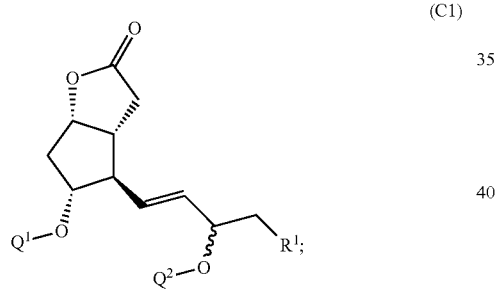

wherein:

$R^1$ is

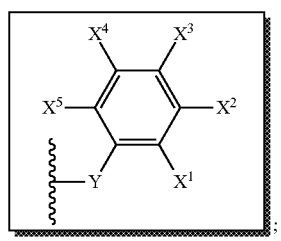

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1) that are not TBDMS;

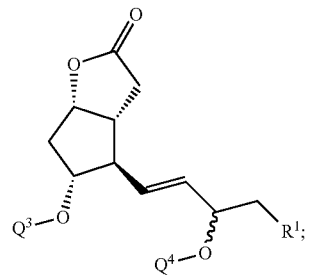

wherein each $Q^3$ and $Q^4$ is hydrogen; or wherein one of $Q^3$ and $Q^4$ is TBDMS and the other is hydrogen;

(c) introducing elemental hydrogen to reduce a double bond on a aliphatic chain extending off a cyclopentyl ring to said compound according to formula (B1) to form the compound according to formula (B2);

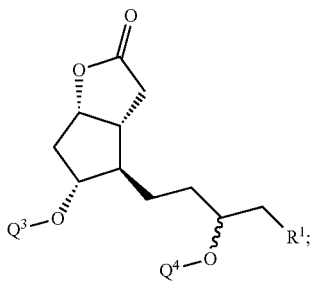

(d) transforming said compound according to formula (B2) to a compound according to formula (A2) by the step of tert-butyldimethylsilylation, wherein said compound according to formula (A2) includes a mixture of α-OTBDMS and β-OTBDMS on its aliphatic chain, said mixture therefore defining an aliphatic chain α-OTBDMS/β-OTBDMS mixture ratio;

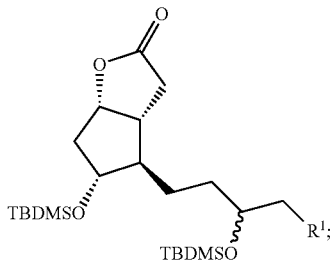

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

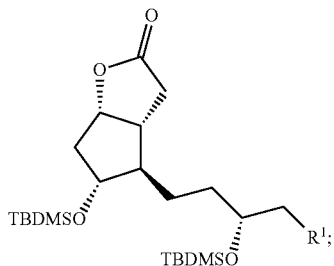

(2)

wherein:
R$^1$ is

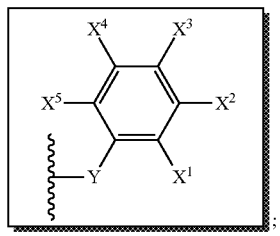

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio;
(f) performing a lactone reduction of said solid compound according to formula (1) to form a compound according to formula (10);

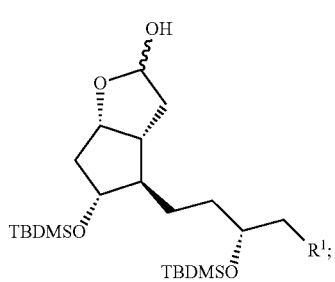

(10)

(g) reacting said compound according to formula (10) with (4-carboxybutyl)triphenylphosphonium bromide in the presence of an excess base to form a mixture comprising a compound according to formula (11-1a) and a compound according to formula (11-1b);

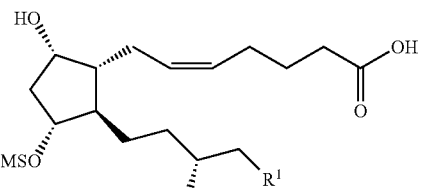

(11-1a)

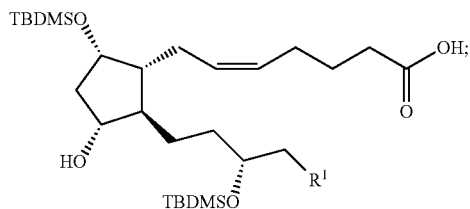

(11-1b)

(h) treating said mixture to convert the carboxylic acid moiety to other functional groups R$^2$ to form a mixture comprising a compound according to formula (12-Xa) and a compound according to formula (12-Xb);

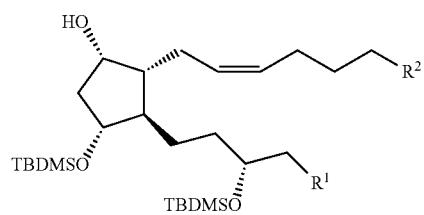

(12-Xa)

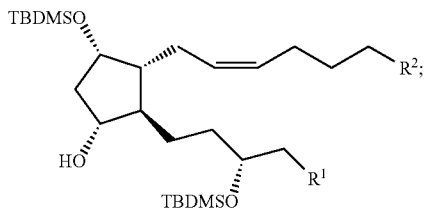

(12-Xb)

wherein:
R$^2$ is —CO$_2$R$^3$, —CONR$^4$R$^5$, —C(O)R$^3$, —C(O)CH$_2$X$^6$, or —CH$_2$X$^6$;
X$^6$ is halo or —OR$^3$
R$^3$ is hydrogen, (C$_1$-C$_6$)-alkyl, or —(CH$_2$)$_n$-phenyl;
R$^4$ and R$^5$ are independently hydrogen, (C$_1$-C$_6$)-alkyl, or —(CH$_2$)$_n$-phenyl;
n is 0, 1, or 2; and
any phenyl of R$^3$, R$^4$ or R$^5$ may be optionally substituted with one or more of any one or combination of halo, trifluoromethyl, hydroxy, trifluoromethoxy, amino, cyano, (C$_1$-C$_6$)-alkyl, (C$_1$-C$_6$)-alkoxy, or (C$_1$-C$_6$)-alkylthio;

and (i) deprotecting said mixture comprising said compound according to formula (12-Xa) and said compound according to formula (12-Xb) to form a prostaglandin F$_{2\alpha}$ analog of structural formula (6):

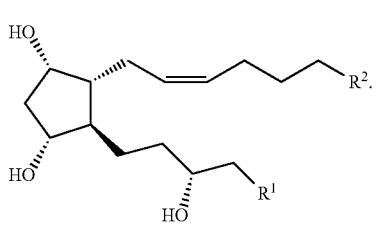

(6)

30. A method of forming a high purity prostaglandin $F_{2\alpha}$ analog of structural formula (6) comprising:

(a) providing a compound according to formula (C1):

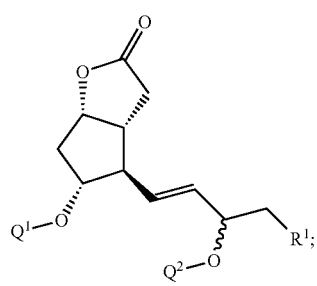

(C1)

wherein:

$R^1$ is

[structure with phenyl ring bearing X¹, X², X³, X⁴, X⁵ and Y]

Y is $CH_2$, O, S, or NH;

$X^1$, $X^2$, $X^3$, $X^4$, and $X^5$ are independently hydrogen, halo, trifluoromethyl, hydroxy, trifluoromethoxy, ($C_1$-$C_3$)-alkyl, ($C_1$-$C_3$)-alkoxy, or ($C_1$-$C_3$)-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1);

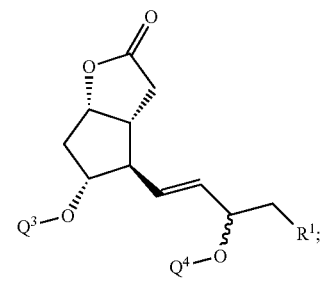

(B1)

wherein each $Q^3$ and $Q^4$ is hydrogen;

(c) introducing elemental hydrogen to reduce a double bond on a aliphatic chain extending off a cyclopentyl ring to said compound according to formula (B1) to form the compound according to formula (B2);

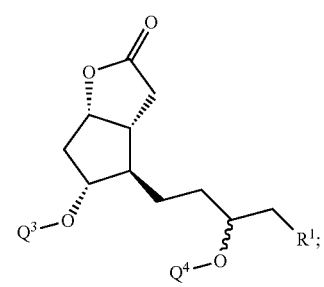

(B2)

(d) transforming said compound according to formula (B2) to a compound according to formula (A2) by the step of tert-butyldimethylsilylation, wherein said compound according to formula (A2) includes a mixture of α-OTBDMS and β-OTBDMS on its aliphatic chain, said mixture therefore defining an aliphatic chain α-OTBDMS/β-OTBDMS mixture ratio;

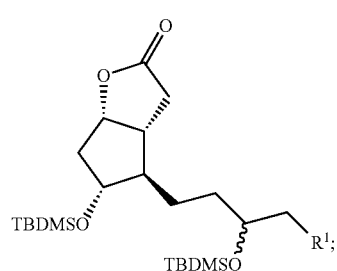

(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

(2)

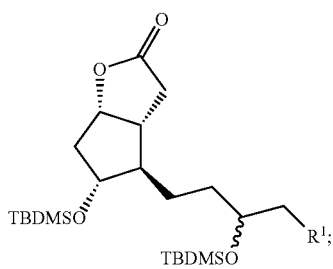

wherein:
R$^1$ is

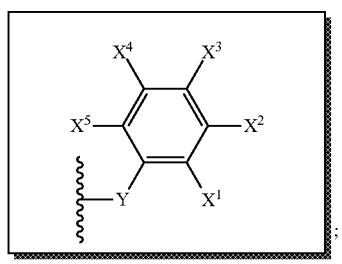

Y is CH$_2$, O, S, or NH;
X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio;

(f) performing a lactone reduction of said solid compound according to formula (1) to form a compound according to formula (10);

(10)

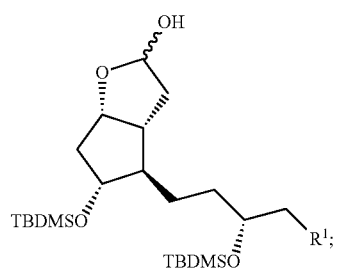

(g) reacting said compound according to formula (10) with (4-carboxybutyl)triphenylphosphonium bromide in the presence of an excess base to form a mixture comprising a compound according to formula (11-1a) and a compound according to formula (11-1b);

(11-1a)

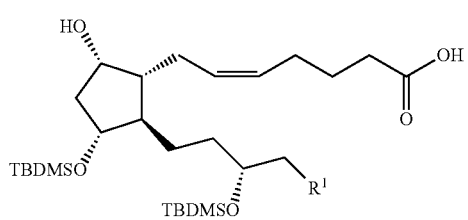

-continued (11-1b)

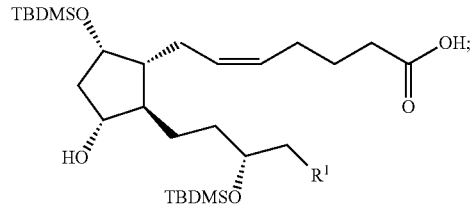

(h) treating said mixture to convert the carboxylic acid moiety to other functional groups R$^2$ to form a mixture comprising a compound according to formula (12-Xa) and a compound according to formula (12-Xb);

(12-Xa)

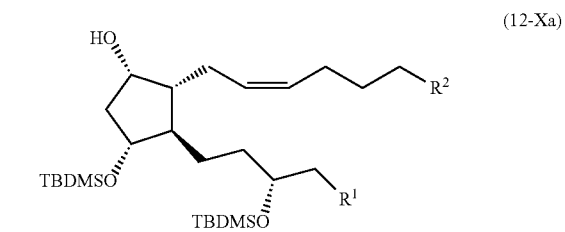

(12-Xb)

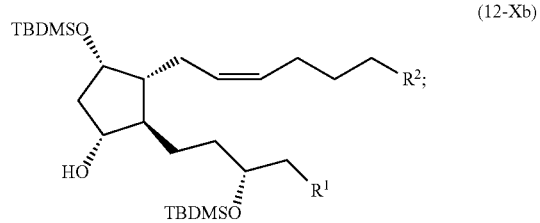

wherein:
R$^2$ is —CO$_2$R$^3$, —CONR$^4$R$^5$, —C(O)R$^3$, —C(O)CH$_2$X$^6$, or —CH$_2$X$^6$;
X$^6$ is halo or —OR$^3$
R$^3$ is hydrogen, (C$_1$-C$_6$)-alkyl, or —(CH$_2$)$_n$-phenyl;
R$^4$ and R$^5$ are independently hydrogen, (C$_1$-C$_6$)-alkyl, or —(CH$_2$)$_n$-phenyl;
n is 0, 1, or 2; and
any phenyl of R$^3$, R$^4$ or R$^5$ may be optionally substituted with one or more of any one or combination of halo, trifluoromethyl, hydroxy, trifluoromethoxy, amino, cyano, (C$_1$-C$_6$)-alkyl, (C$_1$-C$_6$)-alkoxy, or (C$_1$-C$_6$)-alkylthio;
and
(i) deprotecting said mixture comprising said compound according to formula (12-Xa) and said compound according to formula (12-Xb) to form a prostaglandin F$_{2\alpha}$ analog of structural formula (6):

(6)

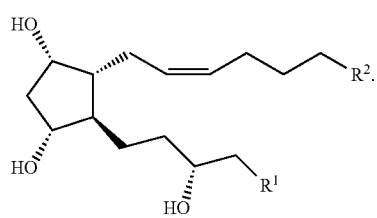

31. A method of forming a high purity prostaglandin $F_{2\alpha}$ analog of structural formula (6) comprising:

(a) providing a compound according to formula (C1):

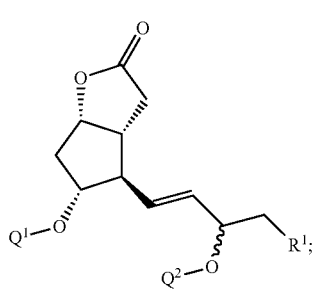

(C1)

wherein:
R¹ is

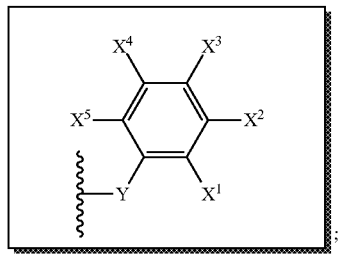

Y is $CH_2$, O, S, or NH;
$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and
each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1) that are not TBDMS;

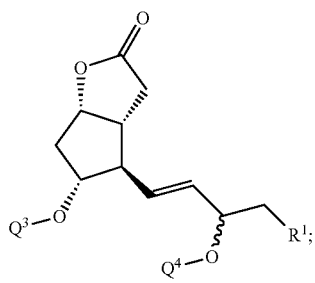

(B1)

wherein each $Q^3$ and $Q^4$ is hydrogen; or wherein one of $Q^3$ and $Q^4$ is TBDMS and the other is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

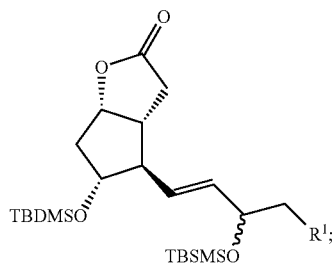

(A1)

(d) introducing elemental hydrogen to reduce a double bond on a aliphatic chain extending off a cyclopentyl ring to said compound according to formula (A1) to form the compound according to formula (A2);

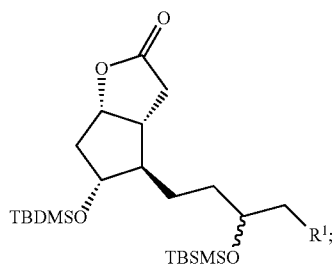

(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

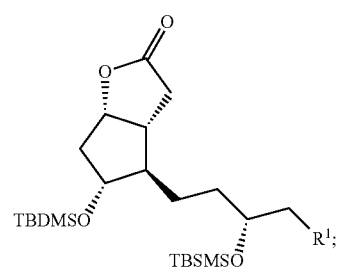

(2)

wherein:

$R^1$ is

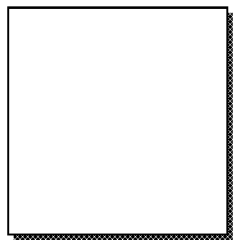

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio;

(f) performing a lactone reduction of said solid compound according to formula (1) to form a compound according to formula (10);

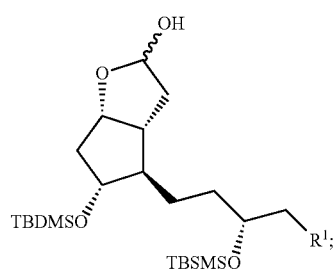
(10)

(g) reacting said compound according to formula (10) with (4-carboxybutyl)triphenylphosphonium bromide in the presence of an excess base to form a mixture comprising a compound according to formula (11-1a) and a compound according to formula (11-1b);

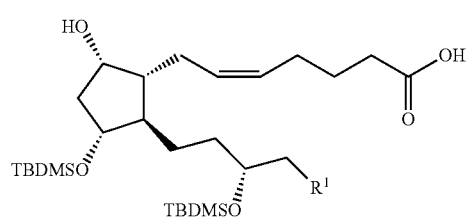
(11-1a)

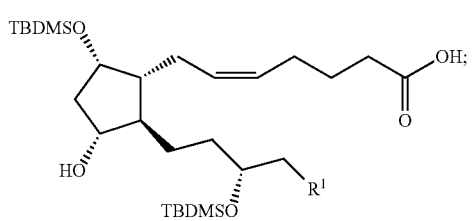
(11-1b)

(h) treating said mixture to convert the carboxylic acid moiety to other functional groups $R^2$ to form a mixture comprising a compound according to formula (12-Xa) and a compound according to formula (12-Xb);

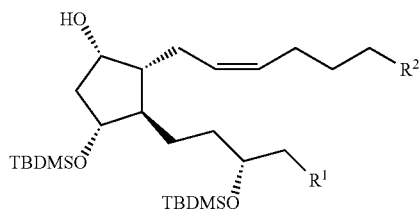
(12-Xa)

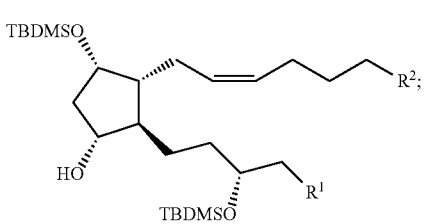
(12-Xb)

wherein:

$R^2$ is $—CO_2R^3$, $—CONR^4R^5$, $—C(O)R^3$, $—C(O)CH_2X^6$, or $—CH_2X^6$;

$X^6$ is halo or $—OR^3$ $R^3$ is hydrogen, $(C_1-C_6)$-alkyl, or $—(CH_2)_n$-phenyl;

$R^4$ and $R^5$ are independently hydrogen, $(C_1-C_6)$-alkyl, or $—(CH_2)_n$-phenyl;

n is 0, 1, or 2; and any phenyl of $R^3$, $R^4$ or $R^5$ may be optionally substituted with one or more of any one or combination of halo, trifluoromethyl, hydroxy, trifluoromethoxy, amino, cyano, $(C_1-C_6)$-alkyl, $(C_1-C_6)$-alkoxy, or $(C_1-C_6)$-alkylthio;

and (i) deprotecting said mixture comprising said compound according to formula (12-Xa) and said compound according to formula (12-Xb) to form a prostaglandin $F_{2\alpha}$ analog of structural formula (6):

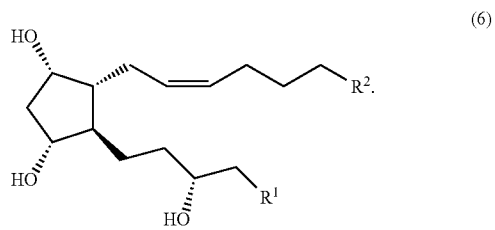
(6)

32. A method of forming a high purity prostaglandin $F_{2\alpha}$ analog of structural formula (6) comprising:

(a) providing a compound according to formula (C1):

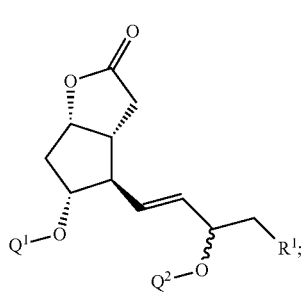
(C1)

wherein:

$R^1$ is

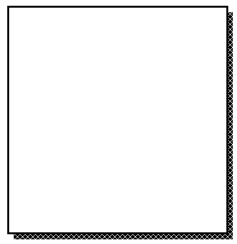
;

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1\text{-}C_3)$-alkyl, $(C_1\text{-}C_3)$-alkoxy, or $(C_1\text{-}C_3)$-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1);

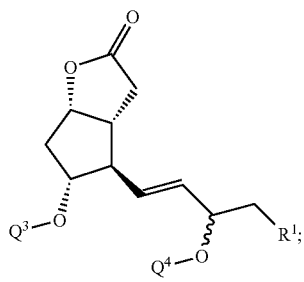
(B1)

wherein each $Q^3$ and $Q^4$ is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

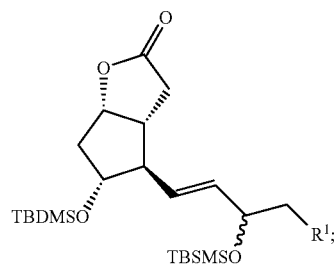
(A1)

(d) introducing elemental hydrogen to reduce a double bond on a aliphatic chain extending off a cyclopentyl ring to said compound according to formula (A1) to form the compound according to formula (A2);

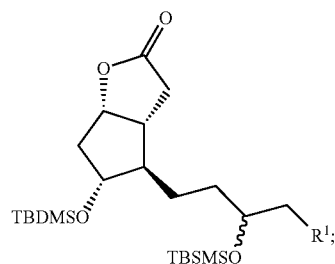
(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

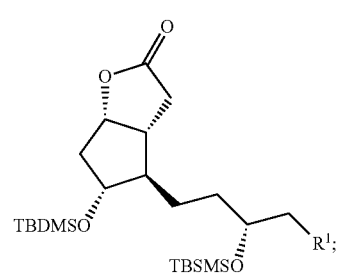
(2)

wherein:

R¹ is

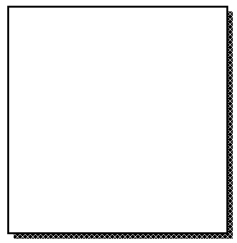

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1\text{-}C_3)$-alkyl, $(C_1\text{-}C_3)$-alkoxy, or $(C_1\text{-}C_3)$-alkylthio;

(f) performing a lactone reduction of said solid compound according to formula (1) to form a compound according to formula (10);

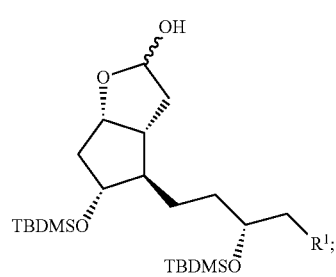

(10)

(g) reacting said compound according to formula (10) with (4-carboxybutyl)triphenylphosphonium bromide in the presence of an excess base to form a mixture comprising a compound according to formula (11-1a) and a compound according to formula (11-1b);

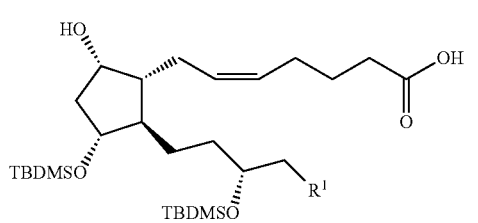

(11-1a)

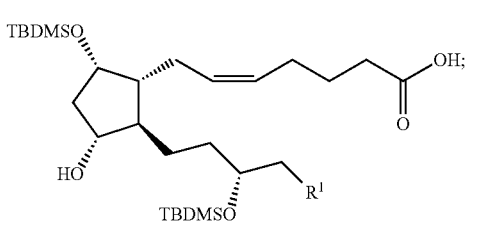

(11-1b)

(h) treating said mixture to convert the carboxylic acid moiety to other functional groups $R^2$ to form a mixture comprising a compound according to formula (12-Xa) and a compound according to formula (12-Xb);

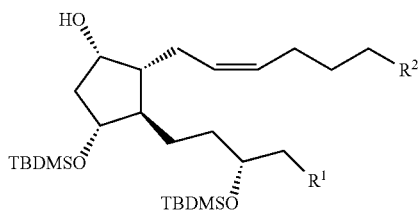

(12-Xa)

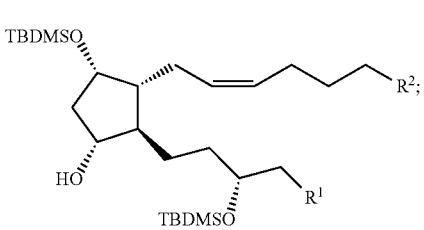

(12-Xb)

wherein:

$R^2$ is $-CO_2R^3$, $-CONR^4R^5$, $-C(O)R^3$, $-C(O)CH_2X^6$, or $-CH_2X^6$;

$X^6$ is halo or $-OR^3$;

$R^3$ is hydrogen, $(C_1\text{-}C_6)$-alkyl, or $-(CH_2)_n$-phenyl;

$R^4$ and $R^5$ are independently hydrogen, $(C_1\text{-}C_6)$-alkyl, or $-(CH_2)_n$-phenyl;

n is 0, 1, or 2; and any phenyl of $R^3$, $R^4$ or $R^5$ may be optionally substituted with one or more of any one or combination of halo, trifluoromethyl, hydroxy, trifluoromethoxy, amino, cyano, $(C_1\text{-}C_6)$-alkyl, $(C_1\text{-}C_6)$-alkoxy, or $(C_1\text{-}C_6)$-alkylthio;

and (i) deprotecting said mixture comprising said compound according to formula (12-Xa) and said compound according to formula (12-Xb) to form a prostaglandin $F_{2\alpha}$ analog of structural formula (6):

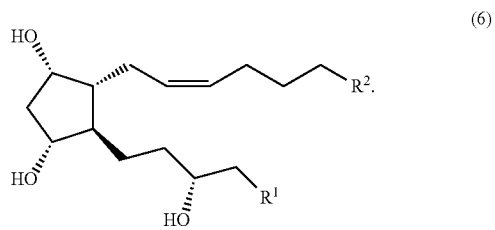

(6)

33. A method of forming a high purity prostaglandin $F_{2\alpha}$ analog of structural formula (6) comprising:

(a) providing a compound according to formula (C1):

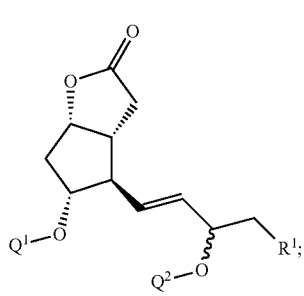
(C1)

wherein:
R¹ is

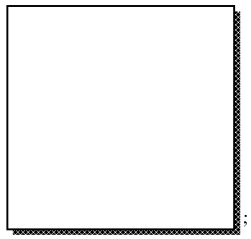
;

Y is $CH_2$, O, S, or NH;

$X^1$, $X^2$, $X^3$, $X^4$, and $X^5$ are independently hydrogen, halo, trifluoromethyl, hydroxy, trifluoromethoxy, $(C_1-C_3)$-alkyl, $(C_1-C_3)$-alkoxy, or $(C_1-C_3)$-alkylthio; and each $Q^1$ and $Q^2$ is independently a protecting group that is not tert-butyldimethylsilyl (TBDMS); or wherein one of $Q^1$ and $Q^2$ is TBDMS and the other is a protecting group that is not TBDMS; or wherein one of $Q^1$ and $Q^2$ is hydrogen and the other is a protecting group that is not TBDMS;

(b) forming a compound according to formula (B1) by removing the protecting groups of $Q^1$ and $Q^2$ from said compound according to formula (C1);

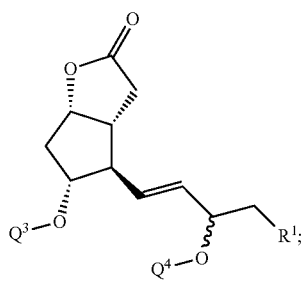
(B1)

wherein each $Q^3$ and $Q^4$ is hydrogen;

(c) transforming said compound according to formula (B1) to a compound according to formula (A1) by the step of tert-butyldimethylsilylation, wherein said compound according to formula (A1) includes a mixture of α-OTBDMS and β-OTBDMS on its aliphatic chain, said mixture therefore defining an aliphatic chain α-OTBDMS/β-OTBDMS mixture ratio;

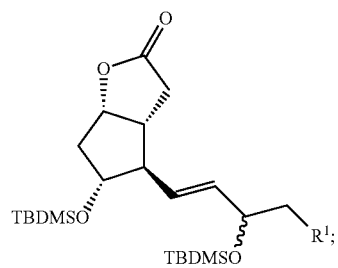
(A1)

(d) introducing elemental hydrogen to reduce a double bond on a aliphatic chain extending off a cyclopentyl ring to said compound according to formula (A1) to form the compound according to formula (A2);

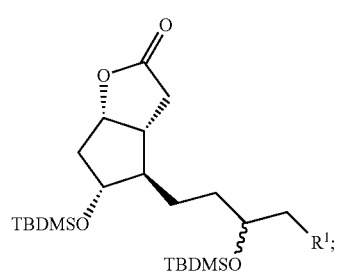
(A2)

(e) purifying said compound according to formula (A2) to form a solid precipitate of a compound according to formula (2), said solid precipitate of said compound according to formula (2) having a higher aliphatic chain α-OTBDMS/β-OTBDMS mixture ratio than said α-OTBDMS/β-OTBDMS ratio of said compound according to formula (A2);

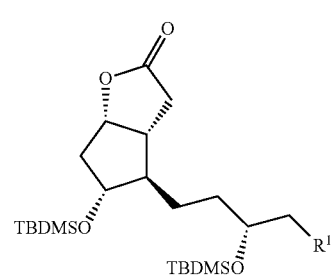
(2)

wherein:
R$^1$ is

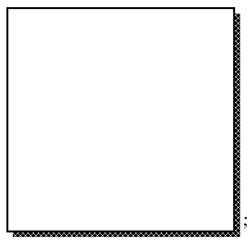
;

Y is CH$_2$, O, S, or NH;

X$^1$, X$^2$, X$^3$, X$^4$, and X$^5$ are independently hydrogen, halo, trifluoromethyl, hydroxy, trifluoromethoxy, (C$_1$-C$_3$)-alkyl, (C$_1$-C$_3$)-alkoxy, or (C$_1$-C$_3$)-alkylthio;

(f) performing a lactone reduction of said solid compound according to formula (2) to form a compound according to formula (10);

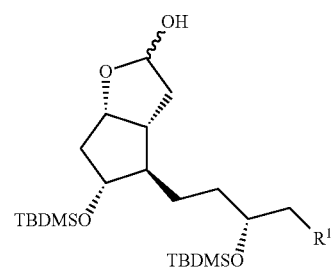
(10)

(g) reacting said compound according to formula (10) with (4-carboxybutyl)triphenylphosphonium bromide in the presence of sodium hexamethyldisilazide to form a mixture comprising a compound according to formula (11-1a) and a compound according to formula (11-1b);

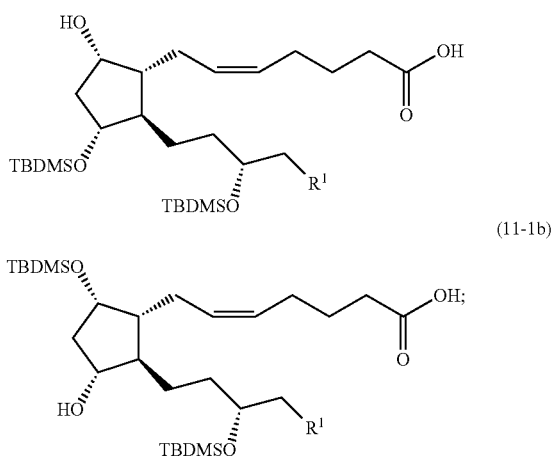

(h) treating said mixture to convert the carboxylic acid moiety to other functional groups R$^2$ to form a mixture comprising a compound according to formula (12-Xa) and a compound according to formula (12-Xb);

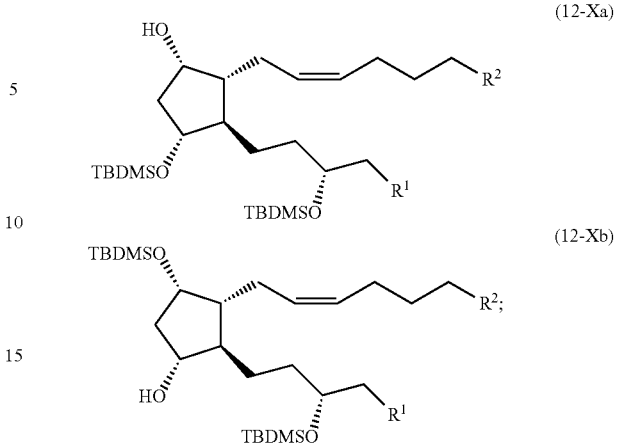

wherein:
R$^2$ is —CO$_2$R$^3$, —CONR$^4$R$^5$, —C(O)R$^3$, —C(O)CH$_2$X$^6$, or —CH$_2$X$^6$;
X$^6$ is halo or —OR$^3$
R$^3$ is hydrogen, (C$_1$-C$_6$)-alkyl, or —(CH$_2$)$_n$-phenyl;
R$^4$ and R$^5$ are independently hydrogen, (C$_1$-C$_6$)-alkyl, or —(CH$_2$)$_n$-phenyl;
n is 0, 1, or 2; and
any phenyl of R$^3$, R$^4$ or R$^5$ may be optionally substituted with one or more of any one or combination of halo, trifluoromethyl, hydroxy, trifluoromethoxy, amino, cyano, (C$_1$-C$_6$)-alkyl, (C$_1$-C$_6$)-alkoxy, or (C$_1$-C$_6$)-alkylthio;

and (i) deprotecting said mixture comprising said compound according to formula (12-Xa) and said compound according to formula (12-Xb) to form a prostaglandin F$_{2\alpha}$ analog of structural formula (6):

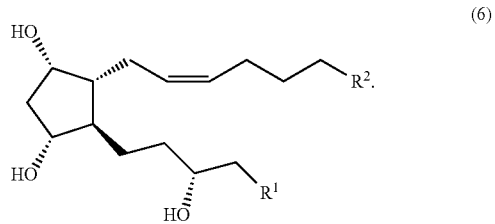

34. The method according to claim 17, wherein Y is O, S, or NH.

35. The method according to claim 17, wherein said solid precipitate of said compound according to formula (1) has at least a 0.22% enrichment in the α-OTBDMS stereoisomer as compared to said compound according to formula (A1).

36. The method according to claim 18, wherein said solid precipitate of said compound according to formula (1) has at least a 0.22% enrichment in the α-OTBDMS stereoisomer as compared to said compound according to formula (A1).

37. The method according to claim 21, wherein Y is O, S, or NH.

38. The method according to claim 21, wherein said solid precipitate of said compound according to formula (1) has at least a 0.22% enrichment in the α-OTBDMS stereoisomer as compared to said compound according to formula (A1).

39. The method according to claim 22, wherein said solid precipitate of said compound according to formula (1) has at least a 0.22% enrichment in the α-OTBDMS stereoisomer as compared to said compound according to formula (A1).

* * * * *

UNITED STATES PATENT AND TRADEMARK OFFICE
CERTIFICATE OF CORRECTION

| | | |
|---|---|---|
| PATENT NO. | : 8,901,319 B2 | Page 1 of 1 |
| APPLICATION NO. | : 13/500254 | |
| DATED | : December 2, 2014 | |
| INVENTOR(S) | : Gilles Chambournier et al. | |

It is certified that error appears in the above-identified patent and that said Letters Patent is hereby corrected as shown below:

In the Specification

IN THE DETAILED DESCRIPTION OF THE INVENTION:

Column 38, line 46: delete "1a/Epi-1a" and insert therefor -- 2a/Epi-2a --.

Column 38, line 47: delete "Step B" and insert therefor -- Step A --.

Signed and Sealed this
Seventh Day of July, 2015

Michelle K. Lee
*Director of the United States Patent and Trademark Office*

UNITED STATES PATENT AND TRADEMARK OFFICE
CERTIFICATE OF CORRECTION

PATENT NO. : 8,901,319 B2
APPLICATION NO. : 13/500254
DATED : December 2, 2014
INVENTOR(S) : Gilles Chambournier et al.

Page 1 of 1

It is certified that error appears in the above-identified patent and that said Letters Patent is hereby corrected as shown below:

In the Claims

Column 117; Claim 31 (e); The box is blank and should appear as shown below:

Column 119; Claim 32 (a); The box is blank and should appear as shown below:

Column 121; Claim 32 (e); The box is blank and should appear as shown below:

Column 123; Claim 33 (a); The box is blank and should appear as shown below:

Column 125; Claim 33 (e); The box is blank and should appear as shown below:

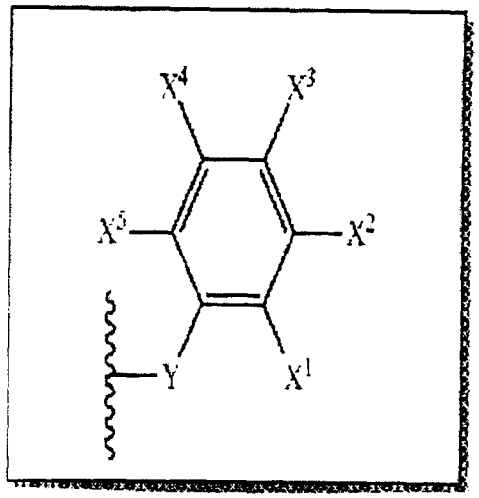

Signed and Sealed this
Sixth Day of October, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,901,319 B2 | Page 1 of 1 |
| APPLICATION NO. | : 13/500254 | |
| DATED | : December 2, 2014 | |
| INVENTOR(S) | : Chambournier et al. | |

It is certified that error appears in the above-identified patent and that said Letters Patent is hereby corrected as shown below:

IN THE CLAIMS:

Claim 29, column 109, line 41: delete "(1)" and insert therefor -- (2) --.

Claim 30, column 113, line 35: delete "(1)" and insert therefor -- (2) --.

Signed and Sealed this
Twenty-fourth Day of May, 2016

Michelle K. Lee
*Director of the United States Patent and Trademark Office*